US012538701B2

(12) United States Patent
Lim et al.

(10) Patent No.: US 12,538,701 B2
(45) Date of Patent: Jan. 27, 2026

(54) COMPOUND AND ORGANIC LIGHT EMITTING DEVICE COMPRISING THE SAME

(71) Applicant: LG Chem, Ltd., Seoul (KR)

(72) Inventors: Byeong Yun Lim, Daejeon (KR); Jaechol Lee, Daejeon (KR); Jung Ha Park, Daejeon (KR); Yongwook Kim, Daejeon (KR); Shin Sung Kim, Daejeon (KR); Leehyeon Baek, Daejeon (KR); Keunsoo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 889 days.

(21) Appl. No.: 17/788,544

(22) PCT Filed: Feb. 17, 2021

(86) PCT No.: PCT/KR2021/002030
§ 371 (c)(1),
(2) Date: Jun. 23, 2022

(87) PCT Pub. No.: WO2021/177633
PCT Pub. Date: Sep. 10, 2021

(65) Prior Publication Data

US 2023/0110973 A1 Apr. 13, 2023

(30) Foreign Application Priority Data

Mar. 3, 2020 (KR) ........................ 10-2020-0026670

(51) Int. Cl.
*H01L 51/00* (2006.01)
*C07D 487/04* (2006.01)
(Continued)

(52) U.S. Cl.
CPC ......... *H10K 85/636* (2023.02); *C07D 487/04* (2013.01); *C09K 11/06* (2013.01);
(Continued)

(58) Field of Classification Search
None
See application file for complete search history.

(56) References Cited

U.S. PATENT DOCUMENTS

| | | | |
|---|---|---|---|
| 5,942,340 | A | 8/1999 | Hu et al. |
| 2004/0251816 | A1 | 12/2004 | Leo et al. |

(Continued)

FOREIGN PATENT DOCUMENTS

| | | | |
|---|---|---|---|
| CN | 101511834 | A | 8/2009 |
| CN | 109790455 | A | 5/2019 |

(Continued)

OTHER PUBLICATIONS

International Search Report for Application No. PCT/KR2021/002030 mailed May 28, 2021, pp. 1-3.

(Continued)

*Primary Examiner* — Tae H Yoon
(74) *Attorney, Agent, or Firm* — Lerner David LLP

(57) ABSTRACT

The present disclosure provides a novel compound represented by the following Chemical Formula 1, and an organic light emitting device including the same:
(Continued)

[Chemical Formula 1]

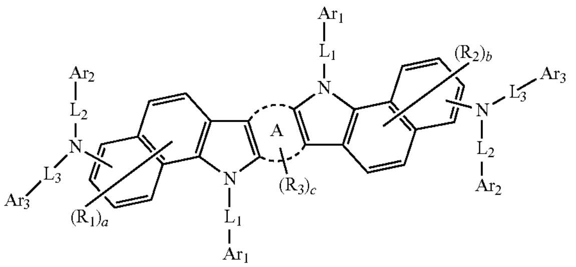

wherein A, $L_1$ to $L_3$, $Ar_1$ to $Ar_3$, $R_1$ to $R_3$, a and b are described herein.

12 Claims, 1 Drawing Sheet

(51) Int. Cl.

| | |
|---|---|
| ***C09K 11/06*** | (2006.01) |
| ***H10K 85/60*** | (2023.01) |
| *H10K 50/11* | (2023.01) |

(52) U.S. Cl.

CPC ........ *H10K 85/633* (2023.02); *C07B 2200/05* (2013.01); *C09K 2211/1018* (2013.01); *H10K 50/11* (2023.02); *H10K 85/626* (2023.02); *H10K 85/6572* (2023.02); *H10K 85/6574* (2023.02)

(56) References Cited

U.S. PATENT DOCUMENTS

| | | | |
|---|---|---|---|
| 2010/0187977 | A1 | 7/2010 | Kai et al. |
| 2015/0115205 | A1 | 4/2015 | Kang et al. |
| 2015/0155498 | A1 | 6/2015 | Ahn et al. |
| 2015/0325798 | A1 | 11/2015 | Cho et al. |
| 2019/0109286 | A1 | 4/2019 | Ma et al. |
| 2019/0189927 | A1 | 6/2019 | Lee et al. |
| 2019/0221752 | A1 | 7/2019 | Lee et al. |
| 2020/0270278 | A1 | 8/2020 | Gao et al. |

FOREIGN PATENT DOCUMENTS

| | | | |
|---|---|---|---|
| CN | 110759918 | A | 2/2020 |
| EP | 2145936 | A2 | 1/2010 |
| KR | 20000051826 | A | 8/2000 |
| KR | 20130127563 | A | 11/2013 |
| KR | 20130134202 | A | 12/2013 |
| KR | 20150129928 | A | 11/2015 |
| KR | 20170099476 | A | 9/2017 |
| KR | 20180013713 | A | 2/2018 |
| KR | 20180037881 | A | 4/2018 |
| WO | 2003012890 | A2 | 2/2003 |
| WO | 2008056746 | A1 | 5/2008 |
| WO | 2010107244 | A2 | 9/2010 |
| WO | 2015099486 | A1 | 7/2015 |
| WO | 2017146406 | A1 | 8/2017 |
| WO | 2018038544 | A1 | 3/2018 |
| WO | 2019-172647 | A1 | 9/2019 |

OTHER PUBLICATIONS

Extended European Search Report including Written Opinion for Application No. 21764418.6 dated Jan. 2, 2023, pp. 1-7.

【FIG. 1】
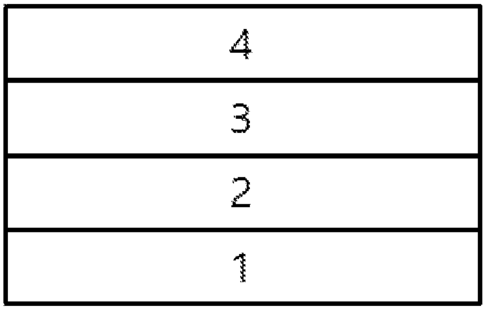
【FIG. 2】
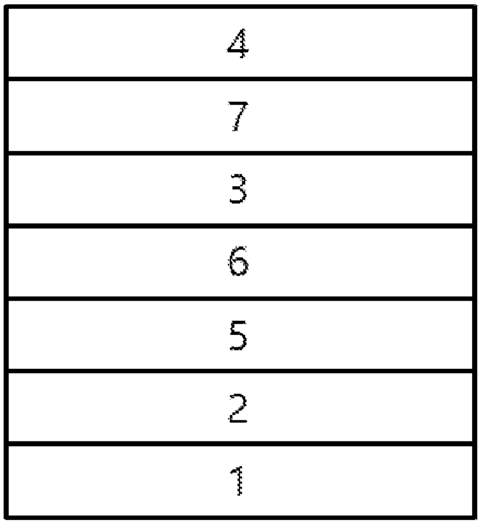

COMPOUND AND ORGANIC LIGHT EMITTING DEVICE COMPRISING THE SAME

CROSS-REFERENCE TO RELATED APPLICATION(S)

The present application is a national stage entry under 35 U.S.C. § 371 of International Application No. PCT/KR2021/002030 filed on Feb. 17, 2021, which claims priority from Korean Patent Application No. 10-2020-0026670 filed on Mar. 3, 2020, all the disclosures of which are incorporated herein by reference.

TECHNICAL FIELD

The present disclosure relates to a novel compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

For the organic materials used in the organic light emitting devices as described above, the development of new materials is continuously required.

Meanwhile, recently, in order to reduce process costs, an organic light emitting device using a solution process, particularly an inkjet process, has been developed instead of a conventional deposition process. In the initial stage of development, attempts have been made to develop organic light emitting devices by coating all organic light emitting device layers by a solution process, but current technology has limitations. Therefore, only HIL, HTL, and EML are processed in a layer device structure by a solution process, and a hybrid process utilizing traditional deposition processes is being studied as a subsequent process.

Therefore, the present disclosure provides a novel material for an organic light emitting device that can be used for an organic light emitting device and at the same time, can be used for a solution process.

PRIOR ART LITERATURE

Patent Literature (Patent Literature 0001) Korean Unexamined Patent Publication No. 10-2000-0051826

DETAILED DESCRIPTION OF THE INVENTION

Technical Problem

It is an object of the present disclosure to provide a novel compound and an organic light emitting device comprising the same.

Technical Solution

According to an aspect of the present disclosure, there is provided a compound represented by the following Chemical Formula 1:

[Chemical Formula 1]

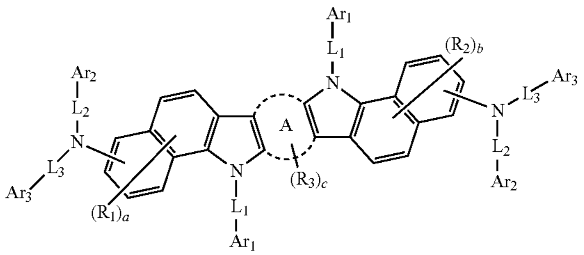

wherein in Chemical Formula 1,

A is a benzene ring fused with two adjacent pentagonal rings, $L_1$ to $L_3$ are each independently a single bond; a substituted or unsubstituted $C_{6-60}$ arylene; or a substituted or unsubstituted $C_{2-60}$ heteroarylene containing at least one heteroatom selected among N, O and S, $Ar_1$ to $Ar_3$ are each independently a substituted or unsubstituted $C_{6-60}$ aryl; or a substituted or unsubstituted $C_{2-60}$ heteroaryl containing at least one heteroatom selected among N, O and S, $R_1$ to $R_3$ are each independently deuterium; halogen; cyano; a substituted or unsubstituted $C_{1-60}$ alkyl; a substituted or unsubstituted $C_{6-60}$ aryl; or a substituted or unsubstituted $C_{2-60}$ heteroaryl containing at least one heteroatom selected among N, O and S, a and b are each independently an integer of 0 to 5, and c is an integer of 0 to 2, provided that when a, b and c are 2 or more, each of $R_1$, each of $R_2$ and each of $R_3$, respectively, are the same as or different from each other.

According to another aspect of the present disclosure, there is provided an organic light emitting device comprising: a first electrode; a second electrode that is provided opposite to the first electrode; and a light emitting layer that is provided between the first electrode and the second electrode, wherein the light emitting layer includes the compound represented by Chemical Formula 1.

Advantageous Effects

The above-mentioned compound represented by Chemical Formula 1 can be used as a material of an organic material layer in an organic light emitting device, can be used in a solution process, and can improve the efficiency and lifetime characteristics in an organic light emitting device.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 3, an electron injection and transport layer 7, and a cathode 4.

DETAILED DESCRIPTION OF THE EMBODIMENTS

Hereinafter, embodiments of the present disclosure will be described in more detail to facilitate understanding of the invention.

Definition of Terms

As used herein, the notation

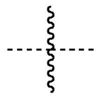

and ⁝ mean a bond linked to another substituent group, the ph means a phenyl group, and the Boc means tert-butyloxycarbonyl protecting group.

As used herein, the term "unsubstituted or substituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heteroaryl group containing at least one of N, O and S atoms, or being unsubstituted or substituted with a substituent to which two or more substituents of the above-exemplified substituents are linked. For example, "a substituent in which two or more substituents are linked" may be a biphenyl group. Namely, a biphenyl group may be an aryl group, or it may also be interpreted as a substituent in which two phenyl groups are linked.

In the present disclosure, the carbon number of a carbonyl group is not particularly limited, but is preferably 1 to 40. Specifically, the carbonyl group may be a group having the following structural formulas, but is not limited thereto.

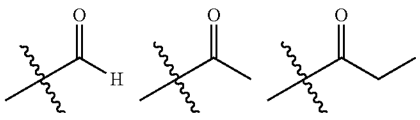

-continued

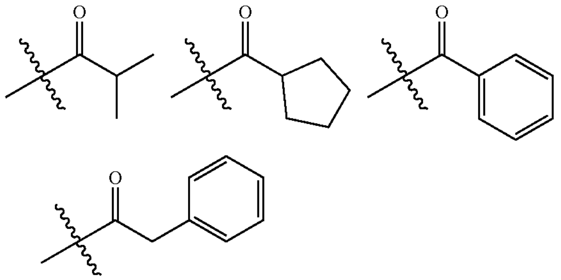

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a group having the following structural formulas, but is not limited thereto.

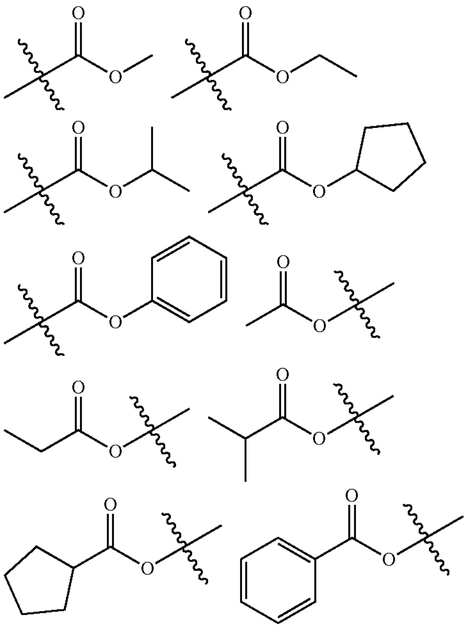

In the present disclosure, the carbon number of an imide group is not particularly limited, but is preferably 1 to 25. Specifically, the imide group may be a group having the following structural formulas, but is not limited thereto.

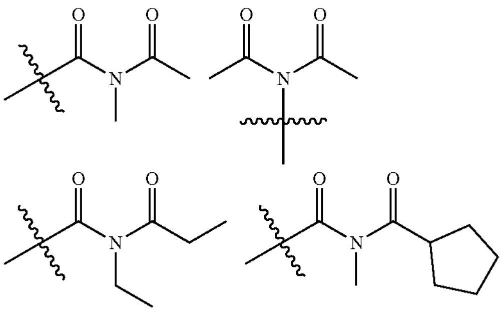

-continued

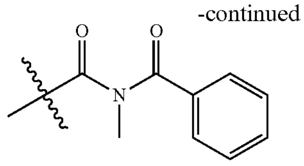

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenylyl group, a terphenylyl group or the like as the monocyclic aryl group, but is not limited thereto. The polycyclic aryl group includes a naphthyl group, an anthryl group, a phenanthryl group, a pyrenyl group, a perylenyl group, a chrysenyl group, a fluorenyl group, a benzofluorenyl group, or the like, but is not limited thereto.

In the present disclosure, the fluorenyl group may be substituted, and two substituents may be linked with each other to form a spiro structure. In the case where the fluorenyl group is substituted,

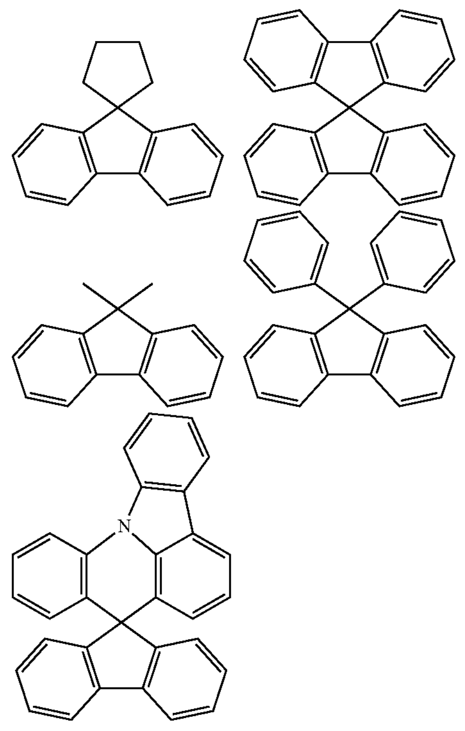

and the like can be formed. However, the structure is not limited thereto. In addition, the benzofluorenyl group may also be substituted in the same manner as the fluorenyl group, or two substituents may be linked with each other to form a spiro structure.

In the present disclosure, a heteroaryl group is a heteroaryl group containing at least one of O, N, Si and S as a heteroatom, and the carbon number thereof is not particularly limited, but is preferably 2 to 60. Examples of the heteroaryl group include xanthene, thioxanthene, a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, the arylamine group and the aryl silyl group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl group in the heteroarylamine group may be applied to the above-mentioned description of the heteroaryl group. In the present disclosure, the alkenyl group in the aralkenyl group is the same as the above-mentioned examples of the alkenyl group. In the present disclosure, the above-mentioned description of the aryl group may be applied except that the arylene is a divalent group. In the present disclosure, the above-mentioned description of the heteroaryl group can be applied except that the heteroarylene is a divalent group.

(Compound)

The present disclosure provides a compound represented by Chemical Formula 1.

The compound represented by Chemical Formula 1 has a diamine compound structure in which amino groups are substituted on both sides of a core where two benzo[g]indole structures are fused by a benzene ring. In particular, the compound represented by Chemical Formula 1 not only can be easily synthesized, but also can exhibit high solubility in an organic solvent used in the solution process, as compared to a diamine compound having a carbazolo[4,3-c]carbazole core, like a compound represented by the following Chemical Formula X1. Furthermore, the organic light emitting device employing the compound represented by Chemical Formula 1 as a dopant of the light emitting layer can simultaneously improve the light emitting efficiency and lifetime characteristics, as compared to the organic light emitting device employing the compound represented by the following Chemical Formula X1 as a dopant.

[Chemical Formula X1]

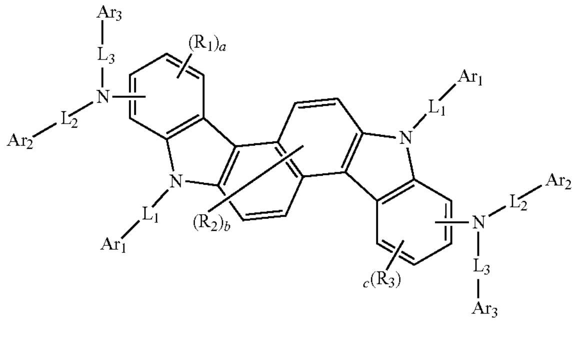

wherein in Chemical Formula X1, the description of each substituent group is as defined in Chemical Formula 1.

In particular, the compound represented by Chemical Formula 1 has high solubility in an organic solvent used in a solution process, for example, an organic solvent such as cyclohexanone, and thus is suitable for use in a large-area solution process such as an inkjet coating method using a solvent with a high boiling point.

Moreover, the compound represented by Chemical Formula 1 has a structure in which an amino group is linked to any one of the carbons *1 to *4 and any one of the carbons *1' to *4' of the core described below. An organic light emitting device employing such a compound as a dopant of the light emitting layer has the same core as described in the present disclosure like the compound represented by the following Chemical Formula X2, but can exhibit excellent light emitting efficiency and lifetime characteristics, even as compared to an organic light emitting device employing, as a dopant, a compound whose substitution positions of two amino groups are different from those described herein.

[Chemical Formula 1]

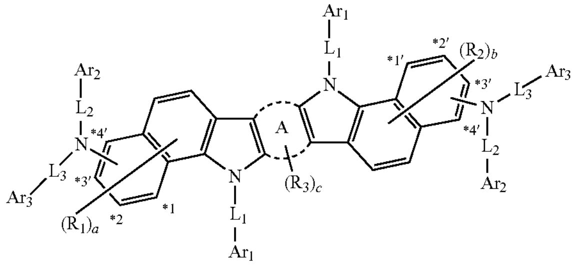

[Chemical Formula X2]

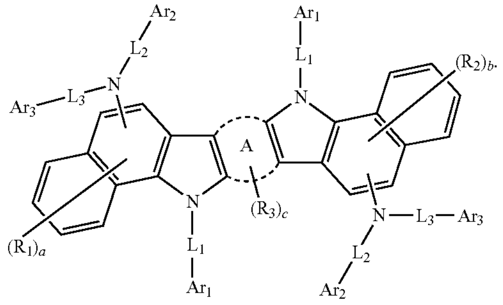

wherein in Chemical Formula X2, the description of each substituent group is as defined in Chemical Formula 1.

Meanwhile, the compound may be represented by the following Chemical Formula 1':

[Chemical Formula 1']

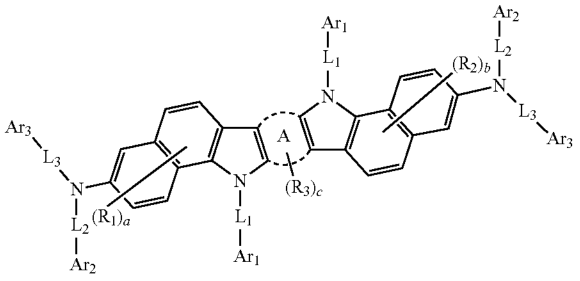

wherein in Chemical Formula 1', $L_1$ to $L_3$, $Ar_1$ to $Ar_3$, $R_1$ to $R_3$, a, b and c are as defined in Chemical Formula 1.

Specifically, the compound represented by Chemical Formula 1' may be represented by any one of the following Chemical Formulas 1-1 to 1-5, depending on the position where two benzo[g]indole structures are fused by a benzene ring:

[Chemical Formula 1-1]

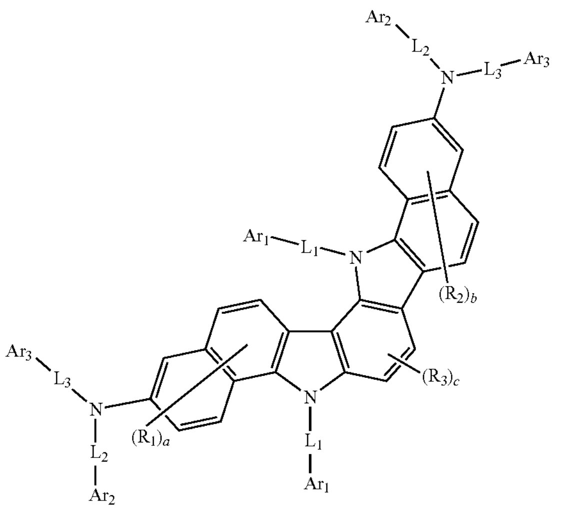

[Chemical Formula 1-2]

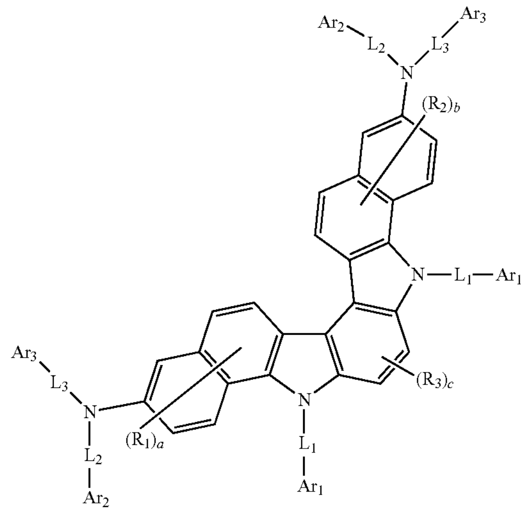

[Chemical Formula 1-3]

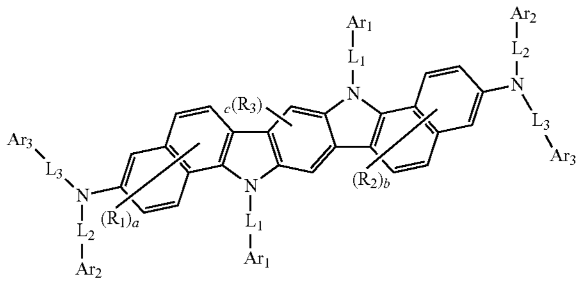

-continued

[Chemical Formula 1-4]

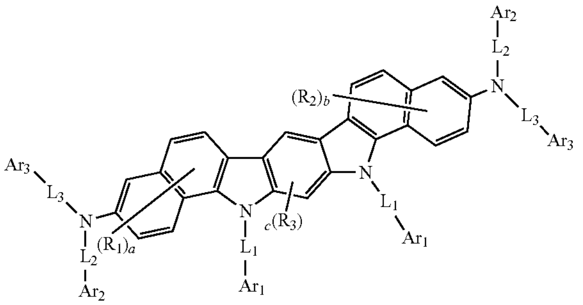

[Chemical Formula 1-5]

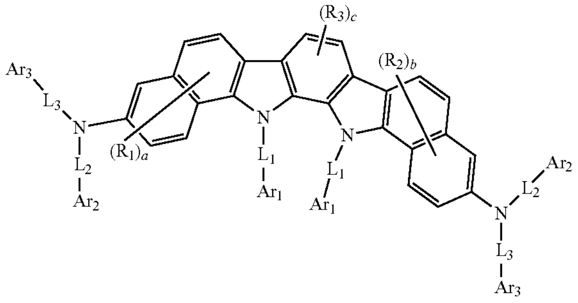

wherein in Chemical Formulas 1-1 to 1-5, $L_1$ to $L_3$, $Ar_1$ to $Ar_3$, $R_1$ to $R_3$, a, b and c are as defined in Chemical Formula 1.

Meanwhile, in Chemical Formula 1, $L_1$ to $L_3$ may be each independently a single bond; or a $C_{6-20}$ arylene which is unsubstituted or substituted with one or more substituents selected from the group consisting of deuterium, a $C_{1-10}$ alkyl and a $C_{6-20}$ aryl.

Specifically, in Chemical Formula 1, $L_1$ to $L_3$ may be each independently a single bond, phenylene, biphenyldiyl, naphthylene, or 9,9-di($C_{1-10}$ alkyl)fluorenylene.

More specifically, each $L_1$ is independently a single bond, biphenyldiyl, naphthylene, or 9,9-dimethylfluorenylene, and $L_2$ and $L_3$ are each independently a single bond, phenylene, naphthylene, 9,9-dimethylfluorenylene, or 9,9-dihexylfluorenylene.

For example, each $L_1$ is independently a single bond, or any one selected from the group consisting of:

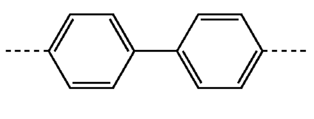

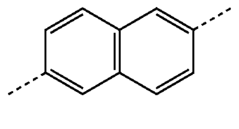

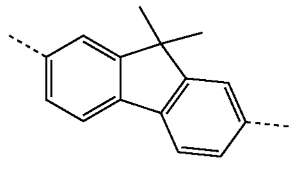

$L_2$ and $L_3$ may be each independently a single bond, or any one selected from the group consisting of:

-continued
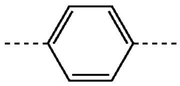
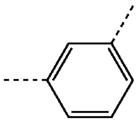
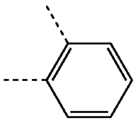
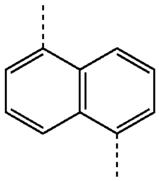
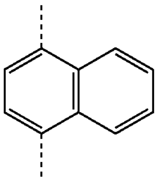
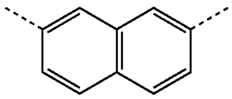
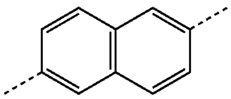
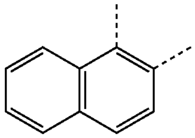
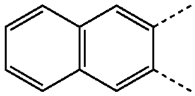
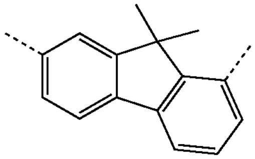
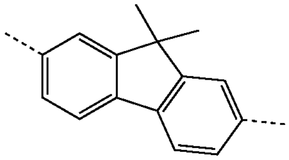
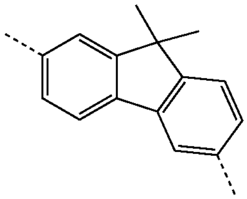
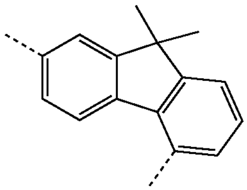
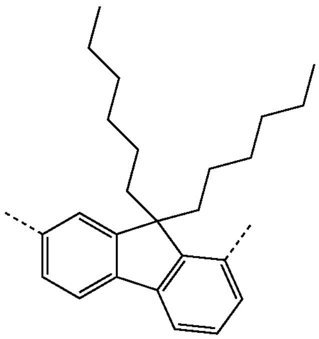
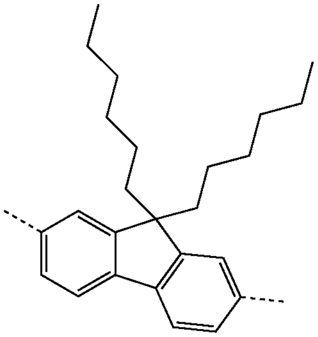
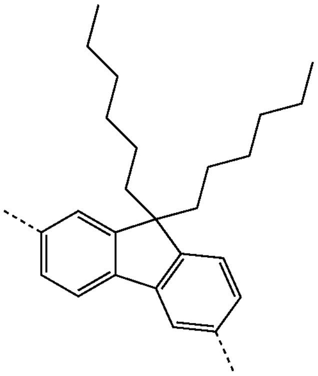
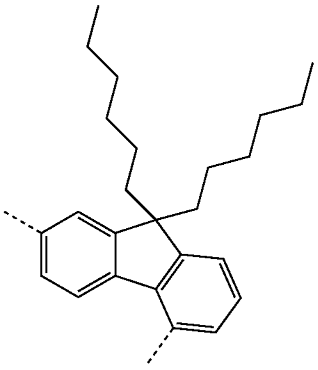
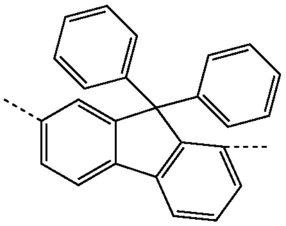
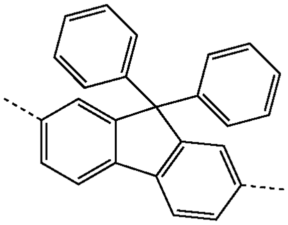

-continued

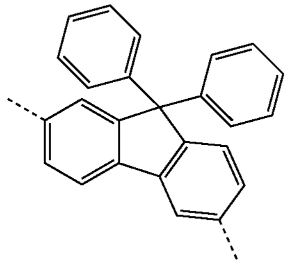

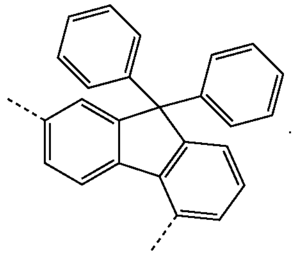

Further, in Chemical Formula 1, $Ar_1$ to $Ar_3$ may be each independently a $C_{6-20}$ aryl which is unsubstituted or substituted with one or more substituents selected from the group consisting of deuterium, a $C_{1-10}$ alkyl, a $C_{6-20}$ aryl, a $Si(C_{1-10}\ alkyl)_3$ and a $Si(C_{6-20}\ aryl)_3$; or a $C_{2-20}$ heteroaryl containing 1 or 2 heteroatoms selected among N, O and S which is unsubstituted or substituted with one or more substituents selected from the group consisting of deuterium, a $C_{1-10}$ alkyl, a $C_{6-20}$ aryl, a $Si(C_{1-10}\ alkyl)_3$ and a $Si(C_{6-20}\ aryl)_3$.

Specifically, $Ar_1$ to $Ar_3$ are each independently phenyl, naphthyl, fluorenyl, benzofluorenyl, carbazolyl, dibenzofuranyl, dibenzothiophenyl, benzofuranyl, or benzothiophenyl;

wherein, $Ar_1$ to $Ar_3$ are unsubstituted or substituted with one to five substituents selected from the group consisting of deuterium, methyl, ethyl, n-propyl, n-butyl, n-pentyl, n-hexyl, phenyl, or $Si(phenyl)_3$.

For example, each $Ar_1$ may be independently any one selected from the group consisting of:

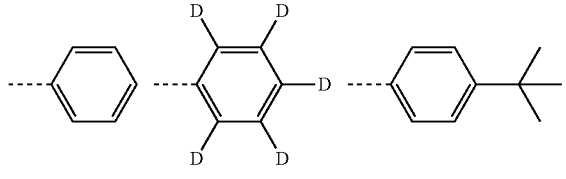

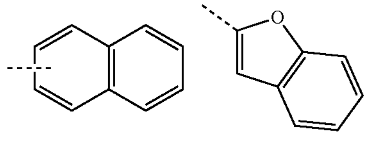

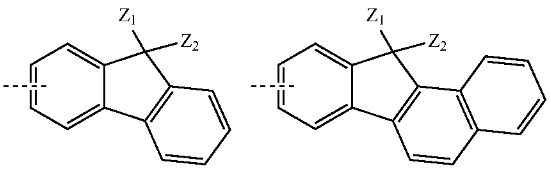

-continued

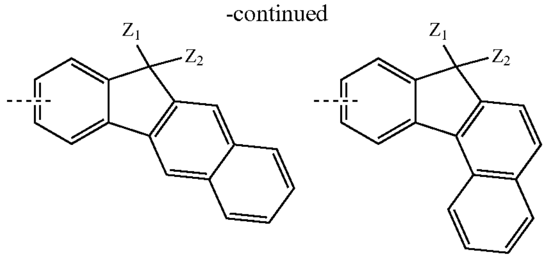

wherein, $Z_1$ and $Z_2$ are each independently methyl, ethyl, n-propyl, n-butyl, n-pentyl, n-hexyl, or phenyl.

Further, for example, $Ar_2$ and $Ar_3$ may be each independently any one selected from the group consisting of:

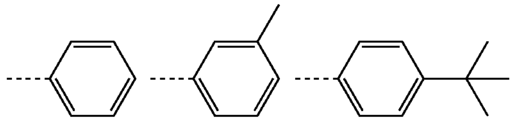

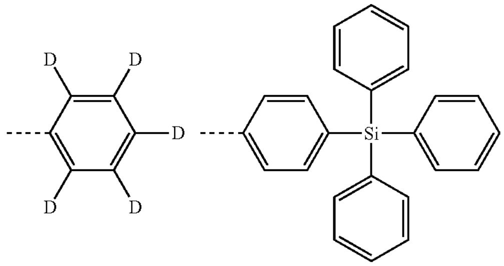

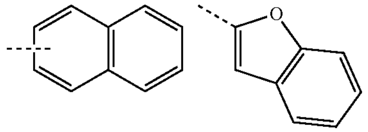

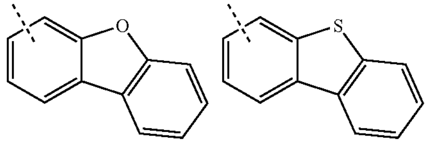

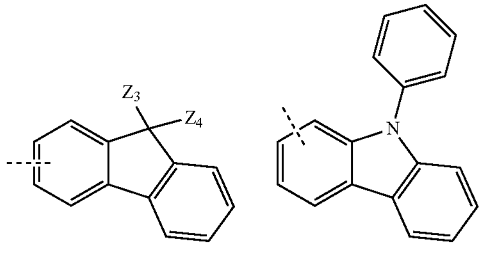

wherein, $Z_3$ and $Z_4$ are each independently methyl, ethyl, n-propyl, n-butyl, n-pentyl, n-hexyl, or phenyl.

Also, in Chemical Formula 1, one of Are and Ara may be phenyl, phenyl substituted with a $C_{1-10}$ alkyl, naphthyl, or benzofuranyl.

Further, in Chemical Formula 1, $R_1$ to $R_3$ may be each independently deuterium; halogen; cyano; a $C_{1-10}$ alkyl; or a $C_{6-20}$ aryl. In this case, a, which means the number of $R_1$, is 0, 1, 2, 3, 4, 5, or 6, b, which means the number of $R_2$, is 0, 1, 2, 3, 4, 5, or 6, and c, which means the number of $R_3$, is 0, 1, or 2.

For example, $R_1$ to $R_3$ may be each deuterium, a may be 0 or 6, b may be 0 or 6, and c may be 0 or 2, but is not limited thereto.

Further, in Chemical Formula 1, $L_1$ may be identical to each other, $L_2$ may be identical to each other, $L_3$ may be identical to each other, $Ar_1$ may be identical to each other, $Ar_2$ may be identical to each other, $Ar_3$ may be identical to each other, $R_1$ may be identical to each other, $R_2$ may be identical to each other, and $R_3$ may be identical to each other.

For example, $L_1$ may be identical to each other, $L_2$ may be identical to each other, $L_3$ may be identical to each other, $Ar_1$ may be identical to each other, $Ar_2$ may be identical to each other, $Ar_3$ may be identical to each other; or $L_1$ and $L_2$ are identical to or different from each other, $L_3$ may be different, $Ar_1$ may be different, $Ar_2$ may be identical to each other, and $Ar_3$ may be identical to each other.

In addition, the compound may be represented by any one of the following Chemical Formulas 1-1-1 to 1-5-1:

[Chemical Formula 1-1-1]

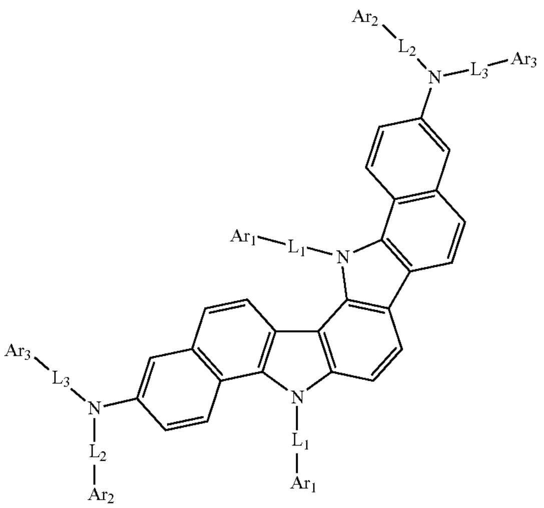

[Chemical Formula 1-2-1]

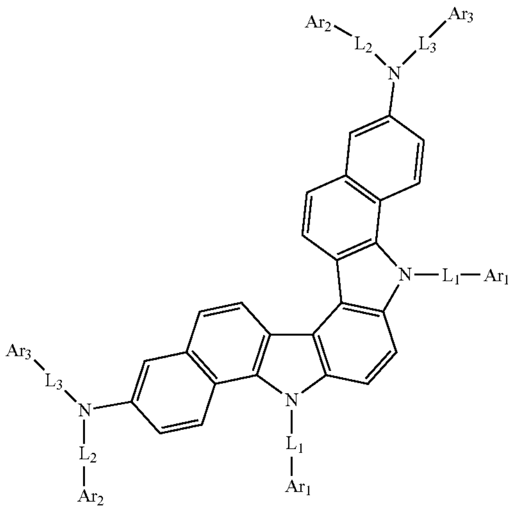

-continued

[Chemical Formula 1-3-1]

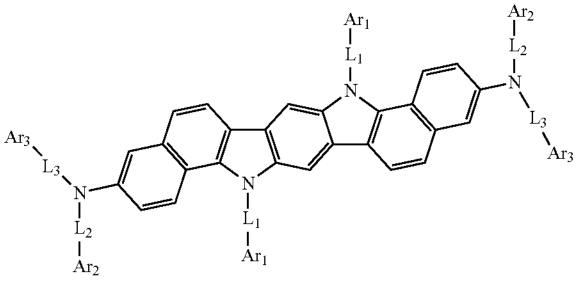

[Chemical Formula 1-4-1]

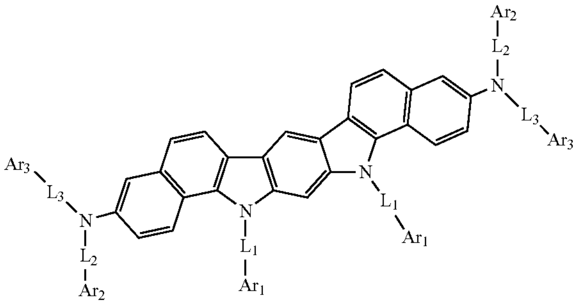

[Chemical Formula 1-5-1]

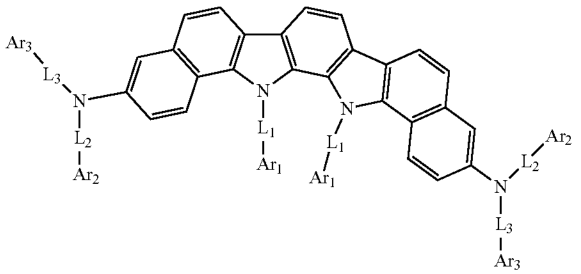

wherein in Chemical Formulas 1-1-1 to 1-5-1, each $L_1$ is independently a single bond, or any one selected from the group consisting of:

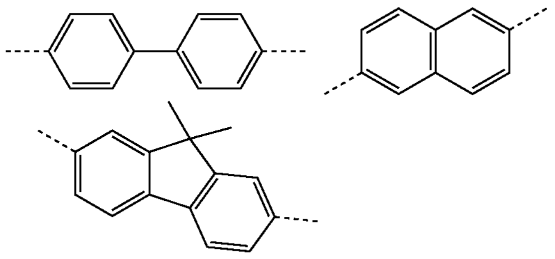

$L_2$ and $L_3$ are each independently a single bond, or any one selected from the group consisting of:

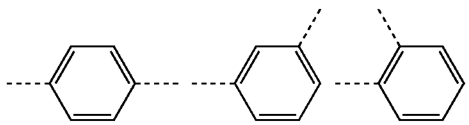

-continued
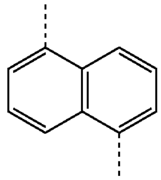
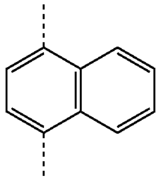
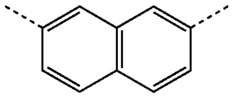
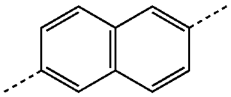
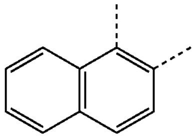
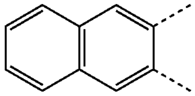
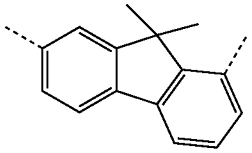
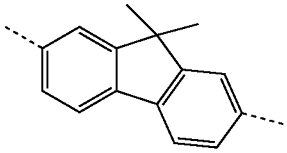
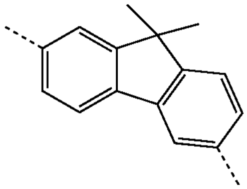
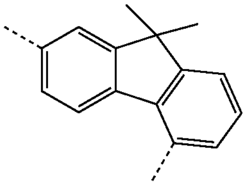
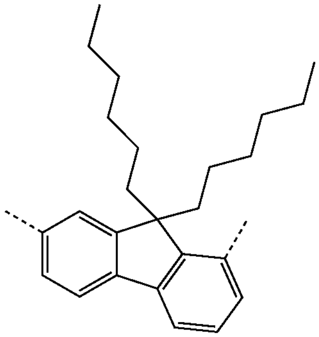
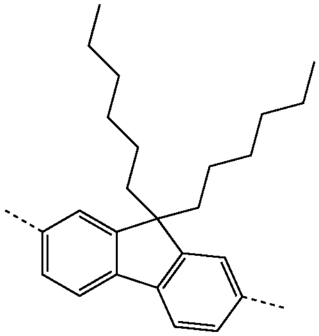
-continued
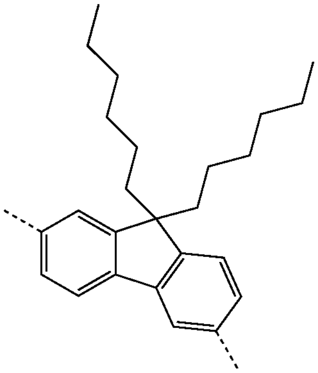
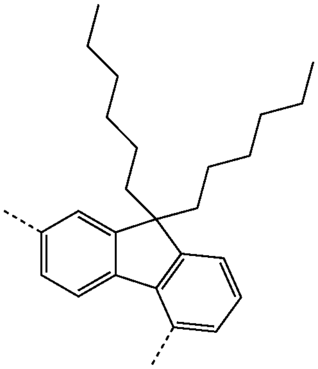
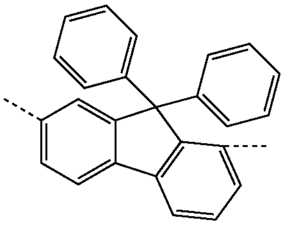
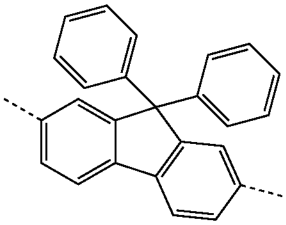
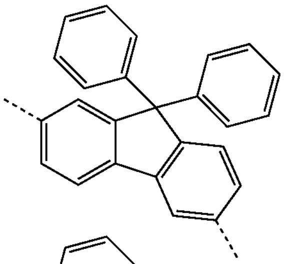
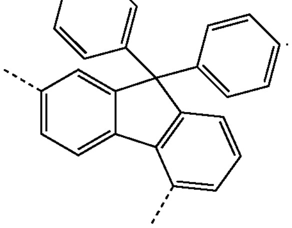
$Ar_1$ to $Ar_3$ are as defined in Chemical Formula 1.

Representative examples of the compound represented by Chemical Formula 1 are as follows:
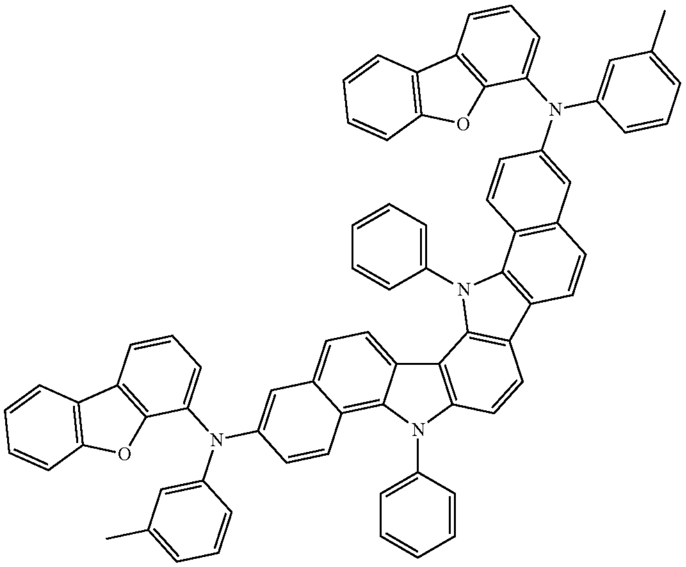
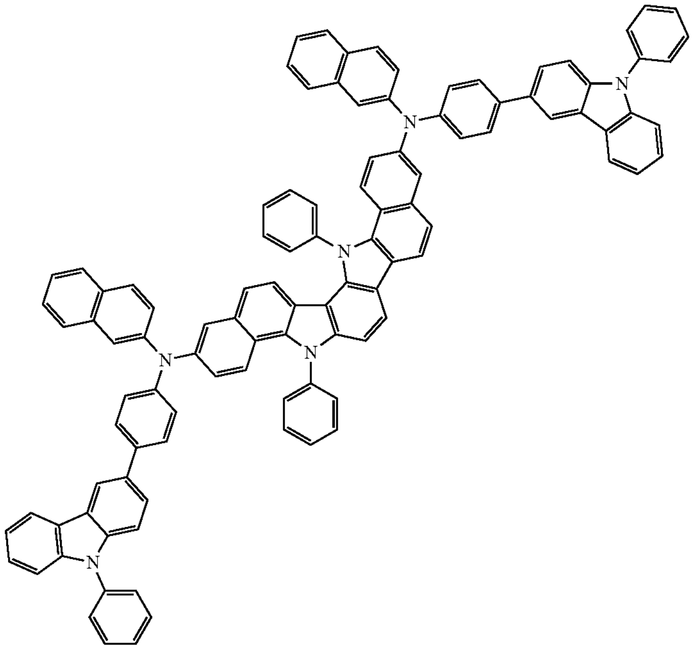

-continued
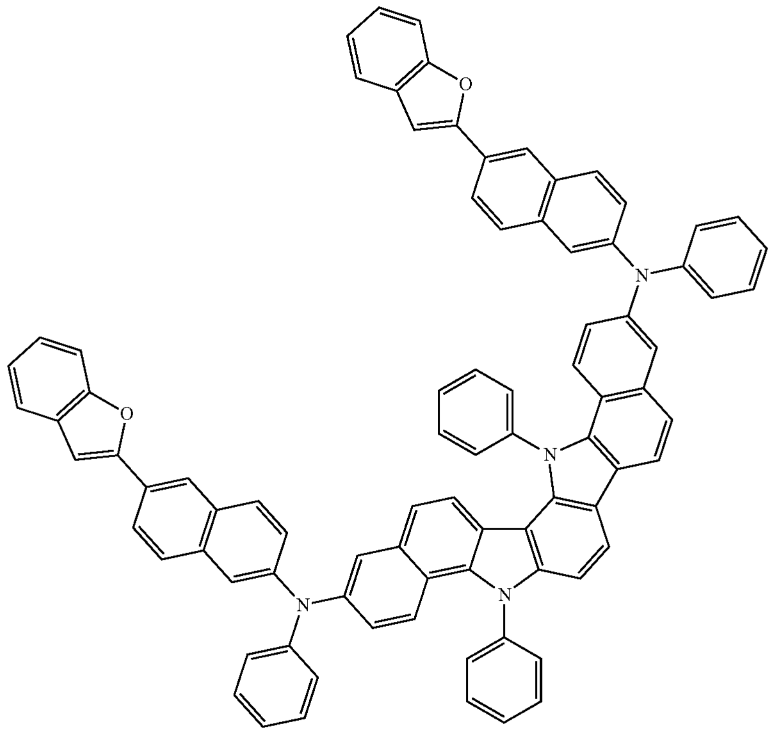
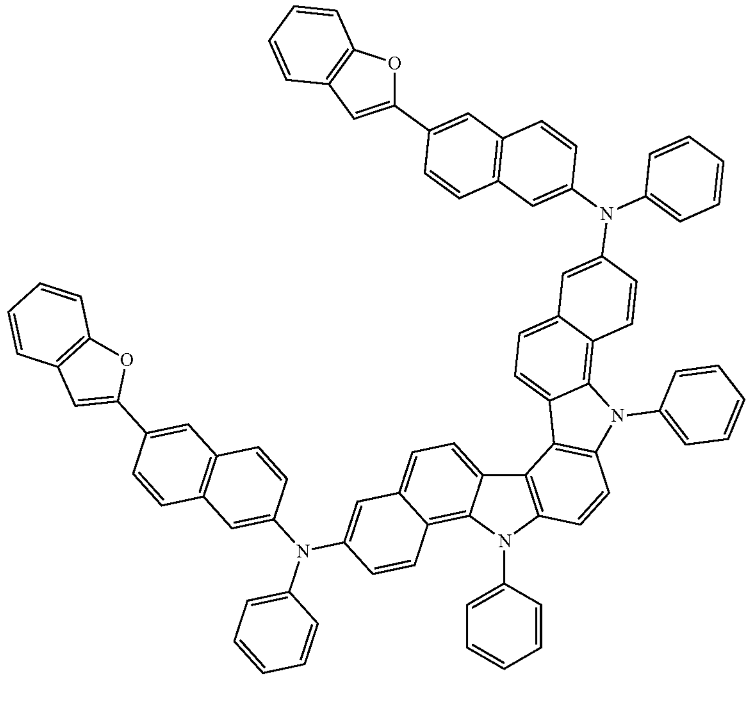

-continued
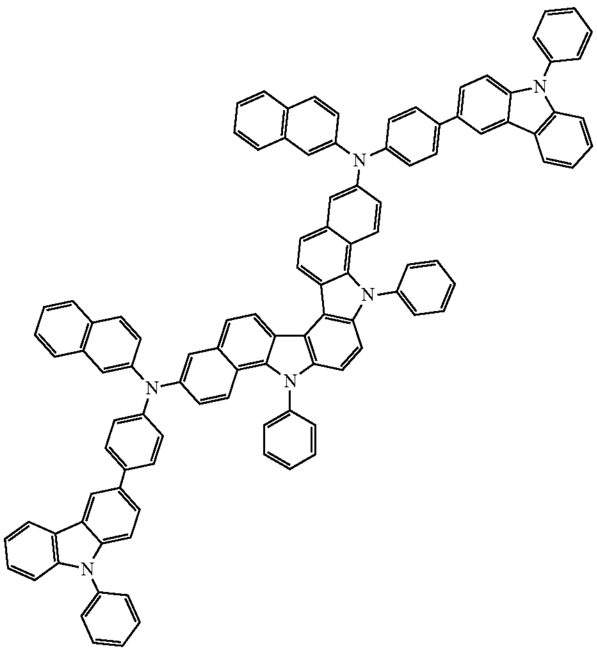
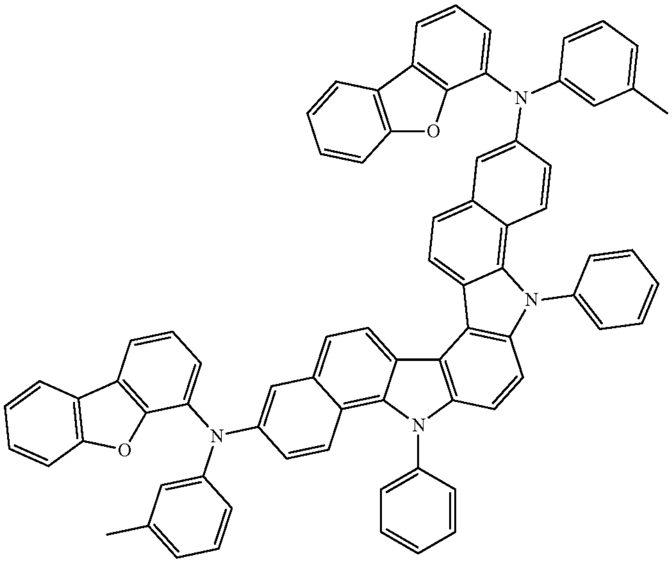
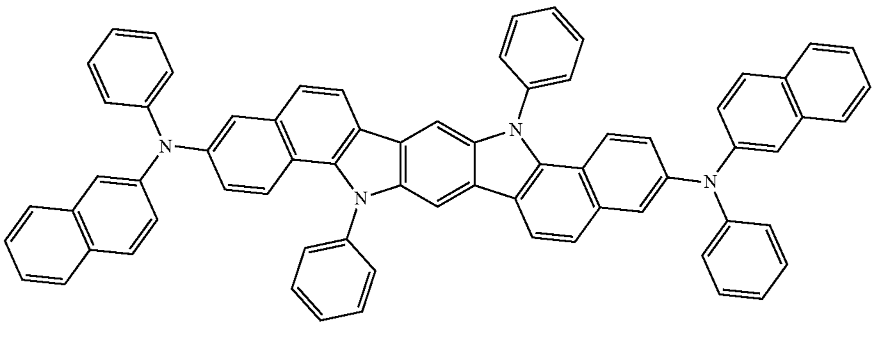

-continued
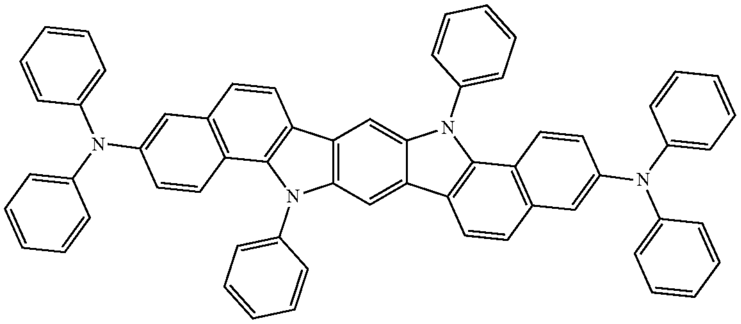
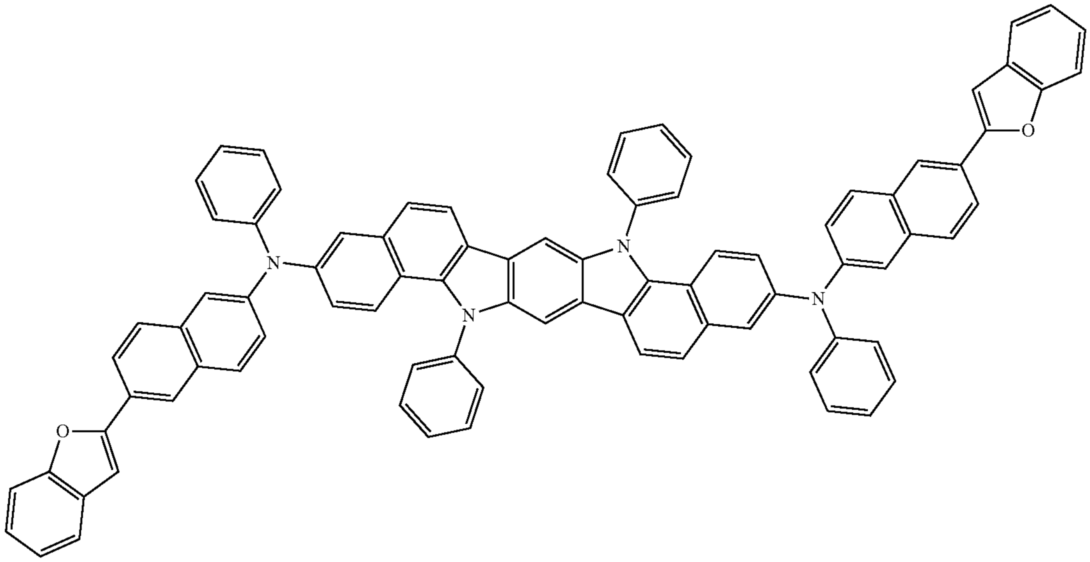
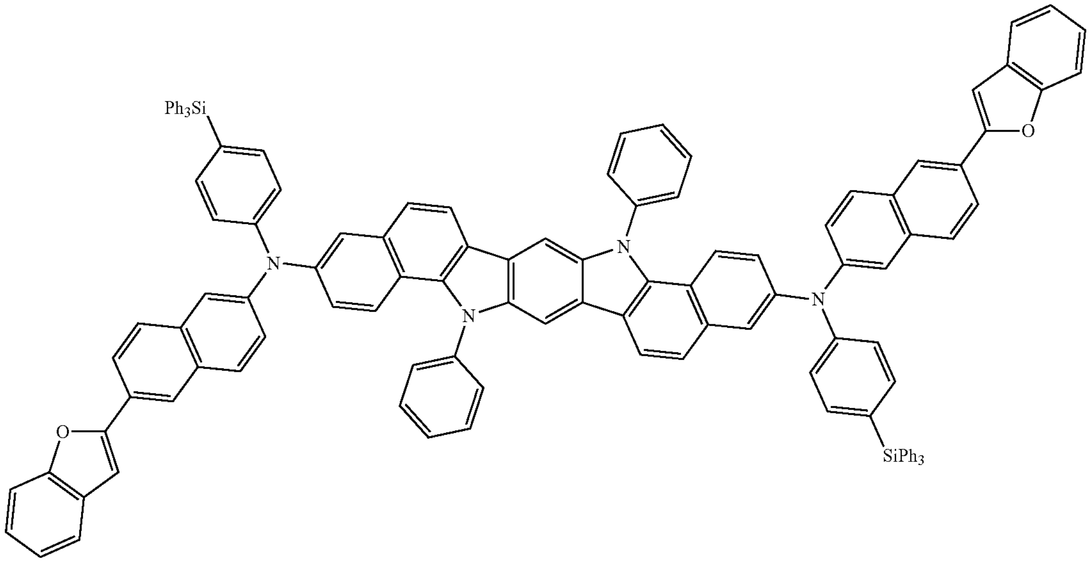

-continued
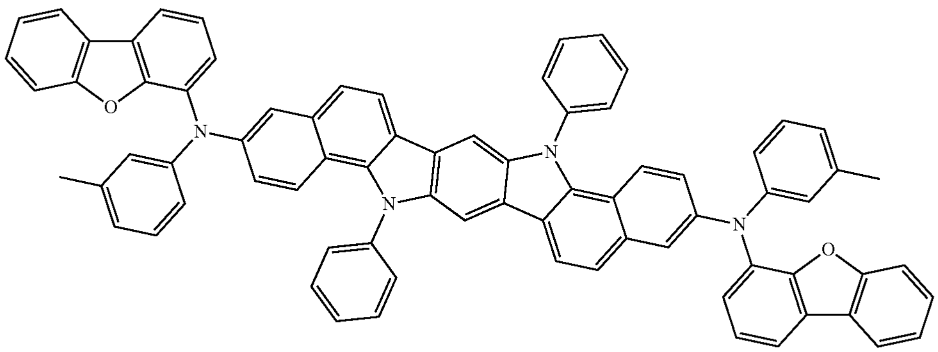
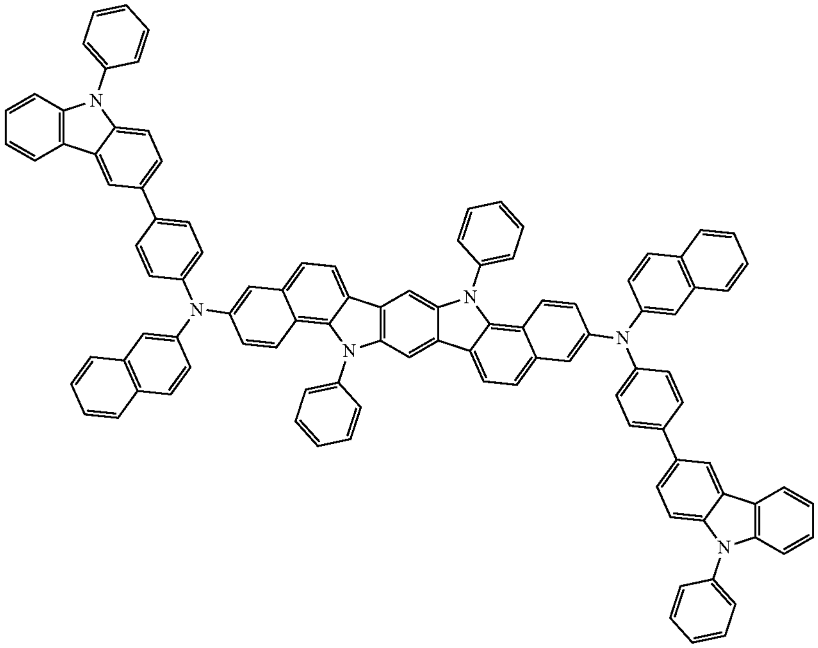
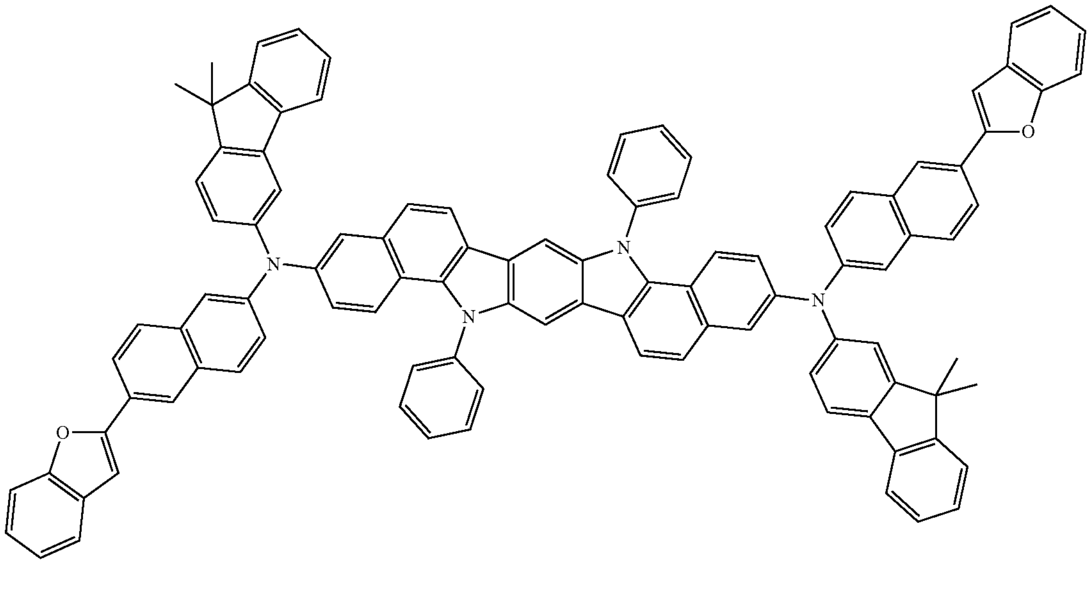

-continued
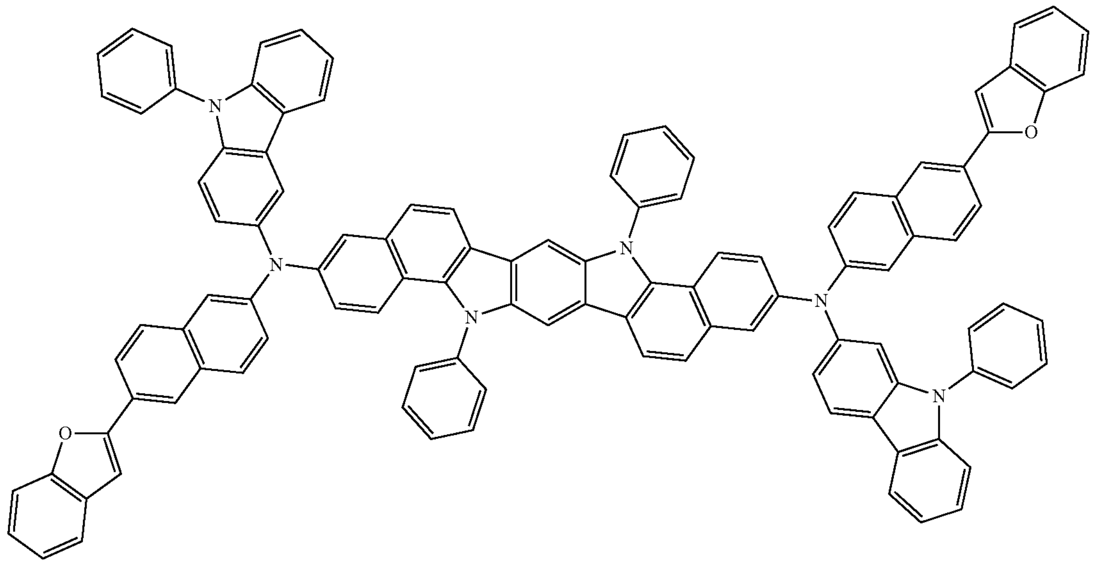
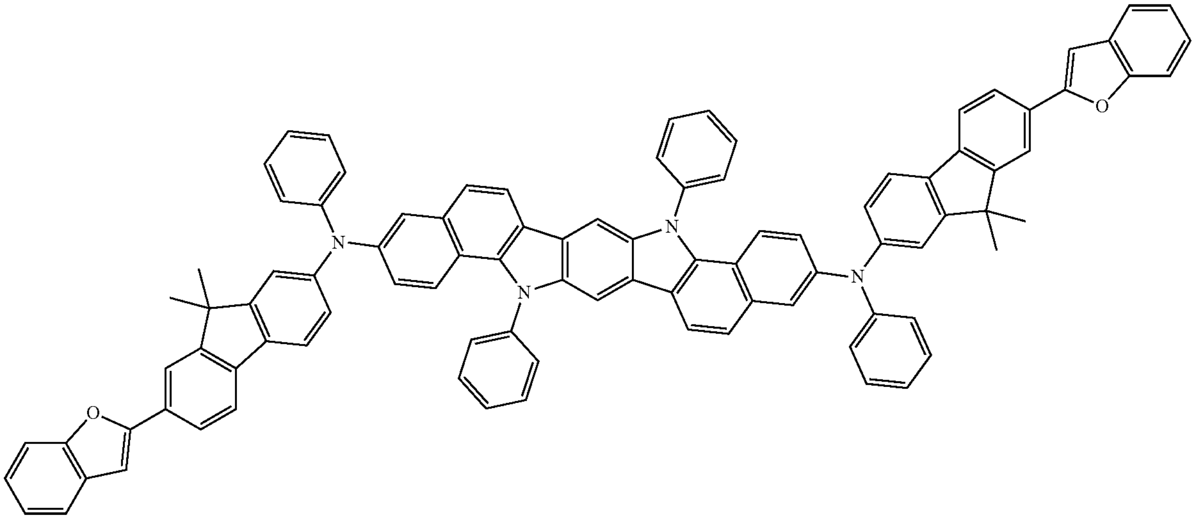
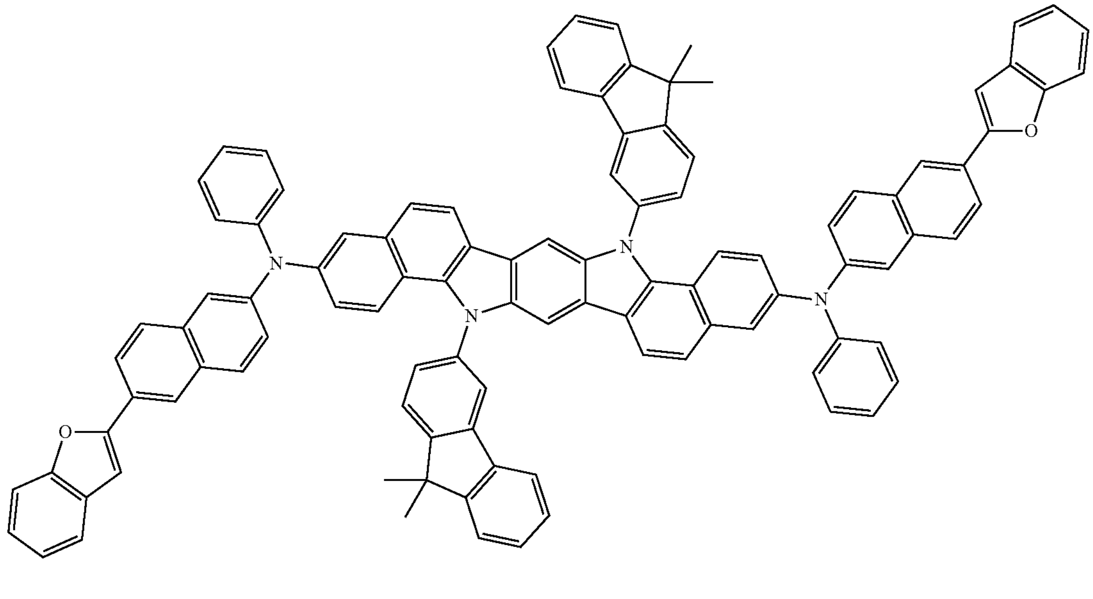

-continued
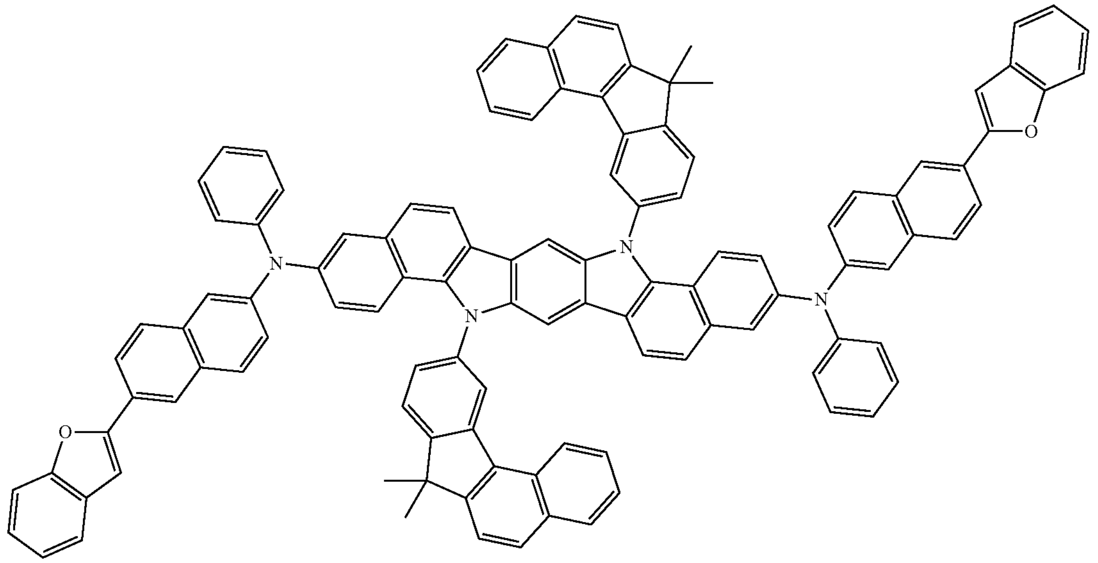
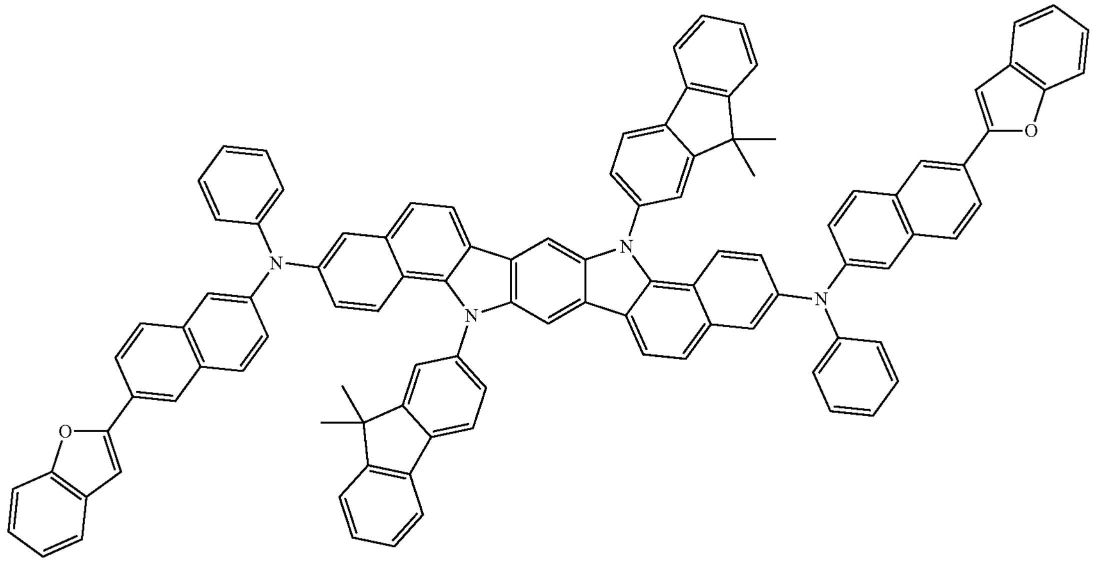
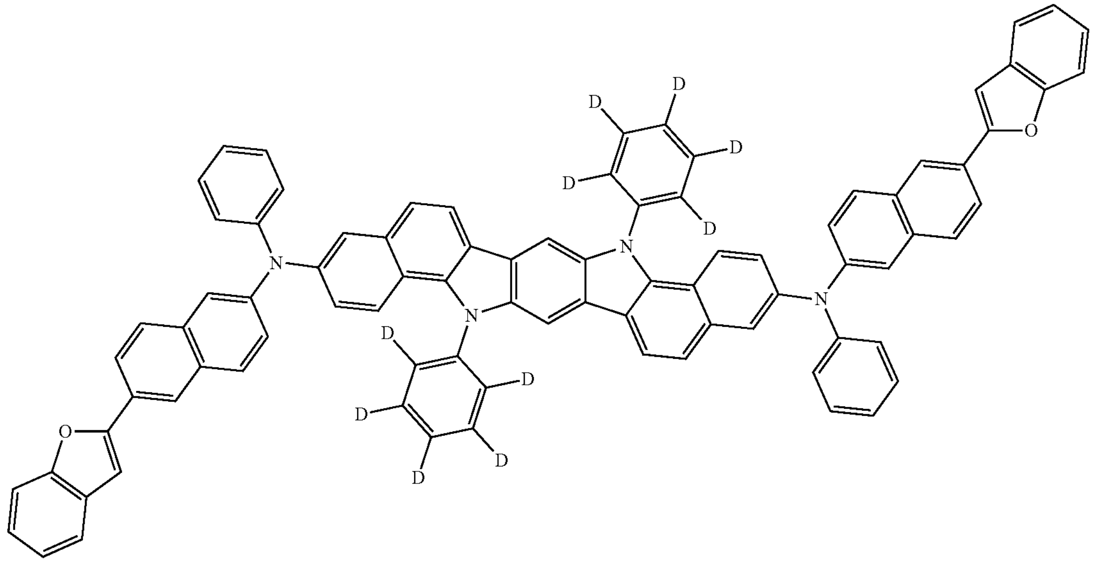

-continued
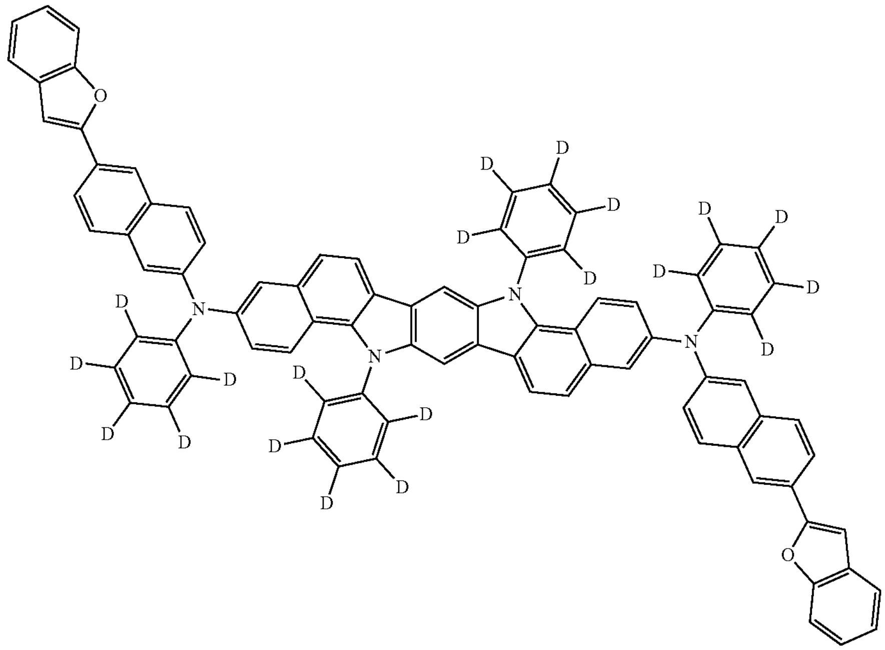
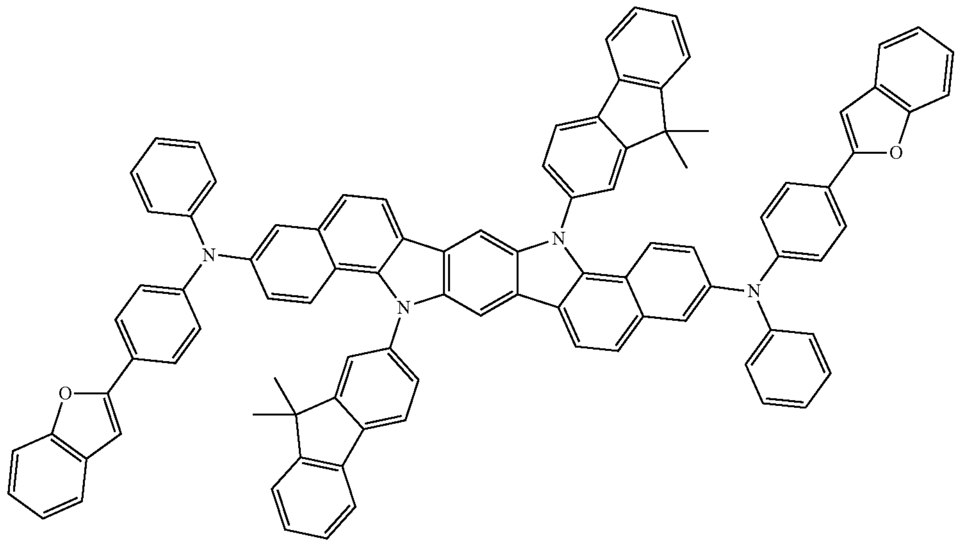

-continued
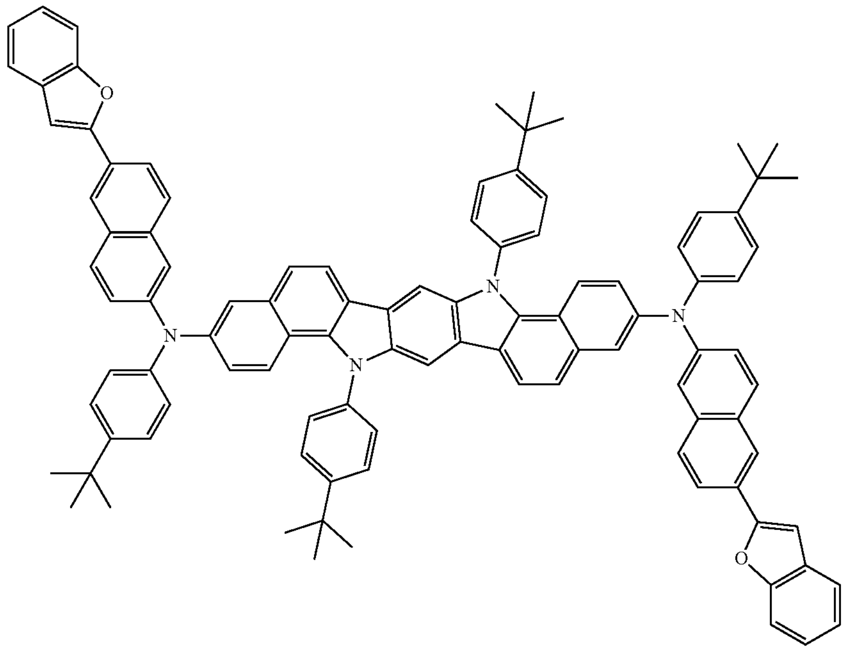
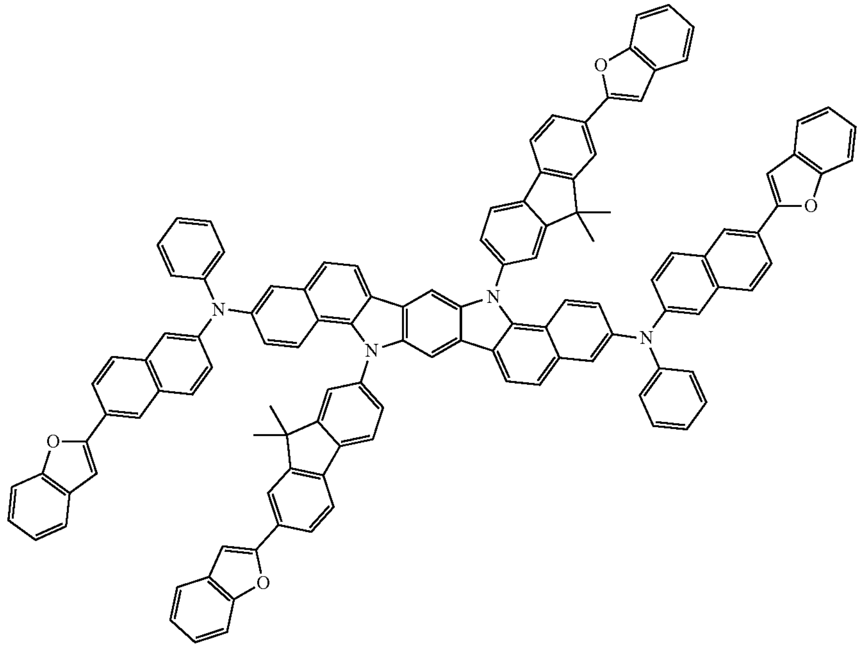

-continued
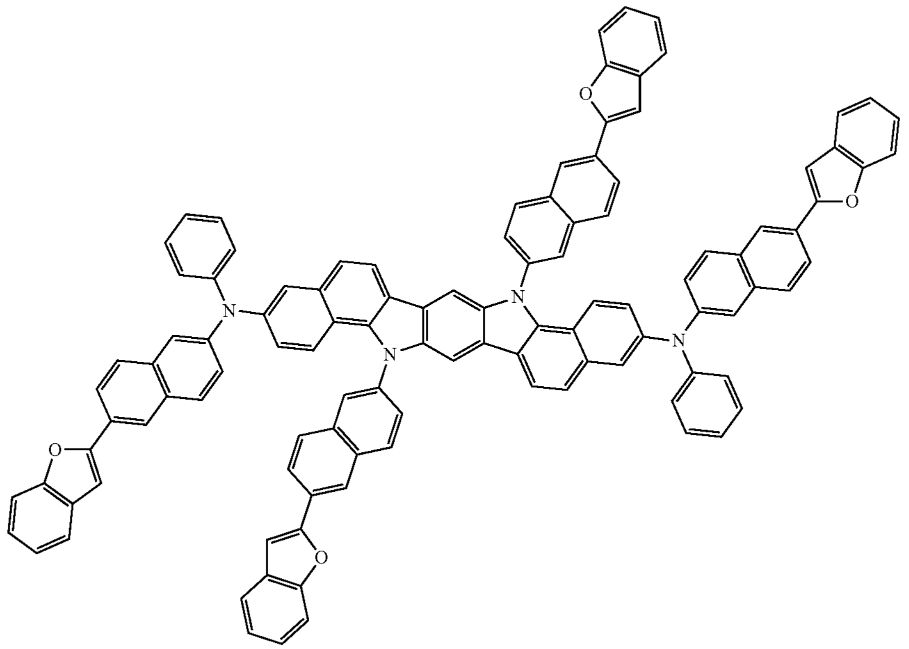
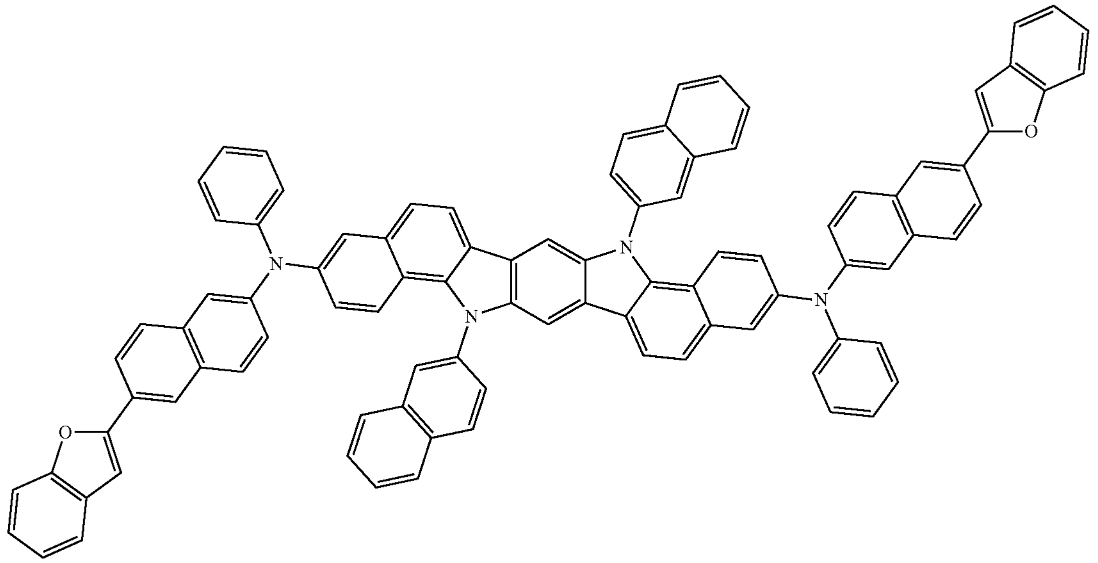
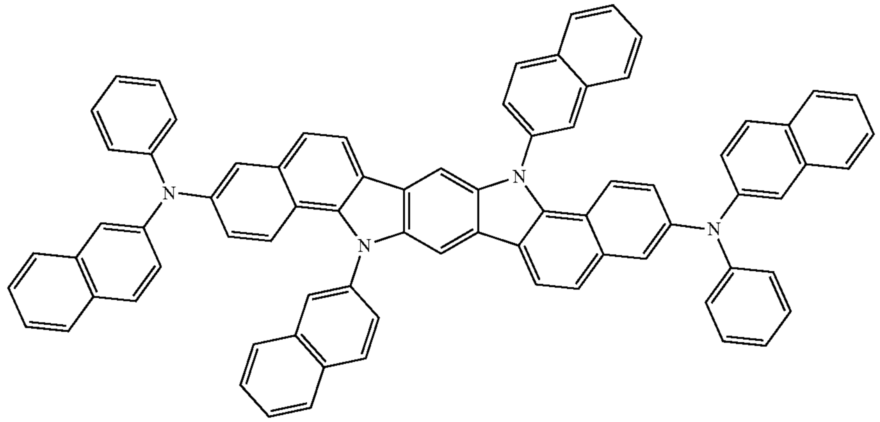

-continued
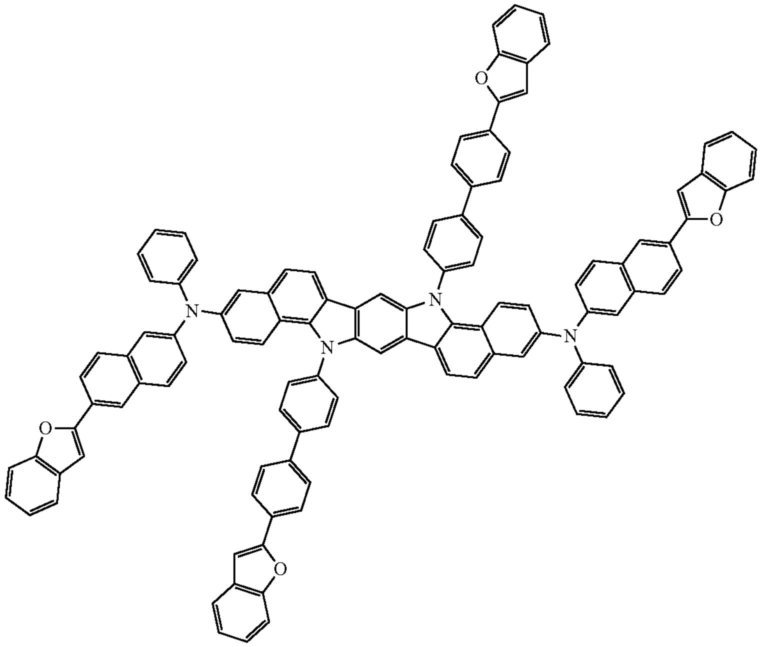
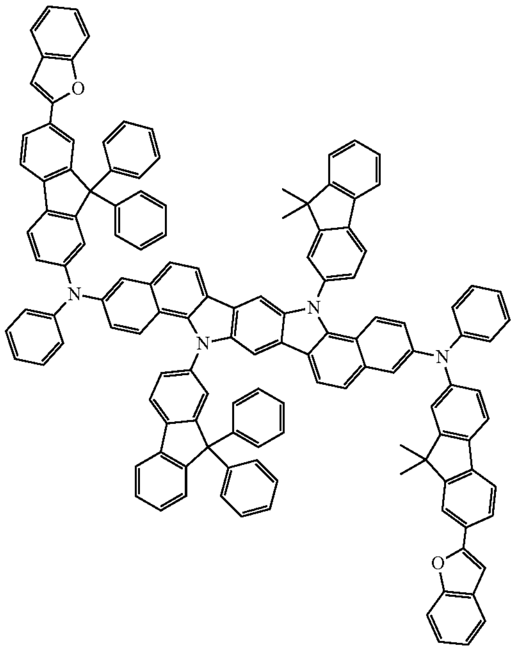

-continued
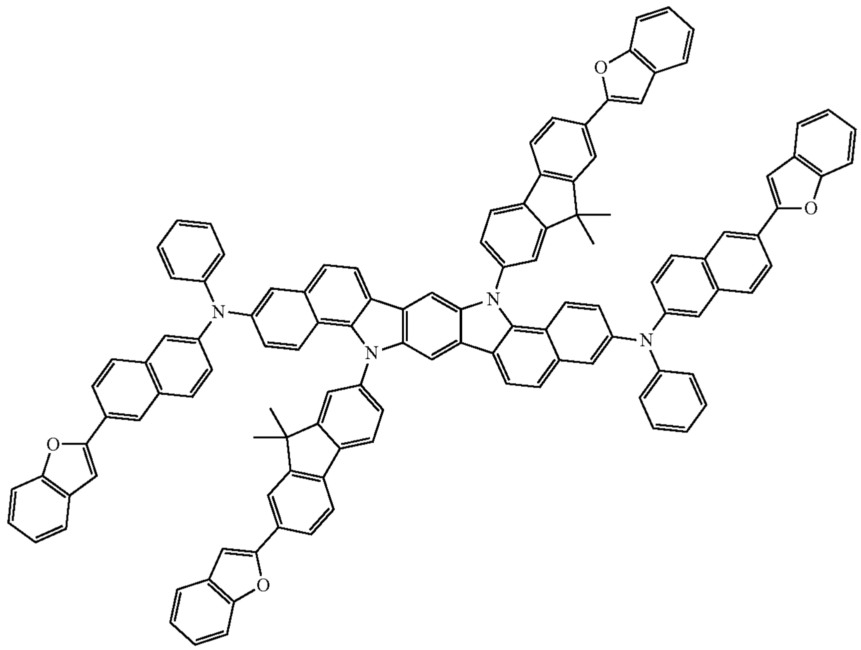
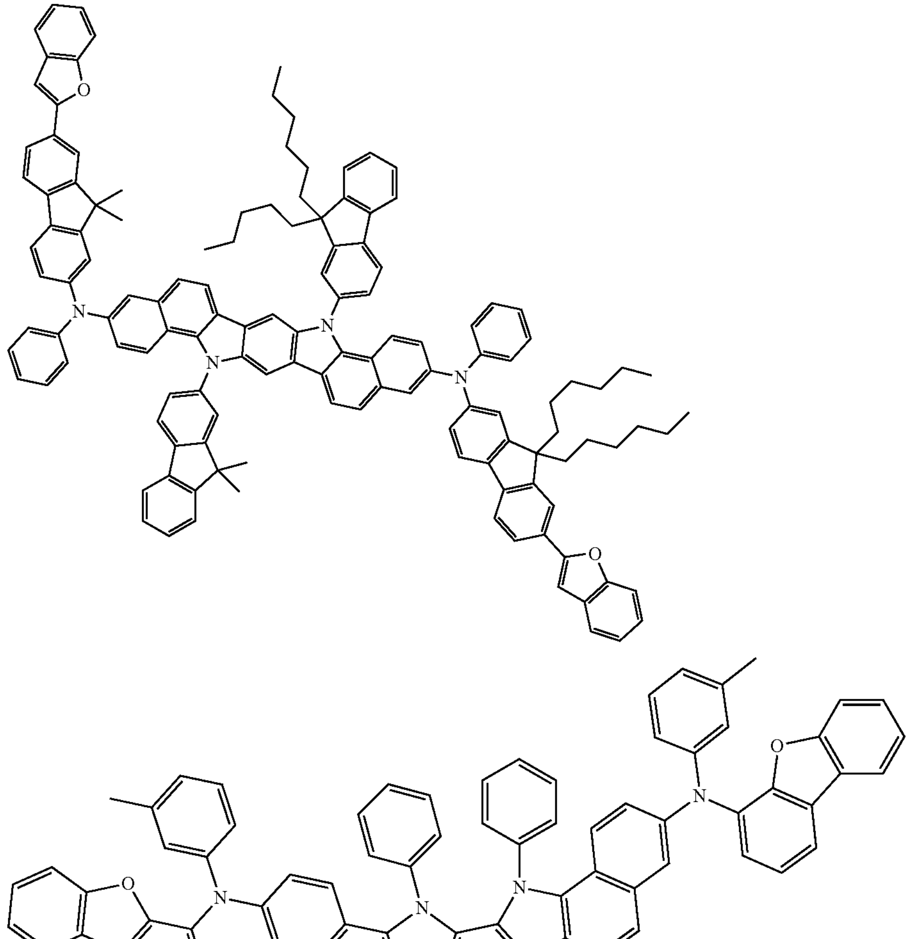
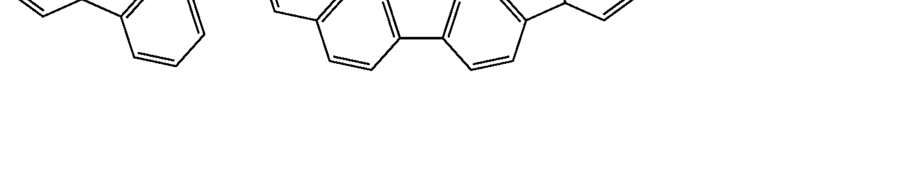

-continued
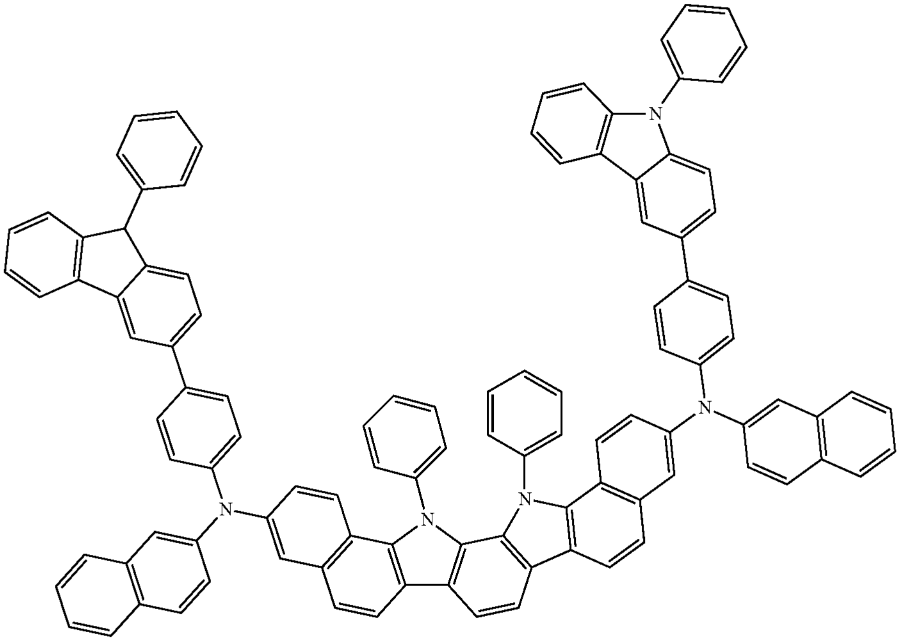
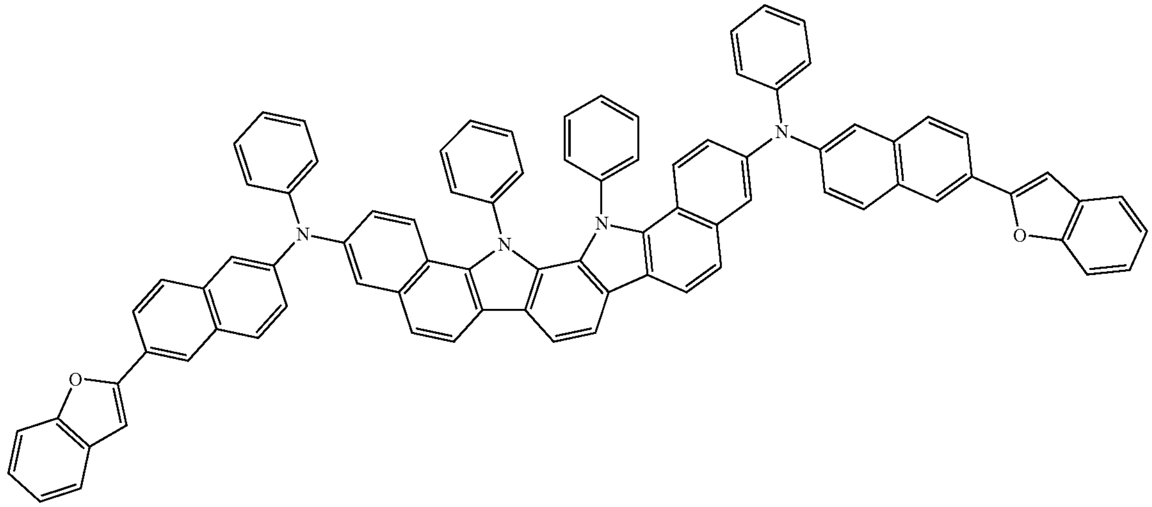
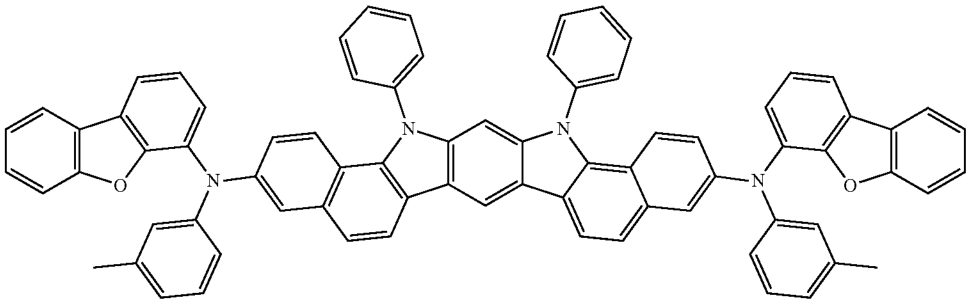

-continued

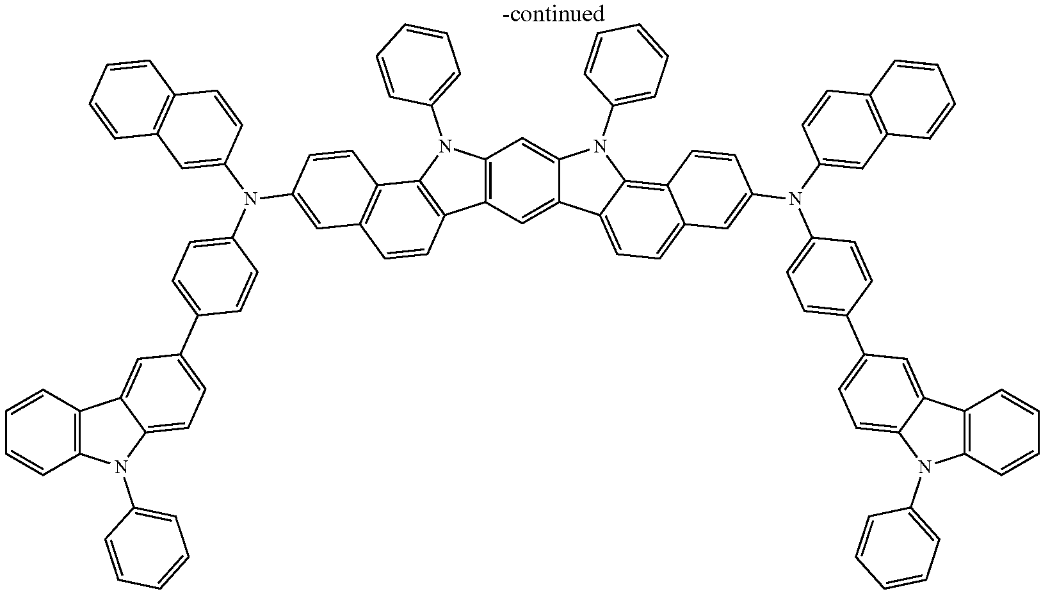

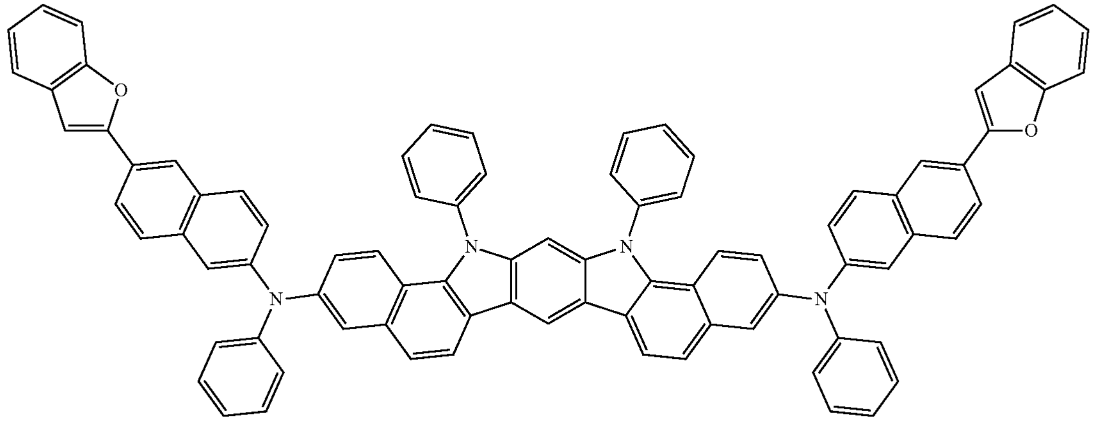 [SMILES: c1ccc(N(c2ccc3cc(-c4cc5ccccc5o4)ccc3c2)c2ccc3c(ccc4c5cc6c7ccc8cc(N(c9ccccc9)c9ccc%10cc(-c%11cc%12ccccc%12o%11)ccc%10c9)ccc8c7n(-c7ccccc7)c6cc5n(-c5ccccc5)c34)c2)cc1]

Meanwhile, the compound represented by Chemical Formula 1 may be prepared, for example, by a preparation method as shown in the following Reaction Scheme 1.

[Reaction Scheme 1]

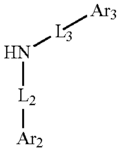

SM1

+

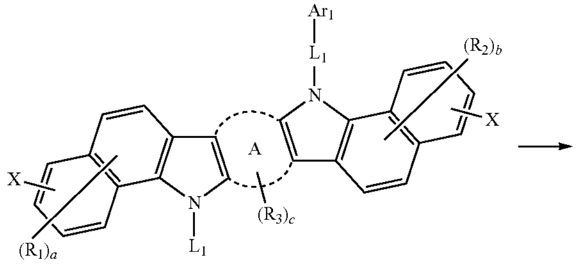

SM2

-continued

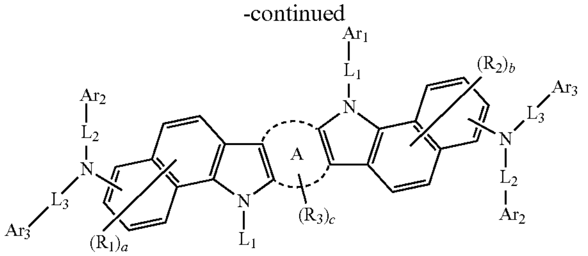

1 wherein in Reaction Scheme 1, each X may be independently halogen, preferably bromo, or chloro, and the definitions of other substituents are the same as described above.

Specifically, the compound represented by Chemical Formula 1 is prepared by combining the starting materials SM1 and SM2 through an amine substitution reaction. The amine substitution reaction is preferably carried out in the presence of a palladium catalyst and a base, and a reactive group for the amine substitution reaction can be appropriately modified, and the method for preparing the compound represented by Chemical Formula 1 may be further embodied in Preparation Examples described hereinafter.

(Coating Composition)

Meanwhile, the compound according to the present disclosure can form an organic material layer, particularly a light emitting layer of an organic light emitting device by a solution process. Specifically, the compound may be used as a dopant material of the light emitting layer. For this purpose, the present disclosure provides a coating composition including the above-mentioned compound according to the present disclosure and a solvent.

The solvent is not particularly limited as long as it is a solvent capable of dissolving or dispersing the compound according to the present disclosure. Examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene, mesitylene, 1-methylnaphthalene, and 2-methylnaphthalene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, and cyclohexanone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; benzoate-based solvents such as butylbenzoate, methyl-2-methoxybenzoate and ethylbenzoate; phthalate-based solvents such as dimethyl phthalate, diethyl phthalate, and diphenyl phthalate; tetraline; 3-phenoxy-toluene, and the like. In addition, the above-mentioned solvents may be used singly or in combination of two or more solvents. Preferably, ethyl benzoate may be used as the solvent Further, the coating composition may further include a compound used as a host material, and a description of the compound used for the host material will be given later.

Further, the viscosity of the coating composition is preferably 1 cP to 10 cP, and coating is made easy within the above range. Further, in the coating composition, the concentration of the compound according to the present disclosure may be preferably 0.1 wt/v % to 20 wt/v %.

Further, the solubility (wt %) of the compound represented by Chemical Formula 1 at normal temperature/normal pressure may be 0.1 wt % or more based on the solvent cyclohexanone. Thereby, the coating composition including the compound represented by Chemical Formula 1 and the solvent may be used in a solution process.

In another embodiment of the present disclosure, there is provided a method for forming a light emitting layer using the above-mentioned coating composition. Specifically, the method includes the steps of: coating the above-mentioned coating composition according to the present disclosure on the anode or on the hole transport layer formed on the anode by a solution process; and heat-treating the coated coating composition.

The solution process uses the above-mentioned coating composition according to the present disclosure, and refers to spin coating, dip coating, doctor blading, inkjet printing, screen printing, spraying, roll coating, and the like, but is not limited thereto.

The heat treatment temperature in the heat treatment step is preferably from 150 to 230° C. Further, a heat treatment time may be from 1 minute to 3 hours, more preferably 10 minutes to 1 hour. Further, the heat treatment is preferably carried out in an inert gas atmosphere such as argon and nitrogen.

(Organic Light Emitting Device)

In another embodiment of the present disclosure, there is provided an organic light emitting device including the compound represented by Chemical Formula 1. In one example, the present disclosure provides an organic light emitting device comprising: a first electrode; a second electrode that is provided opposite to the first electrode; and a light emitting layer that is provided between the first electrode and the second electrode, wherein the light emitting layer includes the compound represented by Chemical Formula 1.

Further, the organic light emitting device according to the present disclosure may be a normal type organic light emitting device in which an anode, one or more organic material layers and a cathode are sequentially stacked on a substrate wherein the first electrode is an anode, and the second electrode is a cathode. Further, the organic light emitting device according to the present disclosure may be an inverted type organic light emitting device in which a cathode, one or more organic material layers and an anode are sequentially stacked on a substrate wherein the first electrode is a cathode and the second electrode is an anode. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by Chemical Formula 1 may be included in the light emitting layer.

FIG. 2 shows an example of an organic light emitting device comprising a substrate 1, an anode 2, a hole injection layer 5, a hole transport layer 6, a light emitting layer 3, an electron injection and transport layer 7, and a cathode 4. In such a structure, the compound represented by Chemical Formula 1 may be included in the light emitting layer.

The organic light emitting device according to the present disclosure may be manufactured by using materials and methods known in the art, except that the light emitting layer includes the compound according to the present disclosure, and is manufactured by the above-mentioned method.

For example, the organic light emitting device according to the present disclosure can be manufactured by sequentially stacking an anode, an organic material layer and a cathode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon.

In addition to such a method, the organic light emitting device may be manufactured by sequentially depositing a cathode material, an organic material layer and an anode material on a substrate (International Publication WO2003/012890). However, the manufacturing method is not limited thereto.

In one example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. As the hole transport material, the compound represented by Chemical Formula 1 may be used, or an arylamine-based organic material, a conductive polymer, a block copolymer in which a conjugate portion and a non-conjugate portion are present together, and the like, but are not limited thereto.

Meanwhile, the organic light emitting device may be provided with an electron inhibition layer between the hole transport layer and the light emitting layer. The electron inhibition layer refers to a layer which is formed on the hole transport layer, and preferably, is provided in contact with the light emitting layer, and thus serves to control hole mobility, to prevent excessive movement of electrons, and to increase the probability of hole-electron bonding, thereby improving the efficiency of the organic light emitting device. The electron inhibition layer includes an electron blocking material, and as an example of such an electron blocking material, a compound represented by the Chemical Formula 1 may be used, or an arylamine-based organic material or the like may be used, but is not limited thereto.

The light emitting layer may include a host material and a dopant material. As the dopant material, the above-mentioned compound represented by Chemical Formula 1 can be used. Also, the host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Meanwhile, the organic light emitting device may be provided with a hole blocking layer between the light emitting layer and the electron transport layer. The hole blocking layer refers to a layer which is formed on the light emitting layer, and preferably, is provided in contact with the light emitting layer, and thus severs to control electron mobility, to prevent excessive movement of holes, and to increase the probability of hole-electron bonding, thereby improving the efficiency of the organic light emitting device. The hole blocking layer includes a hole blocking material, and as an example of such hole blocking material, a compound into which an electron-withdrawing group is introduced, such as azine derivatives including triazine; triazole derivatives; oxadiazole derivatives; phenanthroline derivatives; phosphine oxide derivatives can be used, but is not limited thereto.

The electron injection and transport layer is a layer for simultaneously performing the roles of an electron transport layer and an electron injection layer that inject electrons from an electrode and transport the received electrons up to the light emitting layer, and is formed on the light emitting layer or the hole blocking layer. The electron injection and transport material is suitably a material which can receive electrons well from a cathode and transfer the electrons to a light emitting layer, and has a large mobility for electrons. Specific examples of the electron injection and transport material include: an Al complex of 8-hydroxyquinoline; a complex including $Alq_3$; an organic radical compound; a hydroxyflavone-metal complex, a triazine derivative, and the like, but are not limited thereto. Alternatively, it may be used together with fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

The electron injection and transport layer may also be formed as a separate layer such as an electron injection layer and an electron transport layer. In such a case, the electron transport layer is formed on the light emitting layer or the hole blocking layer, and the above-mentioned electron injection and transport material may be used as the electron transport material included in the electron transport layer. In addition, the electron injection layer is formed on the electron transport layer, and examples of the electron injection material included in the electron injection layer include LiF, NaCl, CsF, $Li_2O$, BaO, fluorenone, anthraquinodimethane, diphenoquinone, thiopyran dioxide, oxazole, oxadiazole, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound according to the present disclosure may be included in an organic solar cell or an organic transistor in addition to an organic light emitting device.

The preparation of the compound represented by Chemical Formula 1 and the organic light emitting device including the same will be described in detail in the following examples. However, these examples are presented for illustrative purposes only, and are not intended to limit the scope of the present disclosure.

Preparation Example 1: Preparation of Compound 1

Step 1-1: Synthesis of Intermediate Compound 1-c

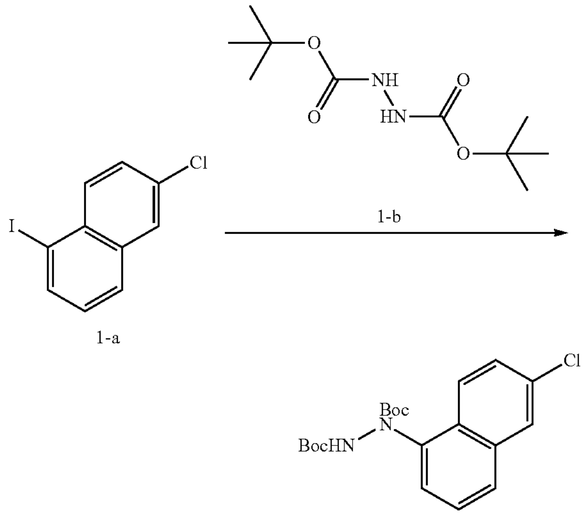

1-a 1-b 1-c

Compound 1-a (1.0 eq.), Compound 1-b (1.03 eq.), $Cs_2CO_3$ (1.4 eq.) and $P(t\text{-}Bu)_3HBF_4$ (10 mol %) were placed in a round bottom flask filled with $N_2$ (g), and dissolved in anhydrous toluene. After raising the bath temperature to 110° C., $Pd(OAc)_2$ (5 mol %) was added dropwise thereto, and the mixture was stirred for 4 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 1-c (yield: 81%).

m/z $[M+H]^+$=393.

Step 1-2: Synthesis of Intermediate Compound 1-e

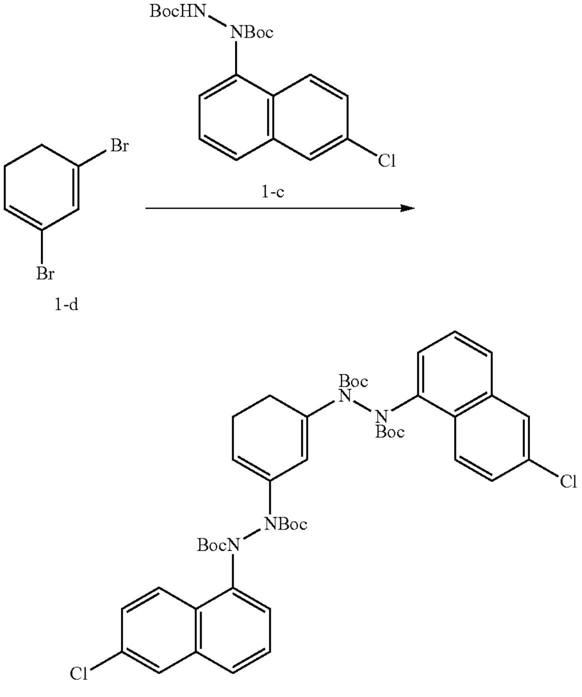

1-c 1-d 1-e

Compound 1-d (1.0 eq.), Compound 1-c (2.2 eq.), Cs2CO3 (2.2 eq.) and $P(t\text{-}Bu)_3 \cdot HBF_4$ (20 mol %) were placed in a round bottom flask filled with $N_2$ (g), and dissolved in anhydrous toluene. After raising the bath temperature to 110° C., $Pd(OAc)_2$ (10 mol %) was added dropwise thereto, and the mixture was stirred overnight. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 1-e (yield: 93%).

m/z $[M+H]^+$=861.

Step 1-3: Synthesis of Intermediate Compound 1-f

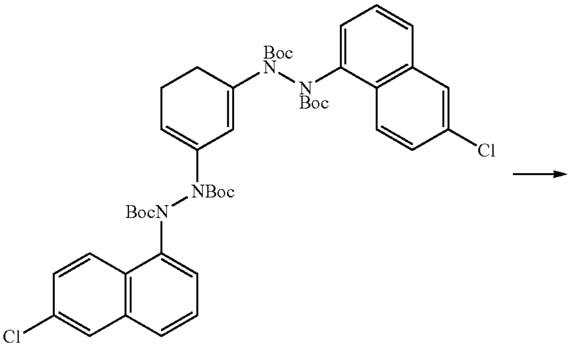

1-e

-continued

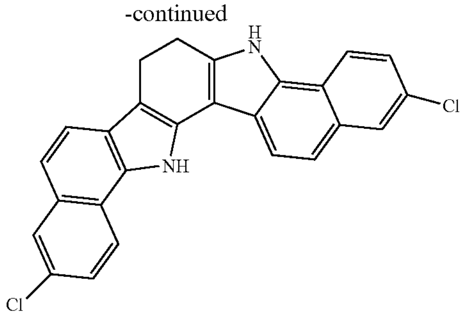

1-f

Compound 1-e (1.0 eq.) and $ZnCl_2$ (2.2 eq.) were placed in a round bottom flask filled with $N_2$ (g), and dissolved in anhydrous 1,4-dioxane. After raising the bath temperature to 90° C., the mixture was stirred for 1 hour. After the reaction, saturated aqueous $Na_2CO_3$ was added dropwise to terminate the reaction, and the reaction mixture was washed with dichloromethane and water, the organic layer was separated. Water was removed with $MgSO_4$, and passed through a celite-silica pad. The passed solution was concentrated under reduced pressure, and then purified by column chromatography to obtain Intermediate Compound 1-f (yield: 89%).

m/z $[M+H]^+$=427.

Step 1-4: Synthesis of Intermediate Compound 1-g

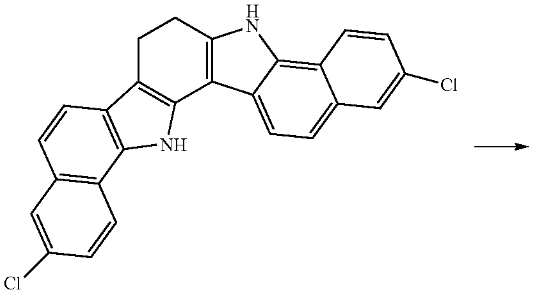

1-f

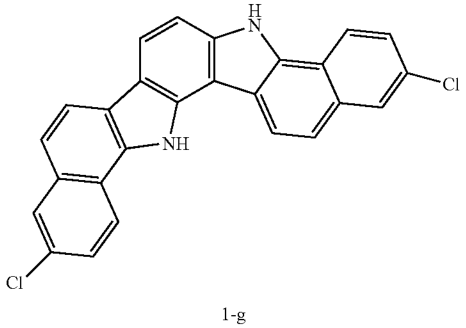

1-g

Compound 1-f (1.0 eq.) and DDQ (2,3-dichloro-5,6-dicyano-p-benzoquinone, 6.0 eq.) were placed in a round bottom flask filled with $N_2$ (g), and dissolved in anhydrous benzene. The reaction solution was stirred at room temperature for 24 hours. After the reaction, the solvent was removed under reduced pressure, and $K_2CO_3$ (6.0 eq.), MeOH, and $H_2O$ were added dropwise to the reaction mixture. After raising the bath temperature to 60° C., the reaction solution was stirred for 30 minutes. After the reaction, the precipitate was washed with MeOH and $H_2O$ and filtered to obtain a filter cake. A sufficiently dried filter cake was added to 1,2-dichlorobenzene and dissolved under heating. The dissolved reaction product was passed through a celite-silica pad. An excess of n-hexane was added dropwise to the passed solution to precipitate the product. The precipitate was washed with n-hexane and MeOH and filtered to obtain a filter cake, which was sufficiently dried to synthesize Compound 1-g (yield: 76%).

m/z $[M+H]^+$=425.

Step 1-5: Synthesis of Intermediate Compound 1-i

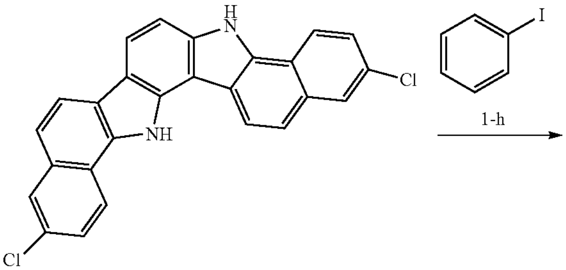

1-g

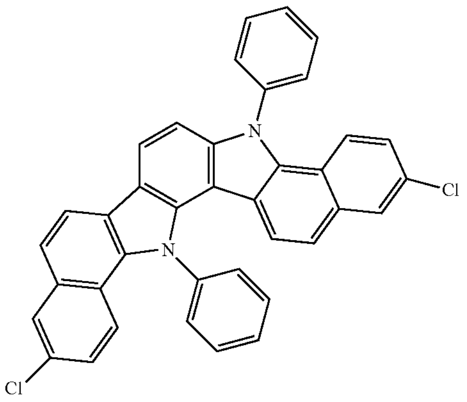

1-i

Compound 1-g (1.0 eq.) and NaOt-Bu (6.05 eq.) were placed in a round bottom flask and dissolved in anhydrous PhMe (0.03 M). Compound 1-h (7.1 eq.) was added dropwise to the reaction solution. $Pd(P(t-Bu)_3)_2$ (20 mol %) was added dropwise to the reaction solution under a bath temperature of 110° C., and the mixture was stirred for 22 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 1-i (yield: 89%).

m/z $[M+H]^+$=577.

Step 1-6: Synthesis of Intermediate Compound 1-l

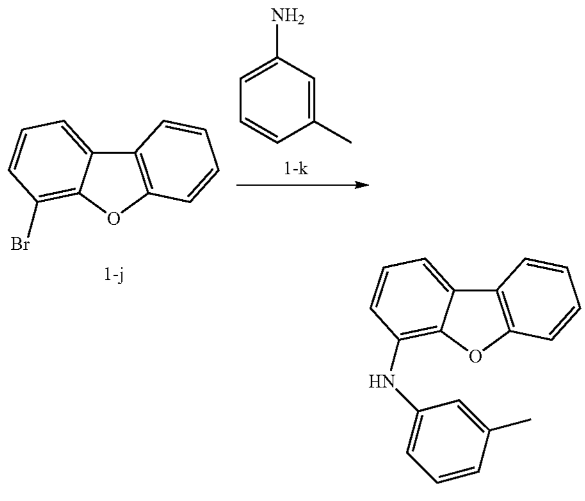

1-j 1-k 1-l

Compound 1-j (1.0 eq.), Compound 1-k (1.2 eq.) and NaOt-Bu (2.0 eq.) were placed in a round bottom flask and dissolved in anhydrous toluene. After raising the bath temperature to 110° C., $Pd((t\text{-}Bu)_3P)_2$ (3 mol %) was added dropwise thereto, and the mixture was stirred for 4 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 1-l (yield: 81%).

m/z $[M+H]^+$=274.

Step 1-7: Synthesis of Compound 1

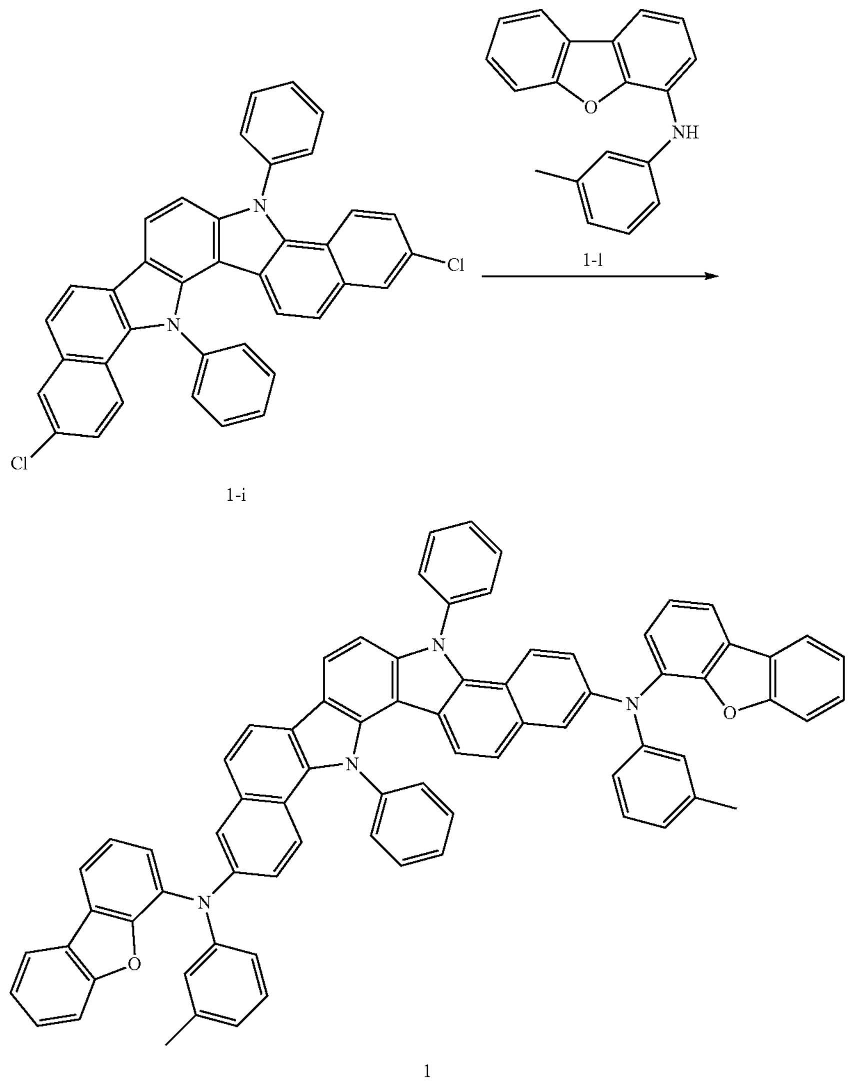

1-l 1-i

1

Compound 1-i (1.0 eq.), Compound 1-l (2.2 eq.), P(t-Bu)$_3$HBF$_4$ (10 mol %), and NaOt-Bu (2.2 eq.) were placed in a round bottom flask and dissolved in anhydrous PhMe (0.02 M). $Pd_2(dba)_3$ (5 mol %) was added dropwise to the reaction solution under a bath temperature of 105° C., and the mixture was stirred overnight. After the reaction, the reaction mixture was stirred and then cooled to room temperature. An excess of n-hexane was added dropwise to the reaction mixture to precipitate the product. The precipitate was washed with MeOH and $H_2O$ and filtered to obtain a filter cake. A sufficiently dried filter cake was added to 1,2-dichlorobenzene and dissolved under heating. The dissolved reaction product was passed through a celite-silica pad. An excess of n-hexane was added dropwise to the passed solution to precipitate the product. The precipitate was washed with n-hexane and MeOH and filtered to obtain a filter cake, which was sufficiently dried to prepare Compound 1 (yield: 64%).

m/z $[M+H]^+$=1051.

Preparation Example 2: Preparation of Compound 2

Step 2-1: Synthesis of Intermediate Compound 2-b

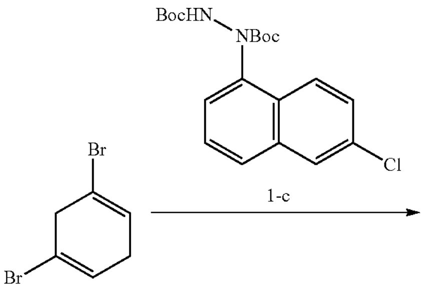

1-c 2-a

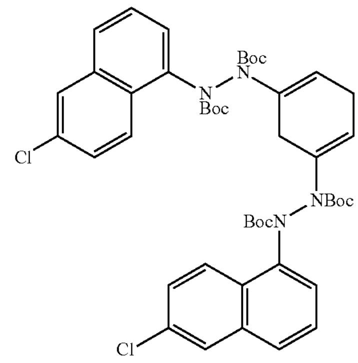

2-b

Compound 2-b (yield: 71%) was prepared in the same manner as in step 1-2, except that Compound 2-a was used instead of Compound 1-d.

m/z $[M+H]^+$=861

Step 2-2: Synthesis of Intermediate Compound 2-c

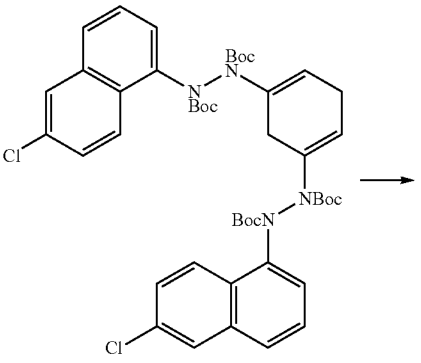

2-b

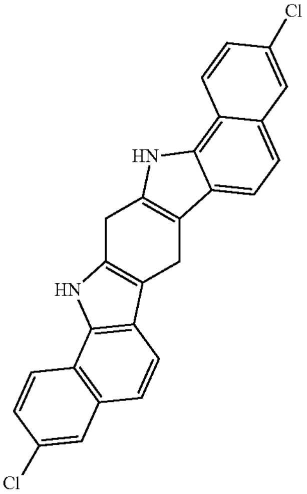

2-c

Compound 2-c (yield: 73%) was prepared in the same manner as in step 1-3, except that Compound 2-b was used instead of Compound 1-e.

m/z $[M+H]^+$=427

Step 2-3: Synthesis of Intermediate Compound 2-d

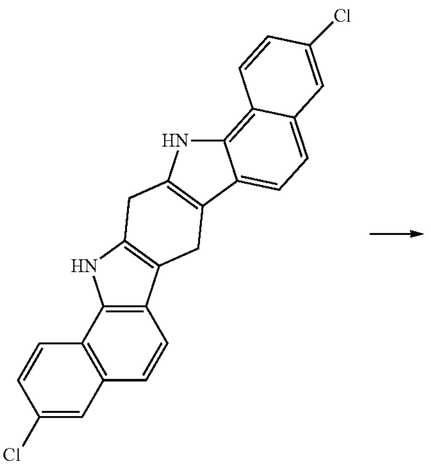

2-c

-continued

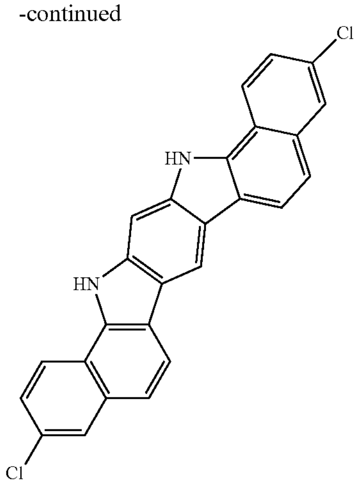

2-d

Compound 2-d (yield: 78%) was prepared in the same manner as in step 1-4, except that Compound 2-c was used instead of Compound 1-f.

m/z $[M+H]^+$=425

Step 2-4: Synthesis of Intermediate Compound 2-e

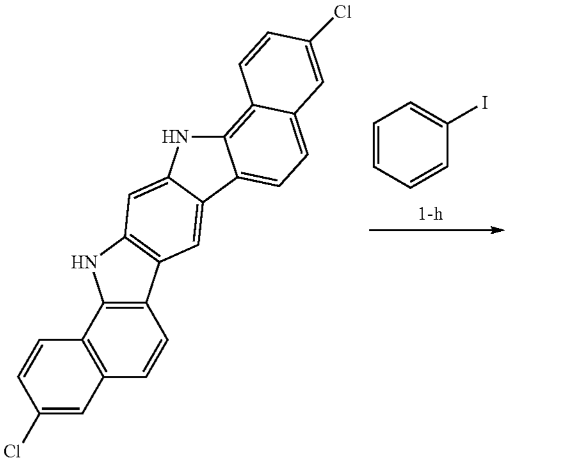

2-d

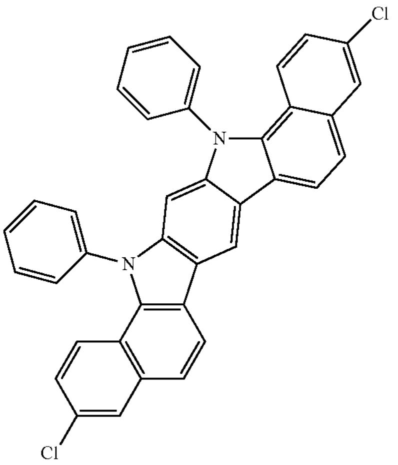

2-e

Compound 2-e (yield: 91%) was prepared in the same manner as in step 1-5, except that Compound 2-d was used instead of Compound 1-g.

m/z $[M+H]^+$=577

Step 2-5: Synthesis of Compound 2

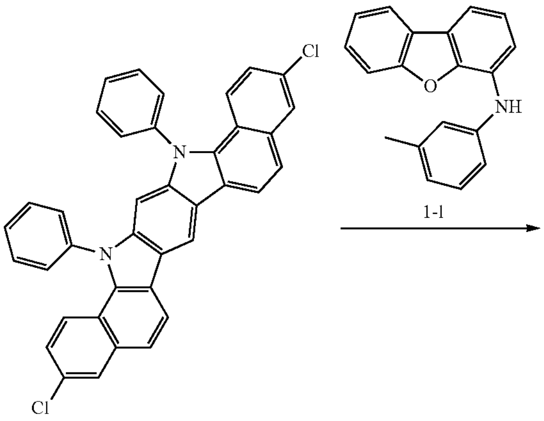

2-e

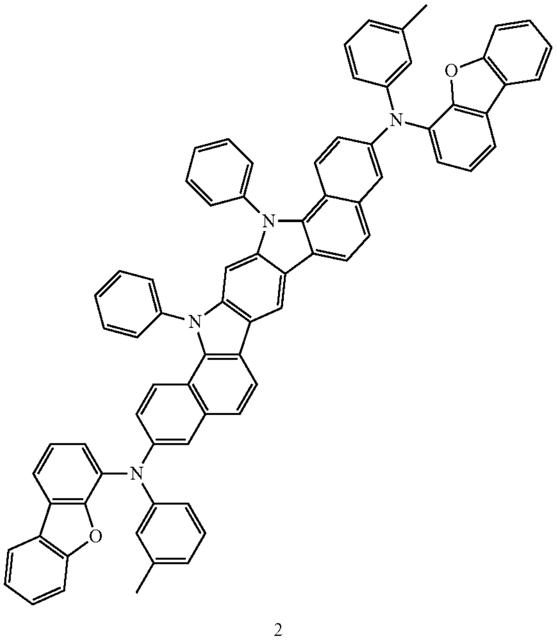

2

Compound 2 (yield: 67%) was prepared in the same manner as in step 1-7, except that Compound 2-e was used instead of Compound 1-i.

m/z $[M+H]^+$=1051

Preparation Example 3: Preparation of Compound 3

Step 3-1: Synthesis of Intermediate Compound 3-b

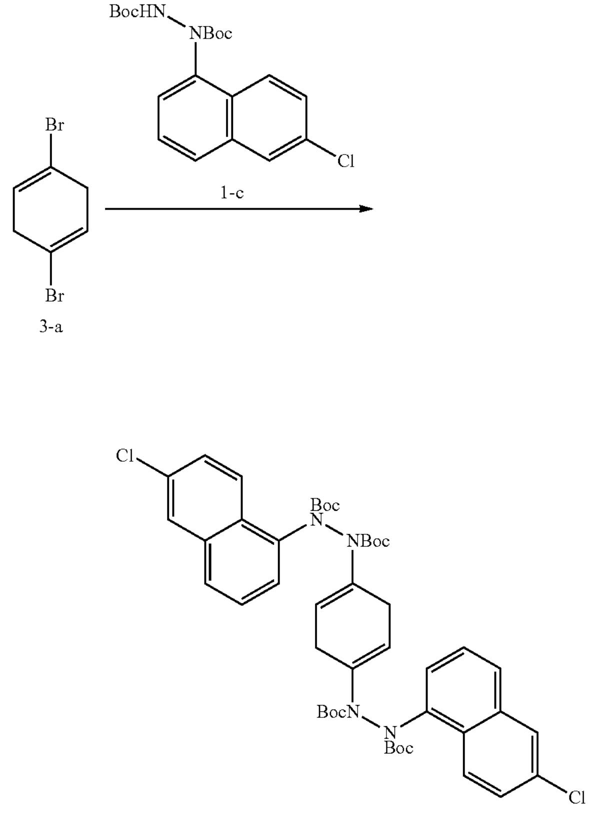

3-a 1-c 3-b

Compound 3-b (yield: 74%) was prepared in the same manner as in step 1-2, except that Compound 3-a was used instead of Compound 1-d.

m/z $[M+H]^+$=861

Step 3-2: Synthesis of Intermediate Compound 3-c

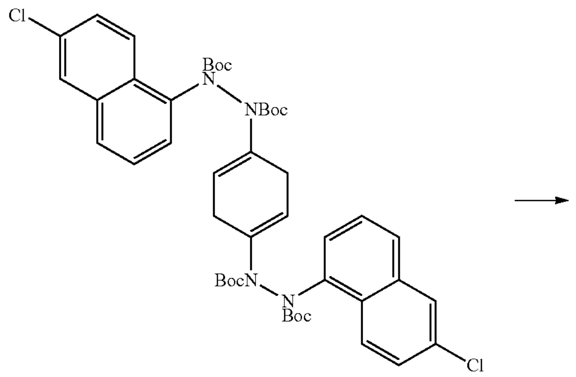

3-b

-continued

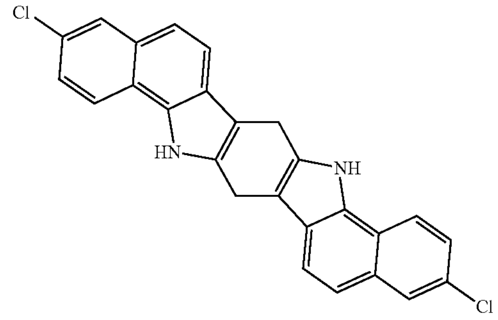

3-c

Compound 3-c (yield: 76%) was prepared in the same manner as in step 1-3, except that Compound 3-b was used instead of Compound 1-e.

m/z $[M+H]^+$=427

Step 3-3: Synthesis of Intermediate Compound 3-d

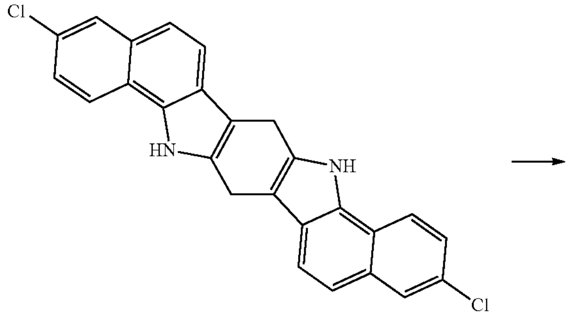

3-c

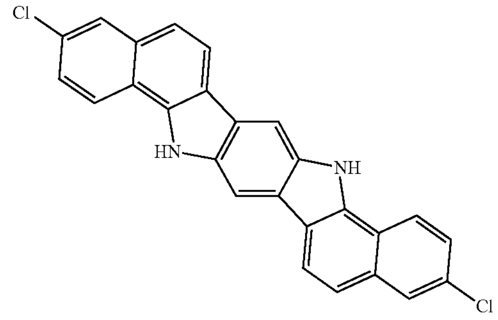

3-d

Compound 3-d (yield: 83%) was prepared in the same manner as in step 1-4, except that Compound 3-c was used instead of Compound 1-f.

m/z $[M+H]^+$=425

Step 3-4: Synthesis of Intermediate Compound 3-e
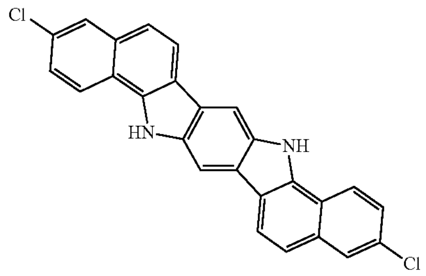
3-d
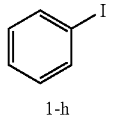
1-h
-continued
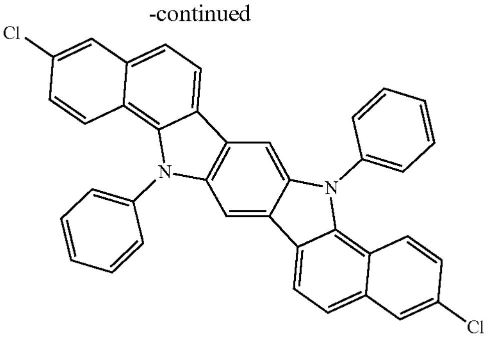
3-e
Compound 3-e (yield: 86%) was prepared in the same manner as in step 1-5, except that Compound 3-d was used instead of Compound 1-g.
m/z $[M+H]^+=577$
Step 3-5: Synthesis of Compound 3
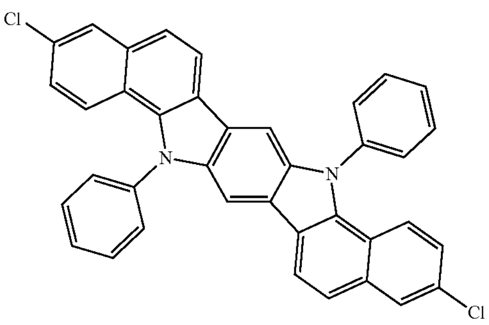
3-e
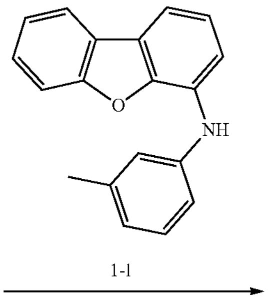
1-l
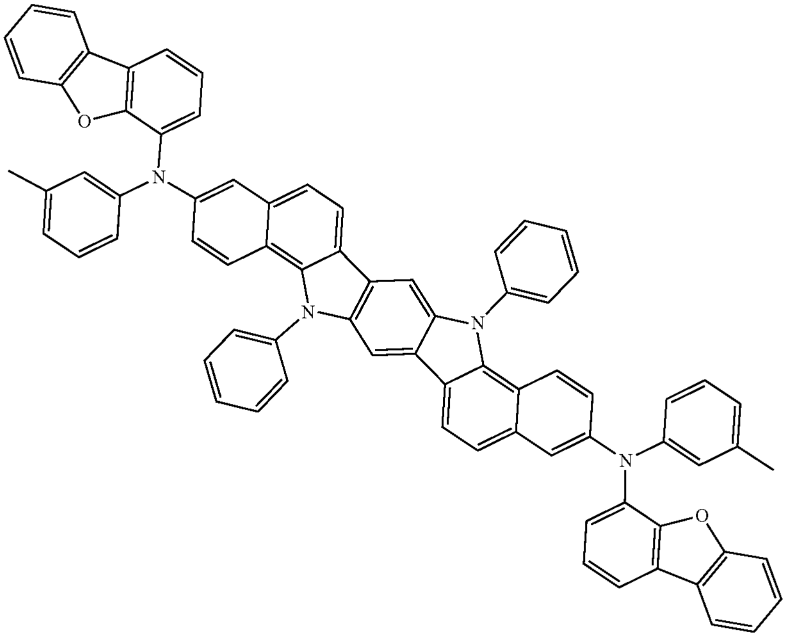
3

Compound 3 (yield: 74%) was prepared in the same manner as in step 1-7, except that Compound 3-e was used instead of Compound 1-i.

m/z $[M+H]^+$=1051

Preparation Example 4: Preparation of Compound 4

Step 4-1: Synthesis of Intermediate Compound 4-b

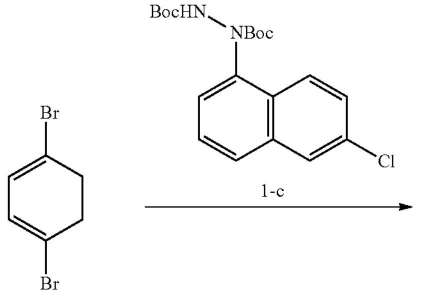

1-c 4-a

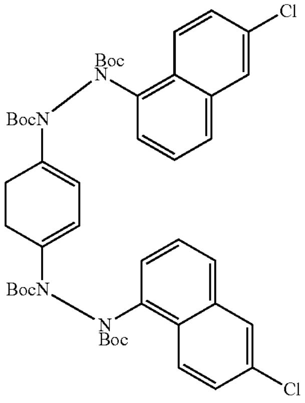

4-b

Compound 4-b (yield: 74%) was prepared in the same manner as in step 1-2, except that Compound 4-a was used instead of Compound 1-d.

m/z $[M+H]^+$=861

Step 4-2: Synthesis of Intermediate Compound 4-c

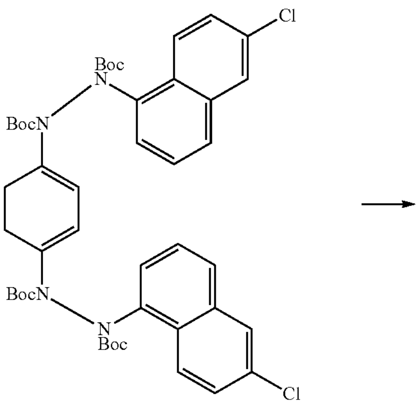

4-b

-continued

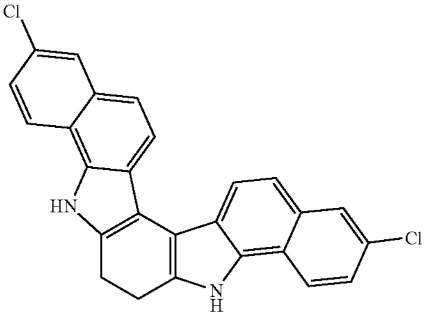

4-c

Compound 4-c (yield: 74%) was prepared in the same manner as in step 1-3, except that Compound 4-b was used instead of Compound 1-e.

m/z $[M+H]^+$=427

Step 4-3: Synthesis of Intermediate Compound 3-d

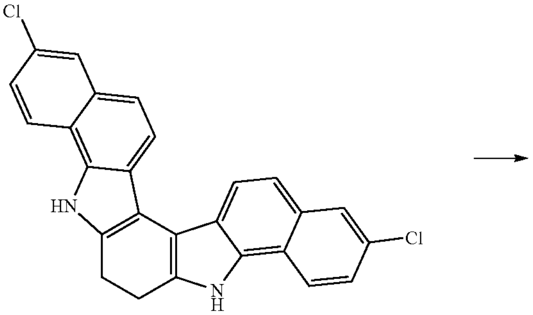

4-c

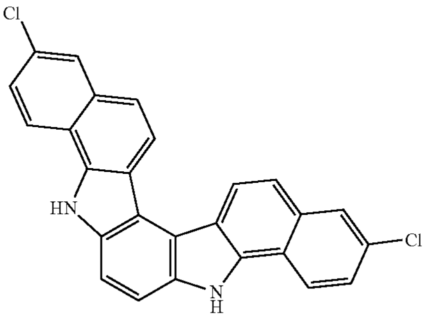

4-d

Compound 4-d (yield: 88%) was prepared in the same manner as in step 1-4, except that Compound 4-c was used instead of Compound 1-f.

m/z $[M+H]^+$=425

Step 4-4: Synthesis of Intermediate Compound 4-e

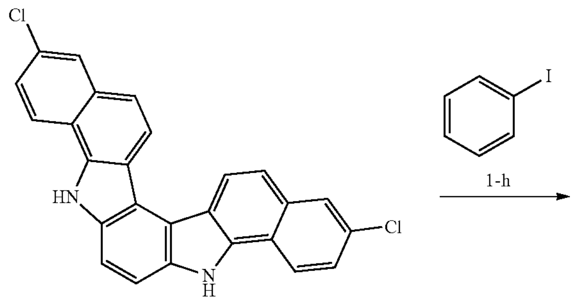

4-d

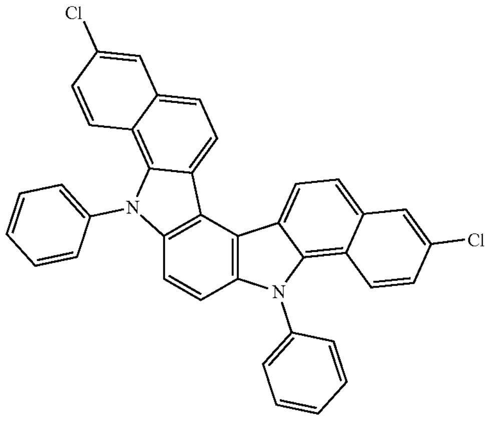

4-e

Compound 4-e (yield: 79%) was prepared in the same manner as in step 1-5, except that Compound 4-d was used instead of Compound 1-g.

m/z $[M+H]^+$=577

Step 4-5: Synthesis of Compound 4

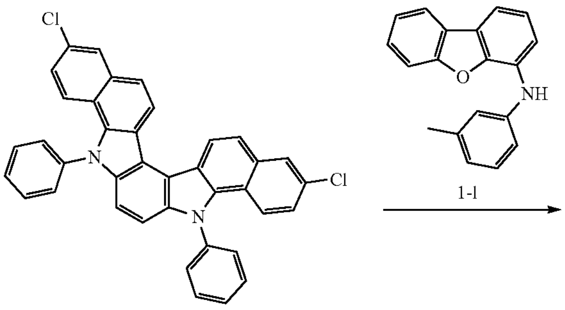

4-e

-continued

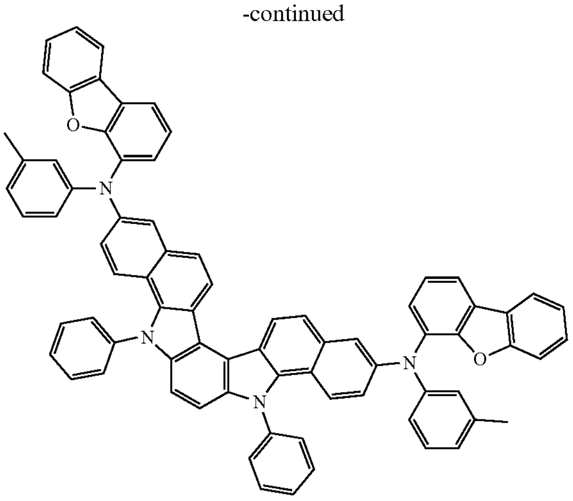

4

Compound 4 (yield: 79%) was prepared in the same manner as in step 1-7, except that Compound 4-e was used instead of Compound 1-i.

m/z $[M+H]^+$=1051

Preparation Example 5: Preparation of Compound 5

Step 5-1: Synthesis of Intermediate Compound 5-b

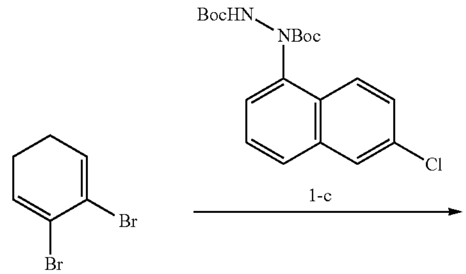

5-a

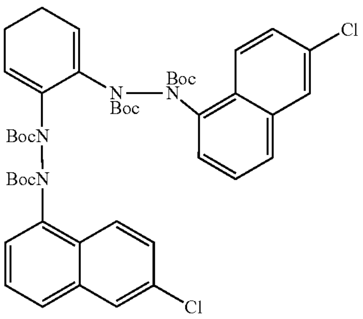

5-b

Compound 5-b (yield: 78%) was prepared in the same manner as in step 1-2, except that Compound 5-a was used instead of Compound 1-d.

m/z $[M+H]^+$=861

Step 5-2: Synthesis of Intermediate Compound 5-c

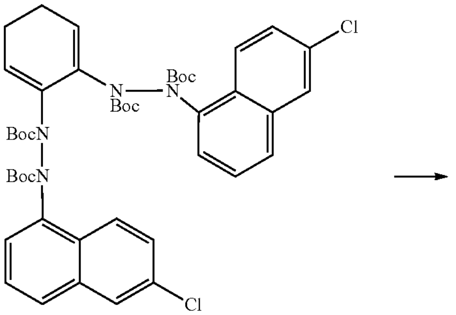

5-b

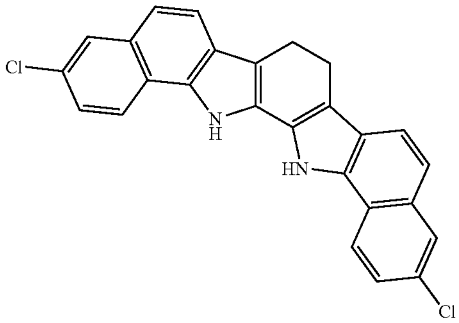

5-c

Compound 5-c (yield: 81%) was prepared in the same manner as in step 1-3, except that Compound 5-b was used instead of Compound 1-e.

m/z $[M+H]^+$=427

Step 5-3: Synthesis of Intermediate Compound 5-d

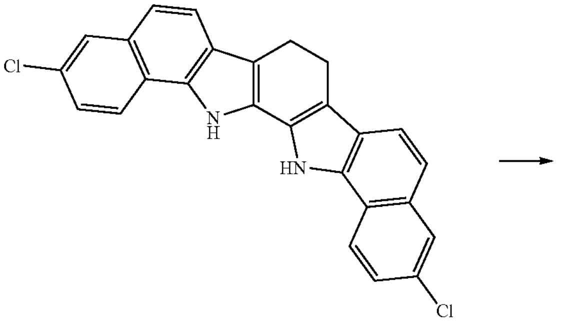

5-c

-continued

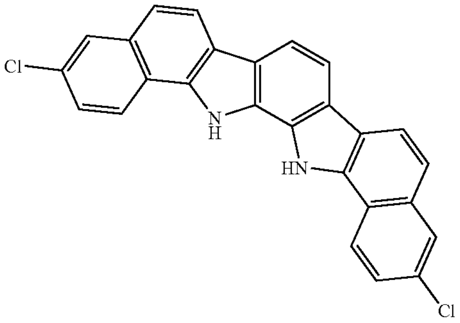

5-d

Compound 5-d (yield: 82%) was prepared in the same manner as in step 1-4, except that Compound 5-c was used instead of Compound 1-f.

m/z $[M+H]^+$=425

Step 5-4: Synthesis of Intermediate Compound 5-e

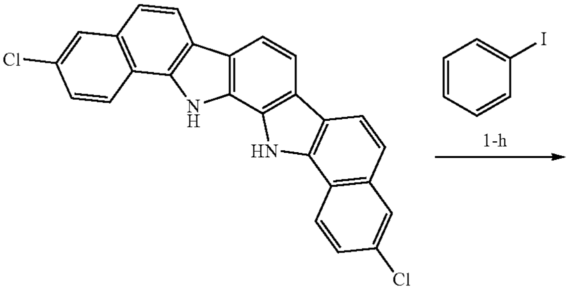

5-d

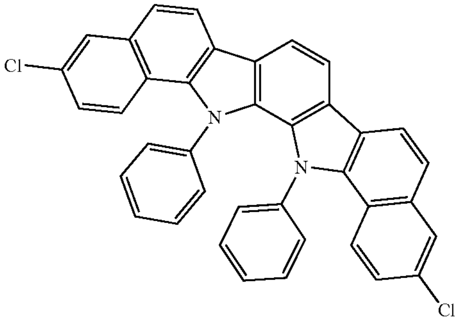

5-e

Compound 5-e (yield: 87%) was prepared in the same manner as in step 1-5, except that Compound 5-d was used instead of Compound 1-g.

m/z $[M+H]^+$=577

Step 5-5: Synthesis of Compound 5

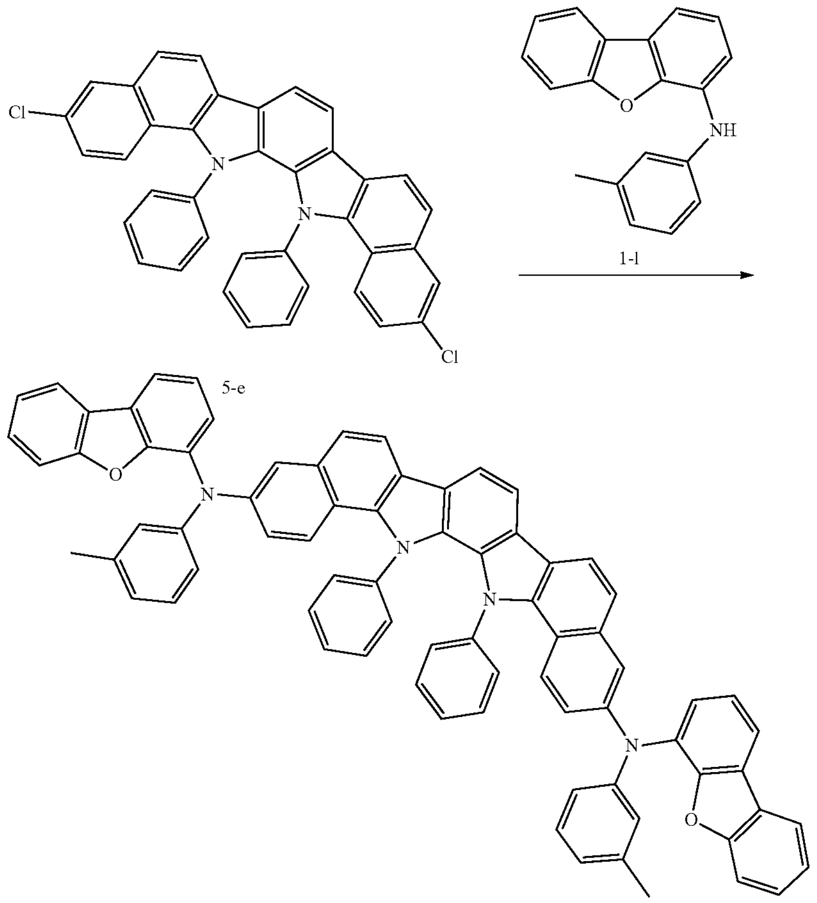

5-e 1-l

5

Compound 5 (yield: 73%) was prepared in the same manner as in step 1-7, except that Compound 5-e was used instead of Compound 1-i.

m/z $[M+H]^+=1051$

Preparation Example 6: Preparation of Compound 6

Step 6-1: Synthesis of Intermediate Compound 6-c

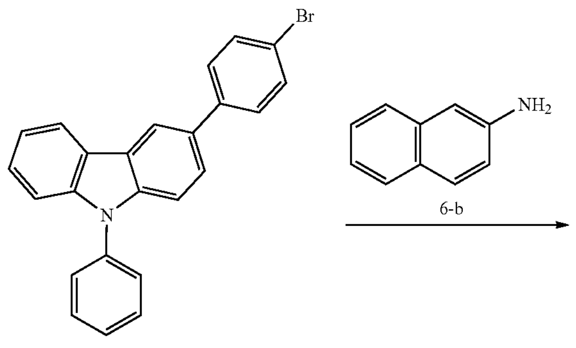

6-b 6-a

-continued

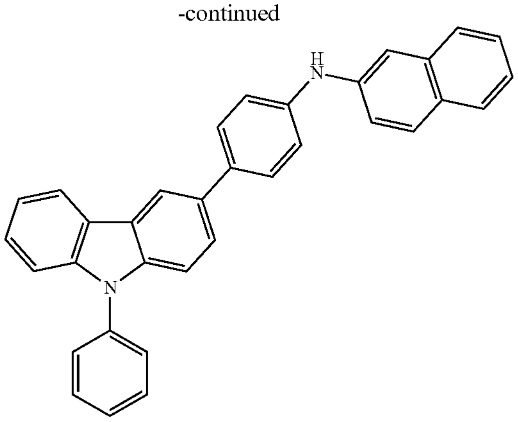

6-c

Compound 6-a (1.0 eq.), Compound 6-b (1.2 eq.) and NaOt-Bu (2.0 eq.) were placed in a round bottom flask and dissolved in anhydrous toluene. After raising the bath temperature to 110° C., $Pd((t\text{-}Bu)_3P)_2$ (3 mol %) was added dropwise thereto, and the mixture was stirred for 4 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 6-c (yield: 89%).

m/z $[M+H]^+$=461.

Step 6-2: Synthesis of Compound 6

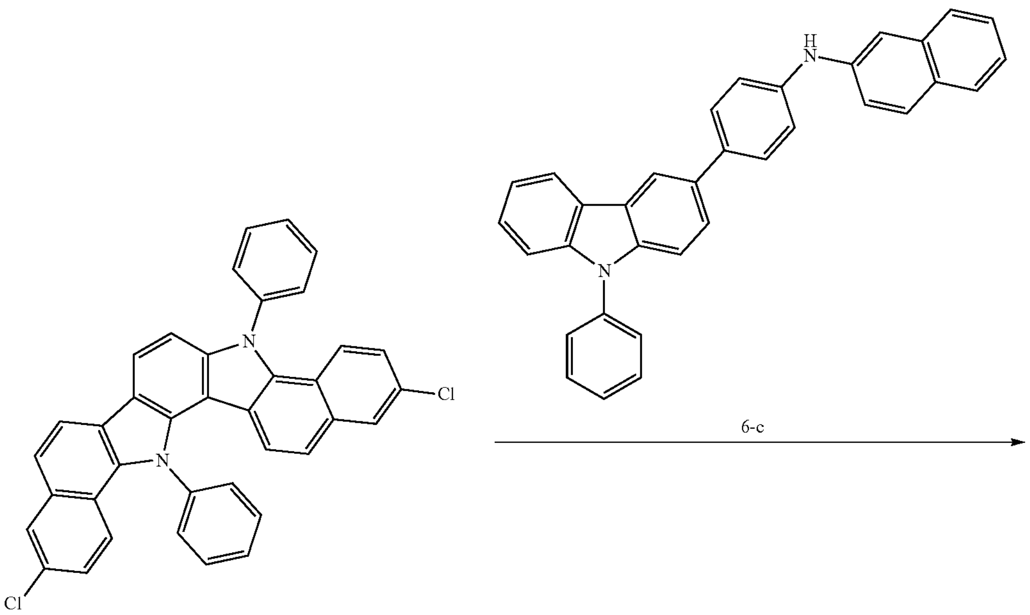

1-i

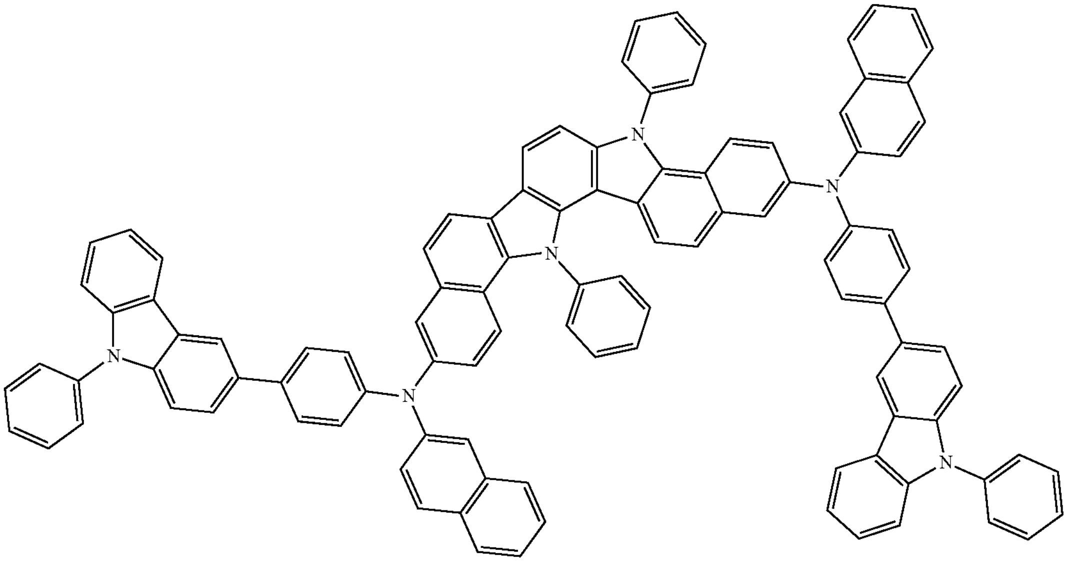

6

Compound 6 (yield: 78%) was prepared in the same manner as in step 1-7, except that Compound 6-c was used instead of Compound 1-l.

m/z $[M+H]^+$=1426

Preparation Example 7: Synthesis of Compound 7
Step 7-1: Synthesis of Compound 7
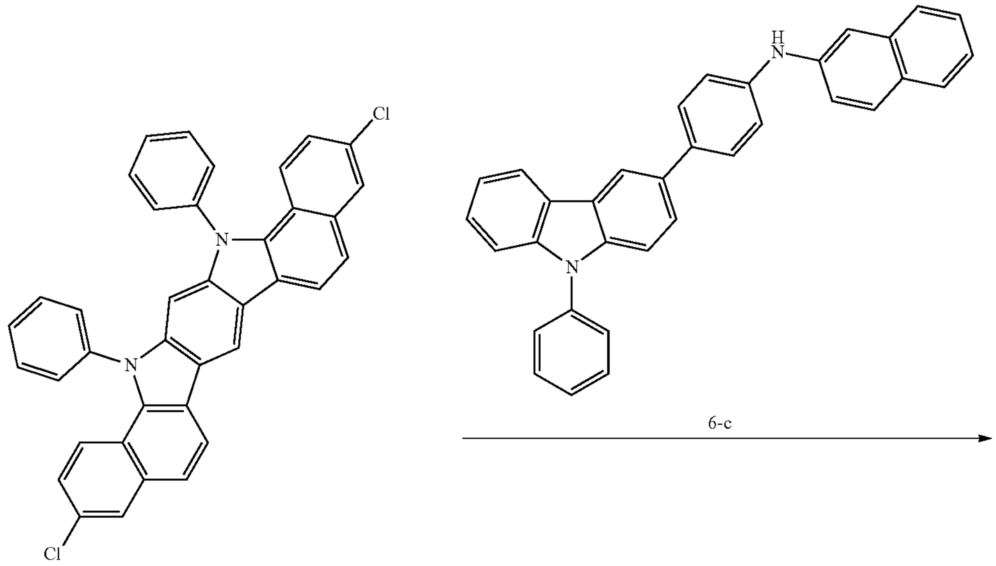
2-e
6-c
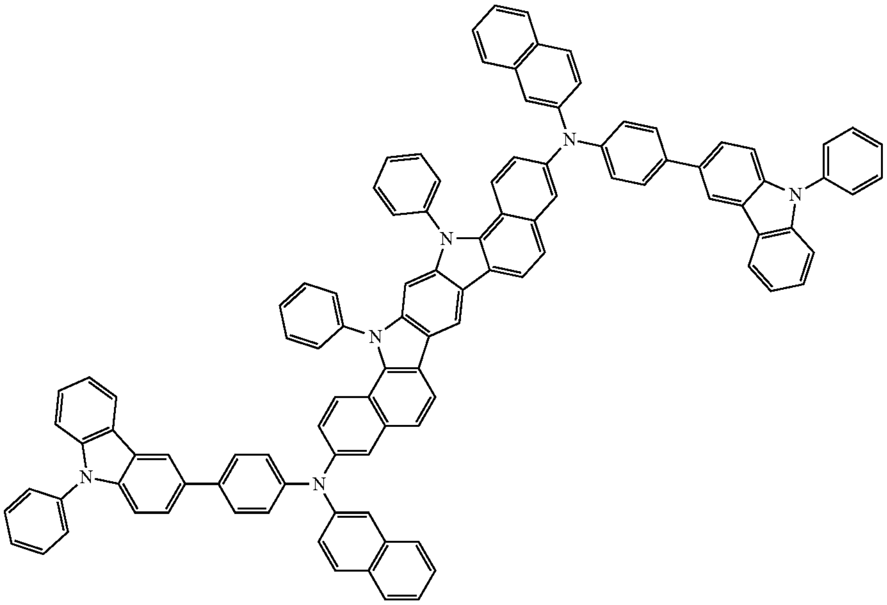
7
Compound 7 (yield: 78%) was prepared in the same manner as in step 2-5, except that Compound 6-c was used instead of Compound 1-1.
m/z $[M+H]^+=1426$ Preparation Example 8: Synthesis of Compound 8
Step 8-1: Synthesis of Compound 8
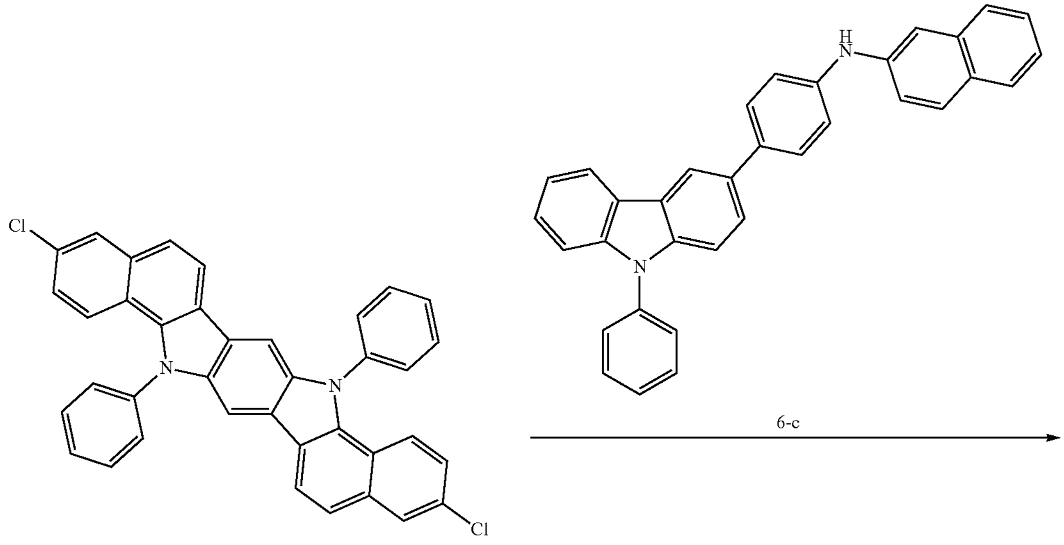
3-e
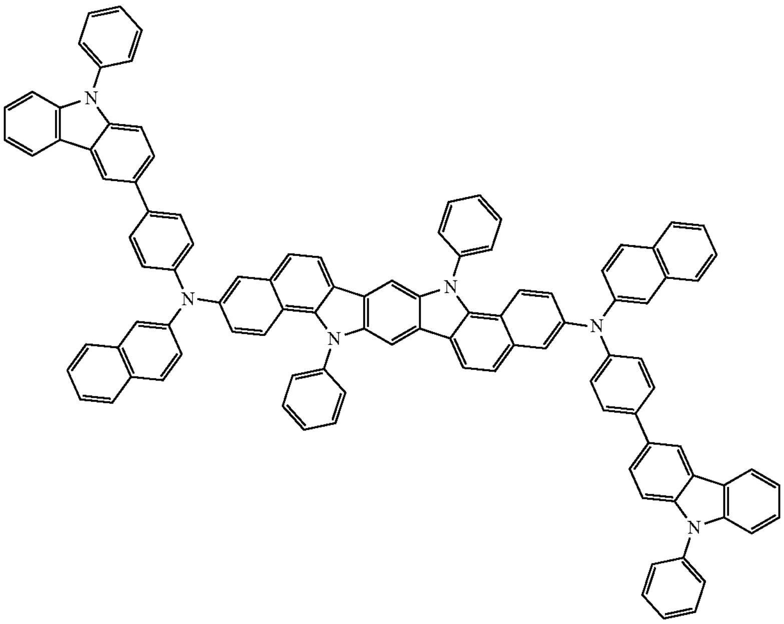
8
Compound 8 (yield: 80%) was prepared in the same manner as in step 3-5, except that Compound 6-c was used instead of Compound 1-1.
m/z $[M+H]^+$=1426

Preparation Example 9: Synthesis of Compound 9
Step 9-1: Synthesis of Compound 9
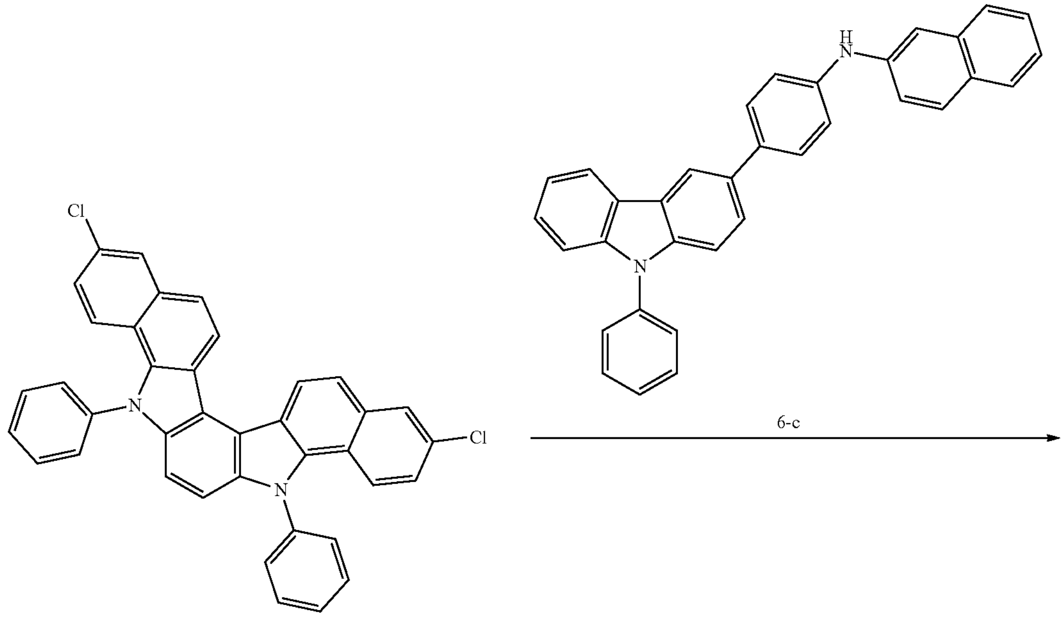
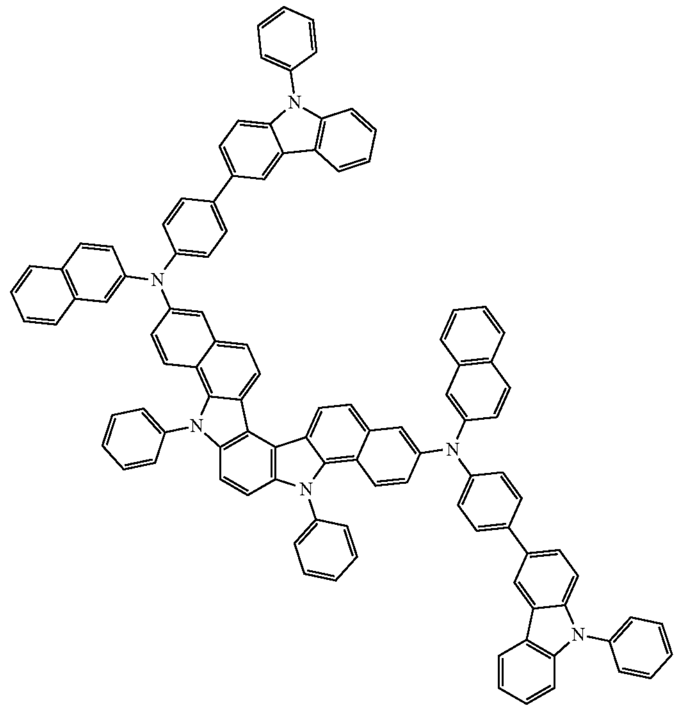
9
Compound 9 (yield: 75%) was prepared in the same manner as in step 4-5, except that Compound 6-c was used instead of Compound 1-l.
m/z $[M+H]^+$=1426

Preparation Example 10: Synthesis of Compound 10
Step 10-1: Synthesis of Compound 10
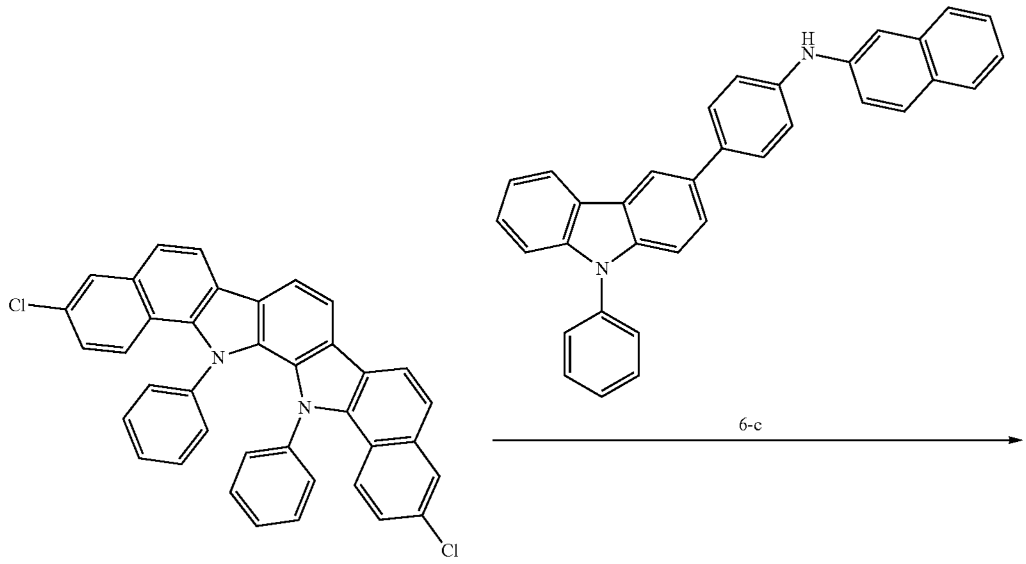
5-e
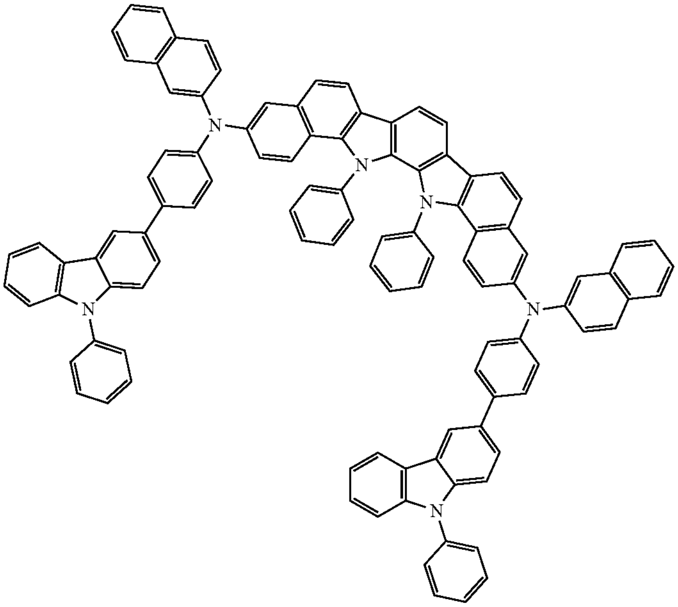
10

Compound 10 (yield: 82%) was prepared in the same manner as in step 5-5, except that Compound 6-c was used instead of Compound 1-1.

m/z $[M+H]^+$=1426

Preparation Example 11: Synthesis of Compound 11

Step 11-1: Synthesis of Intermediate Compound 11-c

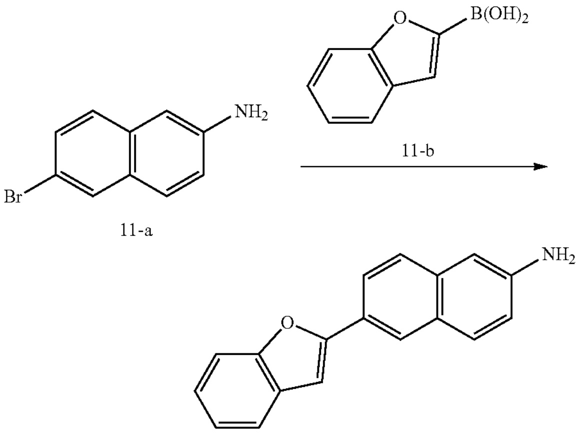

11-a 11-c

Compound 11-a (1.0 eq.), Compound 11-b (1.2 eq.) and (tetrakis(triphenylphosphine)palladium(0))($Pd(PPh_3)_4$, 3 mol %) were placed in a round bottom flask and dissolved in anhydrous toluene (0.21 M). After raising the bath temperature to 110° C., $Cs_2CO_3$ (3.0 eq.) dissolved in $H_2O$ was added dropwise to the reaction solution. Then, the mixture was stirred for 2 hours under a bath temperature of 110° C. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 11-c (yield: 92%).

m/z $[M+H]^+$=260.

Step 11-2: Synthesis of Intermediate Compound 11-e

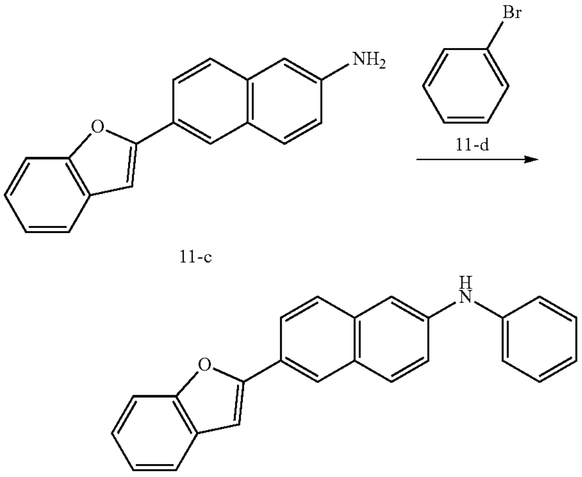

11-c 11-e

Compound 11-c (1.0 eq.), Compound 11-d (1.2 eq.) and NaOt-Bu (2.0 eq.) were placed in a round bottom flask and dissolved in anhydrous toluene. After raising the bath temperature to 110° C., $Pd((t\text{-}Bu)_3P)_2$ (3 mol %) was added dropwise to the reaction solution, and the mixture was stirred for 4 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound 11-e (yield: 83%).

m/z $[M+H]^+$=336.

Step 11-3: Synthesis of Compound 11

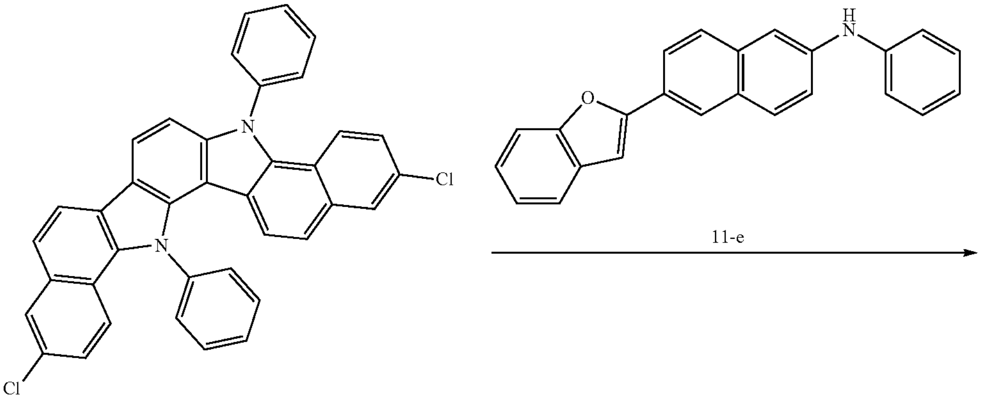

1-i

-continued
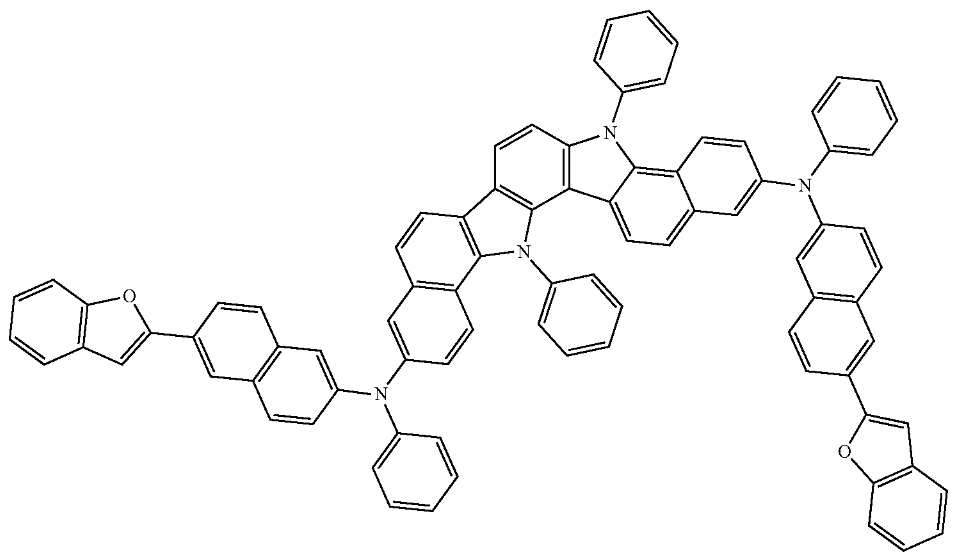
11
Compound 11 (yield: 82%) was prepared in the same manner as in step 1-7, except that Compound 11-e was used instead of Compound 1-l.
m/z $[M+H]^+$=1175
Preparation Example 12: Synthesis of Compound 12
Step 12-1: Synthesis of Compound 12
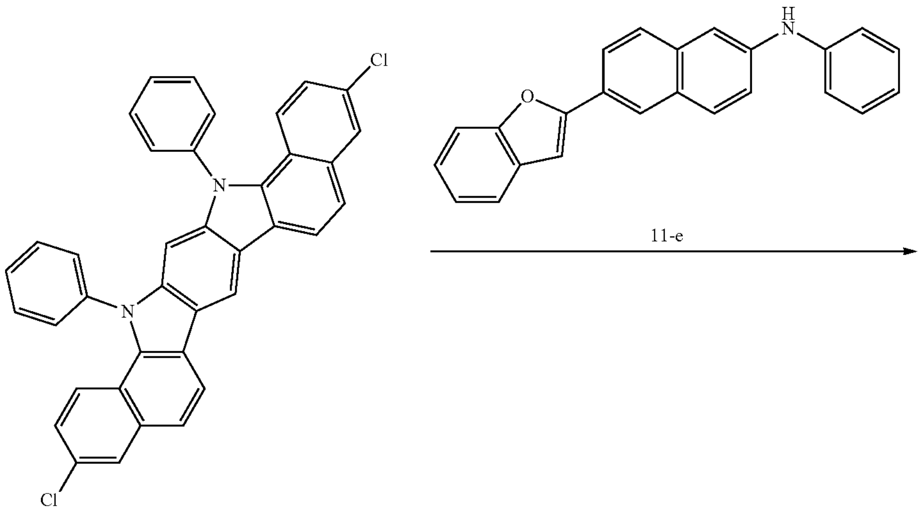
2-e -continued
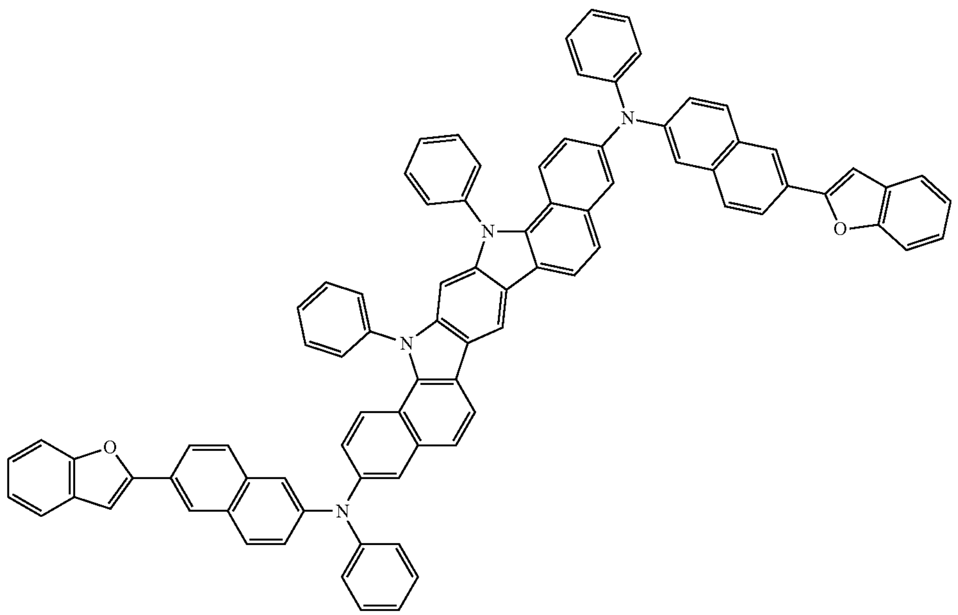
12
Compound 12 (yield: 70%) was prepared in the same manner as in step 2-5, except that Compound 11-e was used instead of Compound 1-l.
m/z $[M+H]^+$=1175
Preparation Example 13: Synthesis of Compound 13
Step 13-1: Synthesis of Compound 13
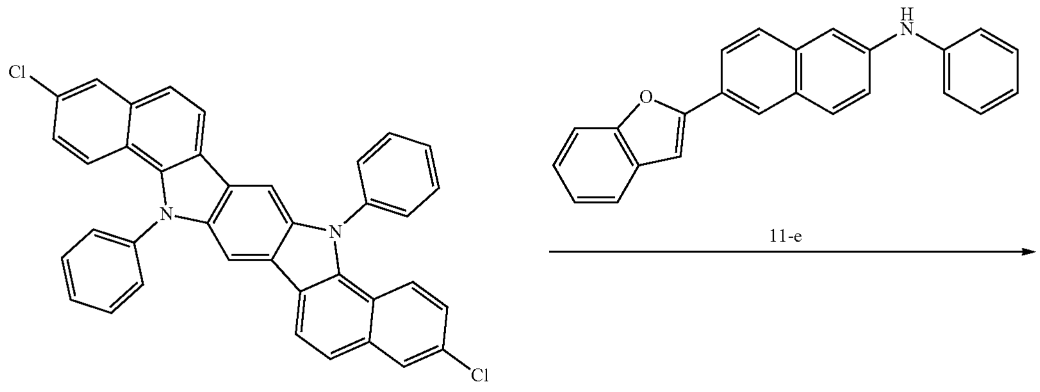
3-e -continued
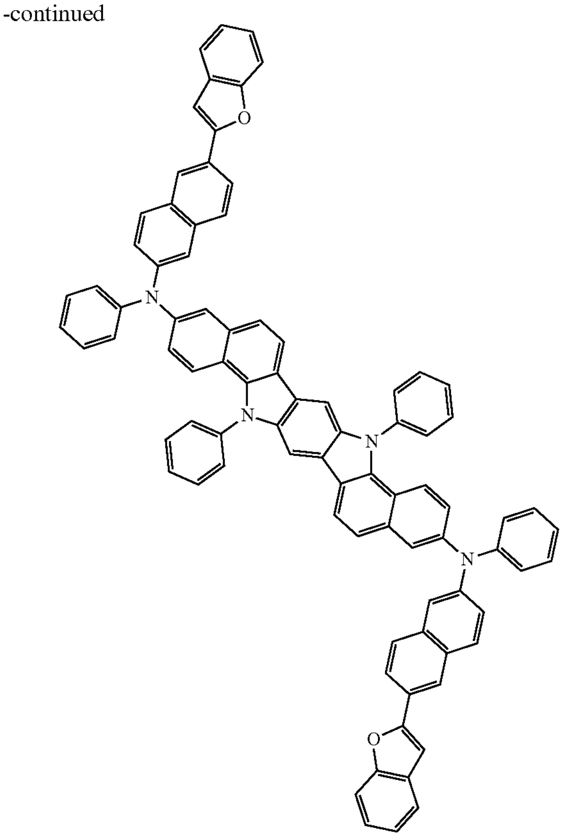
13
Compound 13 (yield: 87%) was prepared in the same manner as in step 3-5, except that Compound 11-e was used instead of Compound 1-1.
m/z $[M+H]^+$=1175
Preparation Example 14: Synthesis of Compound 14
Step 14-1: Synthesis of Compound 14
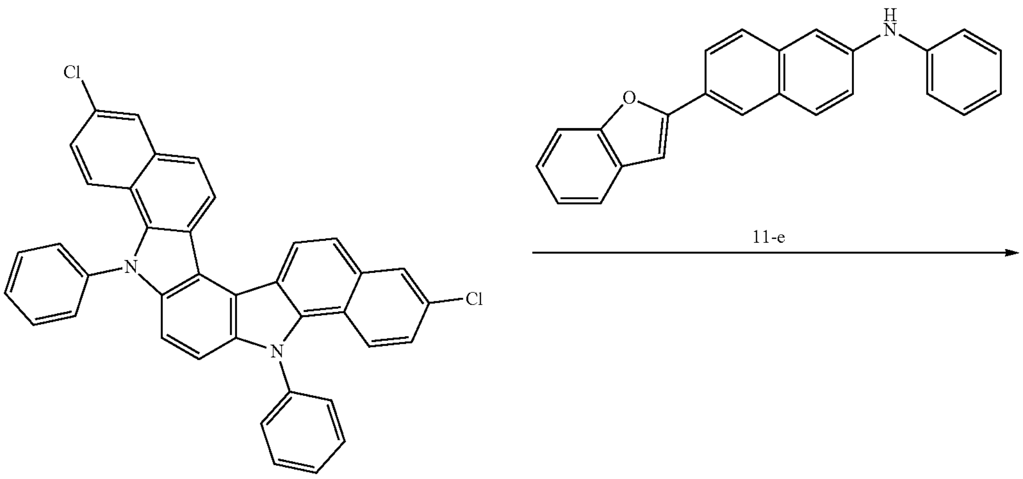
4-e -continued
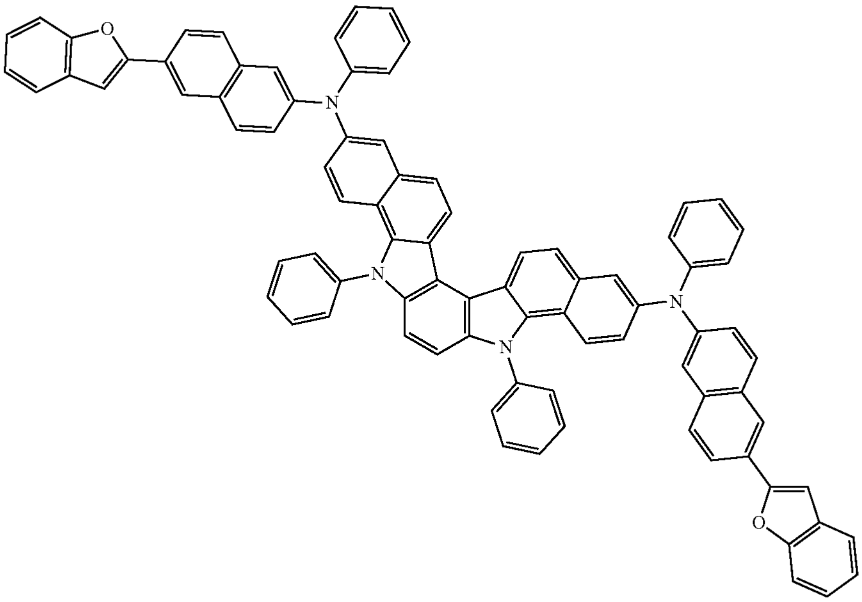
14
Compound 14 (yield: 77%) was prepared in the same manner as in step 4-5, except that Compound 11-e was used instead of Compound 1-1.
m/z $[M+H]^+$=1175
Preparation Example 15: Synthesis of Compound 15
Step 15-1: Synthesis of Compound 15
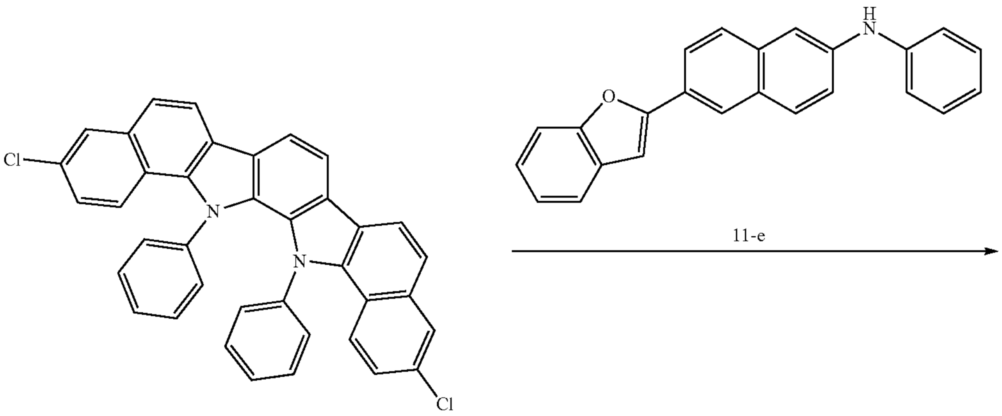
5-e -continued
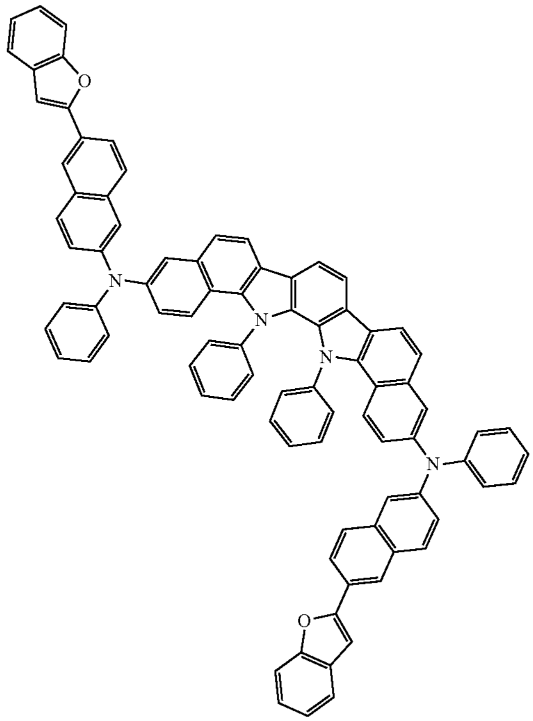
15
Compound 15 (yield: 84%) was prepared in the same manner as in step 5-5, except that Compound 11-e was used instead of Compound 1-l.
m/z $[M+H]^+$=1175
Preparation Example 16: Synthesis of Compound 16
Step 16-1: Synthesis of Intermediate Compound 16-b
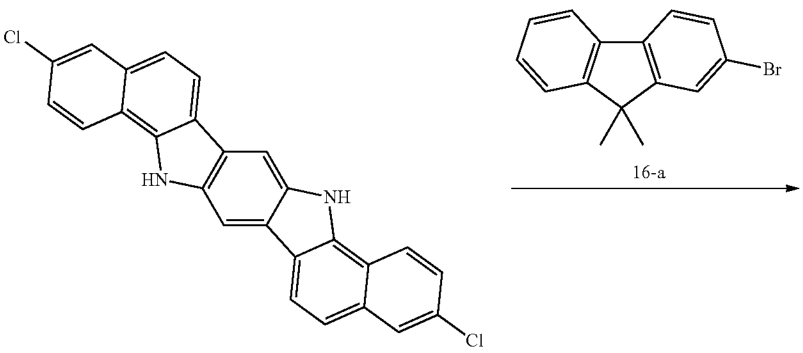
3-d -continued
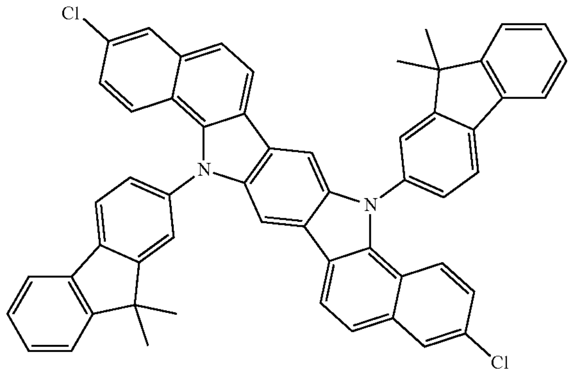
16-b
Compound 16-b (yield: 89%) was prepared in the same manner as in step 3-4, except that Compound 16-a was used instead of Compound 1-h.
m/z $[M+H]^+=809$
Step 16-2: Synthesis of Compound 16
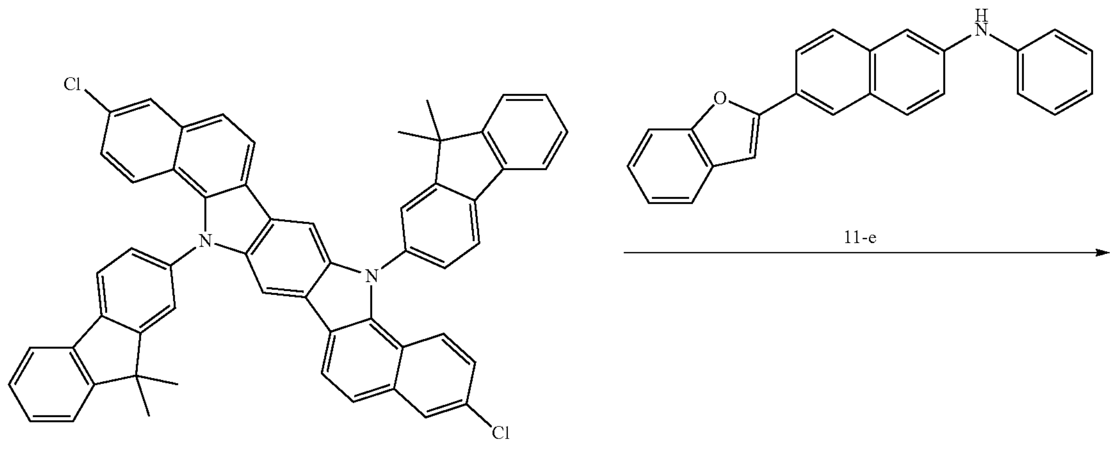
16-b -continued

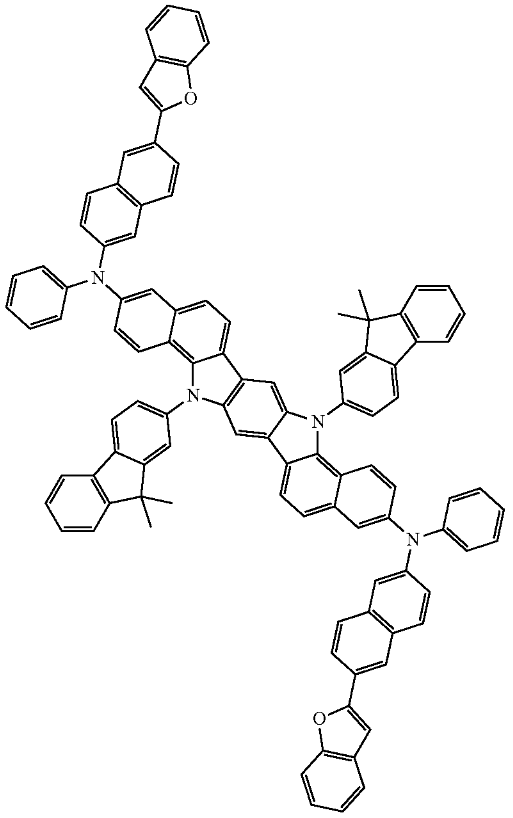

16

Compound 16 (yield: 89%) was prepared in the same manner as in step 13-1, except that Compound 16-b was used instead of Compound 3-e.

m/z $[M+H]^+$=1408

Preparation Example 17: Synthesis of Compound 17

Step 17-1: Synthesis of Intermediate Compound 17-b

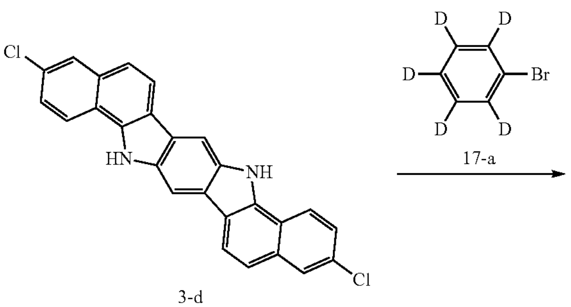

3-d

-continued

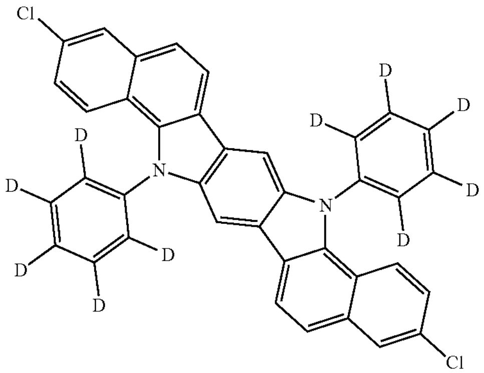

17-b

Compound 17-b (yield: 89%) was prepared in the same manner as in step 3-4, except that Compound 17-a was used instead of Compound 1-h.

m/z $[M+H]^+$=587

Step 17-2: Synthesis of Compound 17
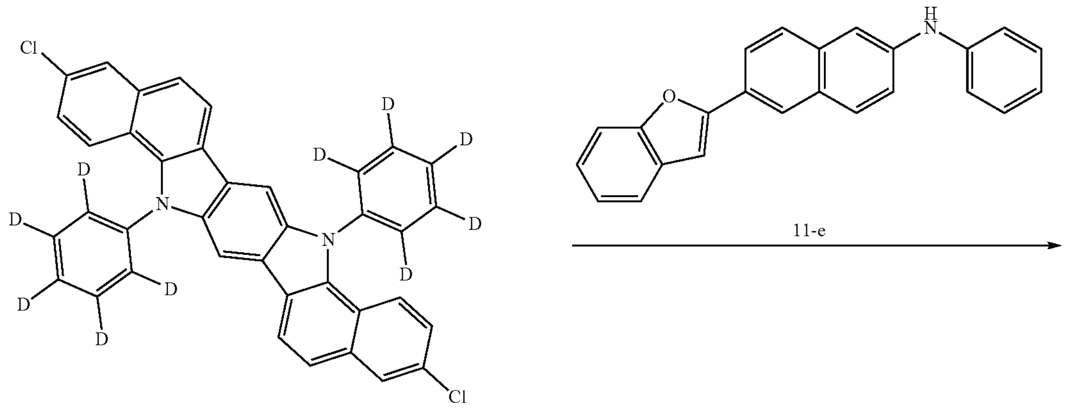
17-b
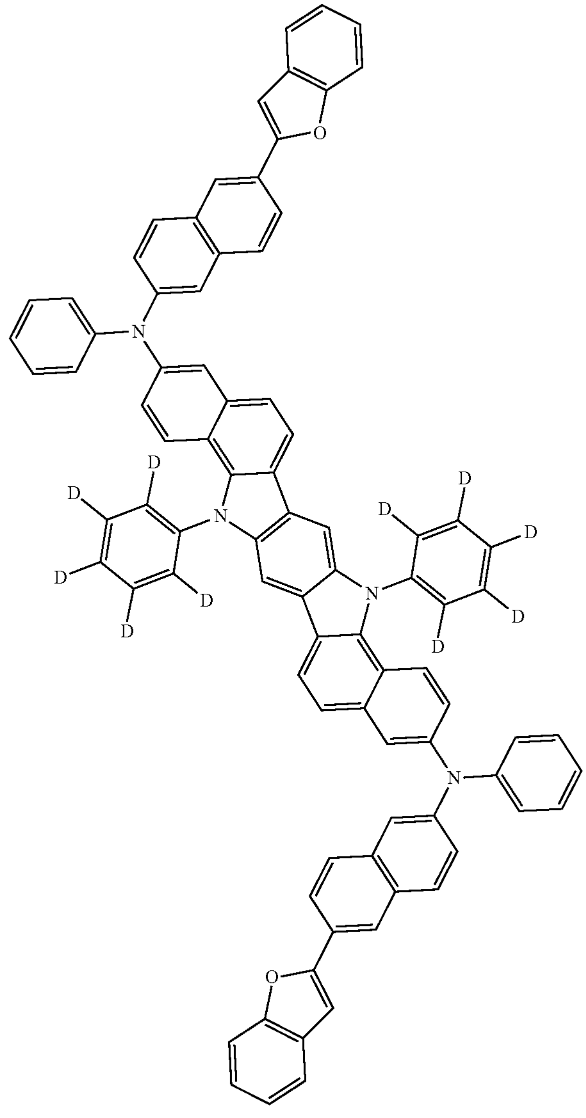
17

Compound 17 (yield: 84%) was prepared in the same manner as in step 13-1, except that Compound 17-b was used instead of Compound 3-e.

m/z $[M+H]^+$=2107

Preparation Example 18: Synthesis of Compound 18

Step 18-1: Synthesis of Intermediate Compound 18-b

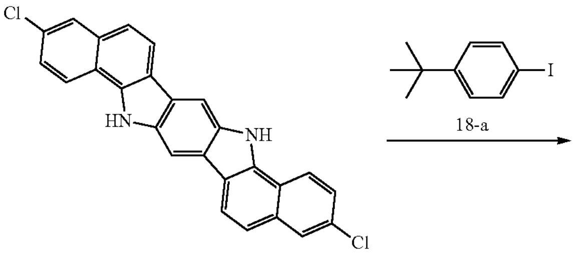

3-d

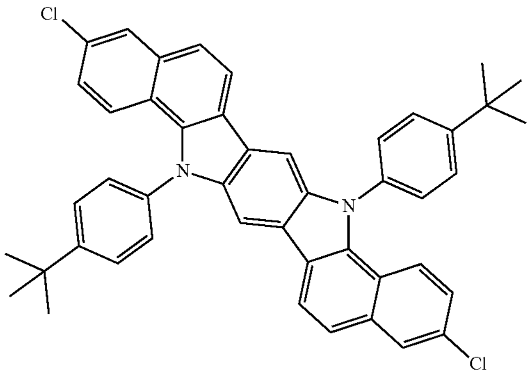

18-b

Compound 18-b (yield: 89%) was prepared in the same manner as in step 3-4, except that Compound 18-a was used instead of Compound 1-h.

m/z $[M+H]^+$=689

Step 18-2: Synthesis of Intermediate Compound 18-d

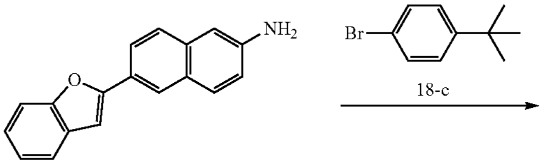

11-c

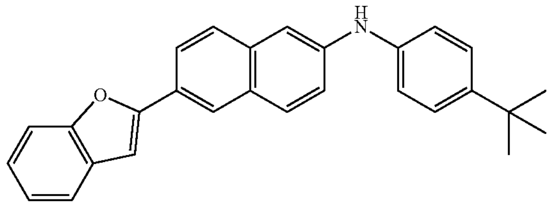

18-d

Compound 18-d (yield: 81%) was prepared in the same manner as in step 11-2, except that Compound 18-c was used instead of Compound 11-d.

m/z $[M+H]^+$=392

Step 18-3: Synthesis of Compound 18

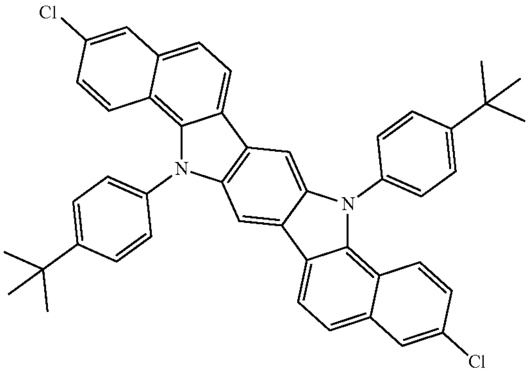

18-b

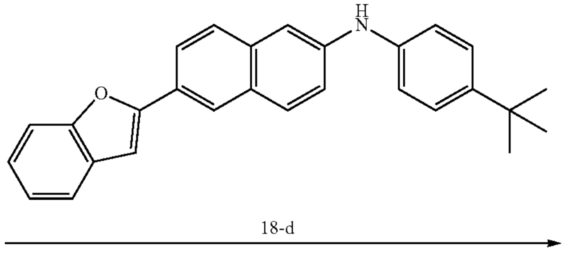

-continued

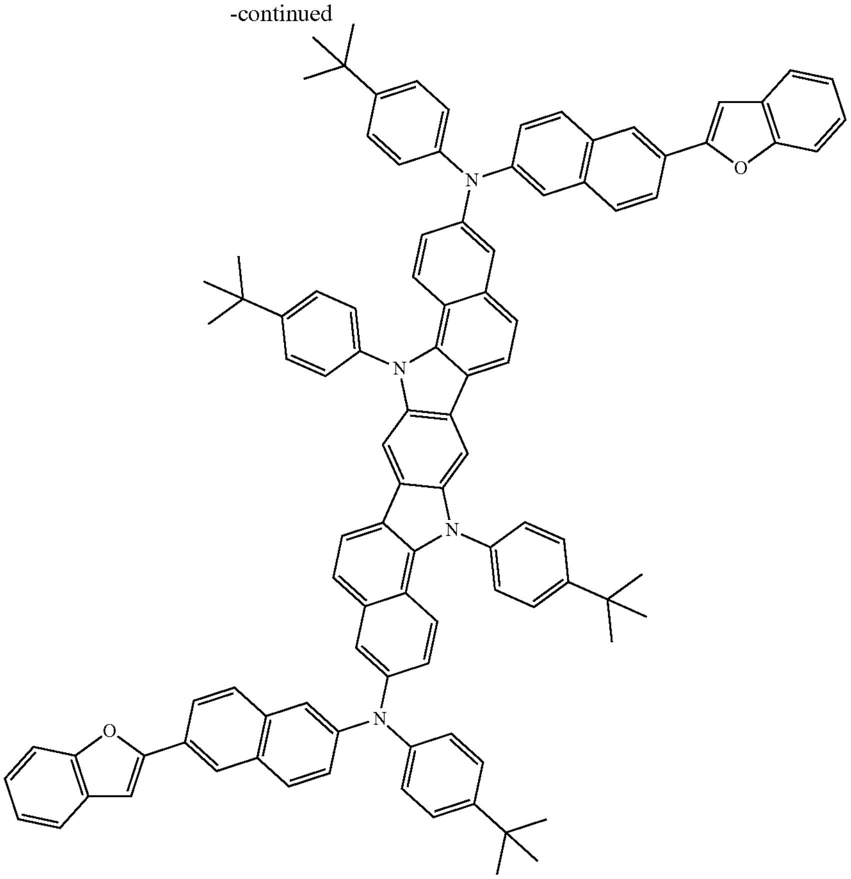

18

Compound 18 (yield: 83%) was prepared in the same manner as in step 13-1, except that Compound 18-b was used instead of Compound 3-e, and Compound 18-d was used instead of Compound 11-e.

m/z $[M+H]^+=1400$

Comparative Preparation Example 1: Synthesis of Comparative Compound F

Step F-1: Synthesis of Intermediate Compound F-b

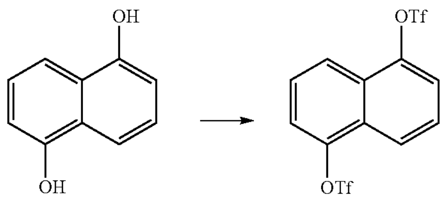

F-a F-b

Compound F-a (1.0 eq.) was placed in a round bottom flask and dissolved in anhydrous $CH_2Cl_2$ (0.28 M). Pyridine (2.5 eq.) was added dropwise to the reaction solution, the bath temperature was lowered from room temperature to 0° C., and the mixture was stirred. Trifluoromethanesulfonic anhydride ($Tf_2$, 2.0 eq.) was slowly added dropwise using a dropping funnel for 30 minutes, the bath temperature was raised to room temperature, and the mixture was stirred for 4 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound F-b (yield: 90%).

m/z $[M+H]^+=425$.

Step F-2: Synthesis of Intermediate Compound F-c

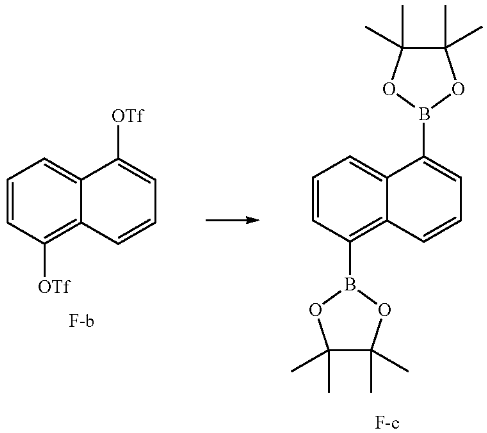

F-b F-c

Compound F-b (1.0 eq.), bis(pinacolato)diborane ($B_2pin_2$, 2.2 eq.), and KOAc (6.0 eq.) were placed in a round bottom flask and dissolved in anhydrous dioxane (0.2 M). After raising the bath temperature from room temperature to 100° C., (1,1'-bis(diethylphosphino)ferrocene)palladium(II) dichloride ($Pd(dppf)Cl_2$, 10 mol %) was added dropwise to the reaction solution, and the mixture was stirred for 2 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound F-c (yield: 87%).

m/z $[M+H]^+$=381.

Step F-3: Synthesis of Intermediate Compound F-e

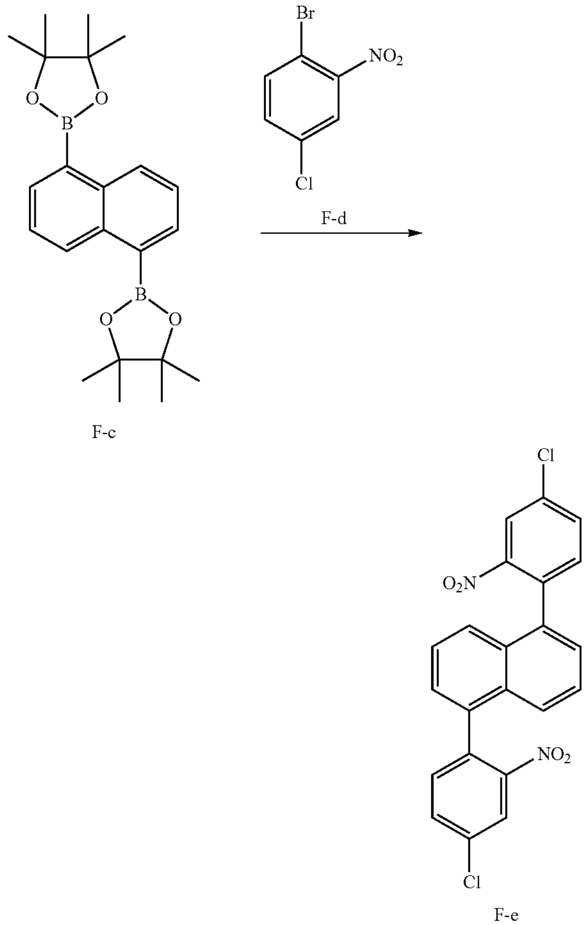

F-c

F-d

F-e

Compound F-c (1.0 eq.), Compound F-d (2.2 eq.), and (tetrakis(triphenylphosphine)palladium(0)) ($Pd(PPh_3)_4$, 12 mol %) were placed in a round bottom flask and dissolved in anhydrous PhMe (toluene, 0.21 M). After raising the bath temperature to 110° C., $Cs_2CO_3$ (5.0 eq.) dissolved in $H_2O$ was added dropwise to the reaction solution. Then, the mixture was stirred overnight under a bath temperature of 110° C. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound F-e (yield: 99%).

m/z $[M+H]^+$=439.

Step F-4: Synthesis of Intermediate Compound F-f

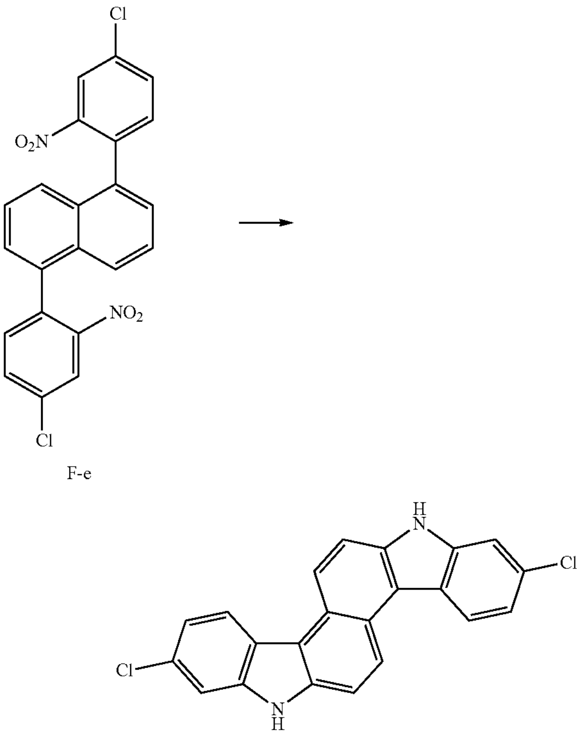

F-e

F-f

Compound F-e (1.0 eq.) and $PPh_3$ (5.0 eq.) were placed in a round bottom flask and dissolved in anhydrous 1,2-dichlorobenzene (0.075 M). The mixture was stirred overnight under a bath temperature of 180° C. After the reaction, the reaction mixture was stirred and then cooled to room temperature. Then, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound F-f (yield: 85%).

m/z $[M+H]^+$=375.

Step F-5: Synthesis of Intermediate Compound F-h

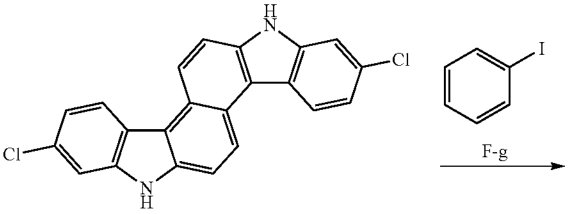

F-f

F-g

-continued

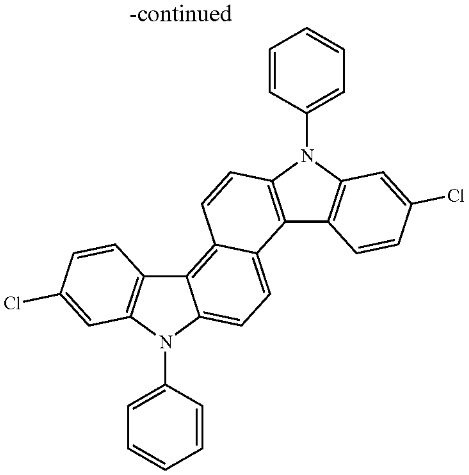

F-h

Compound F-f (1.0 eq.) and sodium tert-butoxide (NaOt-Bu, 6.05 eq.) were placed in a round bottom flask and dissolved in anhydrous PhMe (0.03 M). Then, Compound F-g (7.1 eq.) was added dropwise to the reaction solution. Next, bis(tri-tert-butylphosphine)palladium(0)(Pd(P(t-Bu)$_3$)$_2$, 20 mol %) was added dropwise to the reaction mixture under a bath temperature of 110° C., and the mixture was stirred for 22 hours. After the reaction, the reaction mixture was washed with dichloromethane and water, the organic layer was separated, water was removed with $MgSO_4$, and passed through a celite-silica pad. The passed solution was concentrated under reduced pressure, and then purified by column chromatography to obtain Intermediate Compound F-h (yield: 85%).

m/z $[M+H]^+$=527.

Step F-6: Synthesis of Compound F

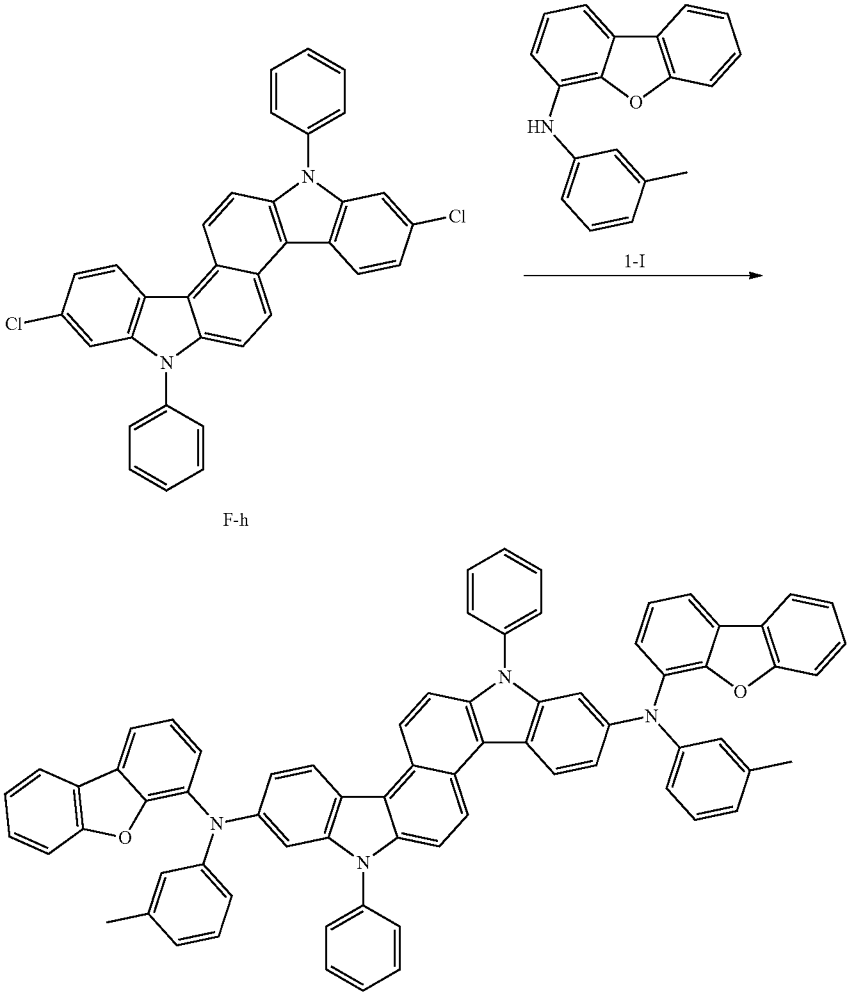

F-h

F

Compound F-h (1.0 eq.), Compound 1-1 (2.3 eq.), P(t-Bu)$_3$HBF$_4$ (10 mol %), and NaOt-Bu (2.2 eq.) were placed in a round bottom flask and dissolved in anhydrous PhMe (0.02 M). Pd$_2$(dba)$_3$ (5 mol %) was added dropwise to the reaction solution under a bath temperature of 105° C., and the mixture was stirred overnight. After the reaction, the reaction mixture was stirred and then cooled to room temperature. An excess of n-hexane was added dropwise to the reaction product to precipitate the product. The precipitate was washed with MeOH and $H_2O$ and filtered to obtain a filter cake. A sufficiently dried filter cake was added to 1,2-dichlorobenzene and dissolved under heating. The dissolved reaction product was passed through a celite-silica pad. An excess of n-hexane was added dropwise to the passed solution to precipitate the product. The precipitate was washed with n-hexane and MeOH and filtered to obtain a filter cake, which was sufficiently dried to synthesize Comparative Compound F (yield: 71%).

m/z [M+H]$^+$=1001.

Comparative Preparation Example 2: Synthesis of Comparative Compound G

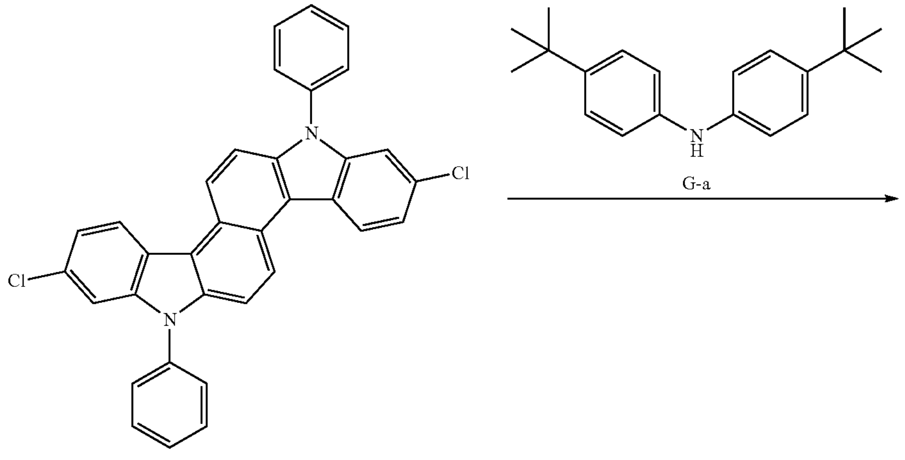

F-h

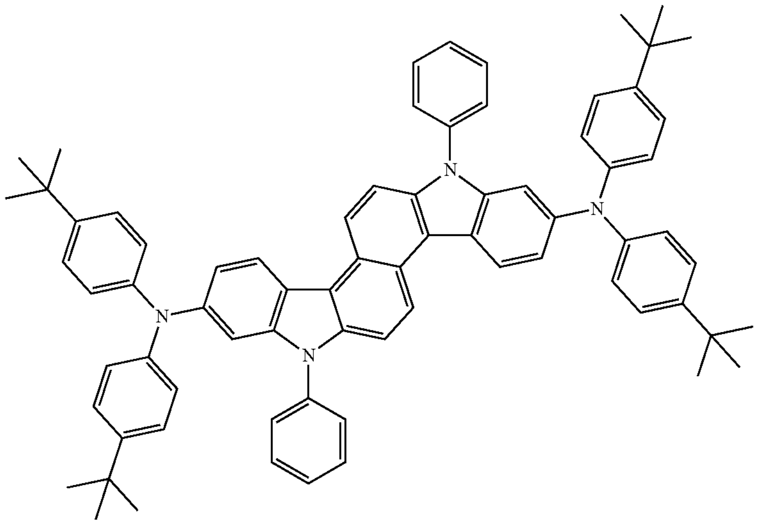

G

Compound G (yield: 74%) was prepared in the same manner as in the synthesis of Comparative Compound F, except that Compound G-a was used instead of Compound 1-1.

m/z [M+H]$^+$=1018

Comparative Preparation Example 3: Synthesis of Comparative Compound H
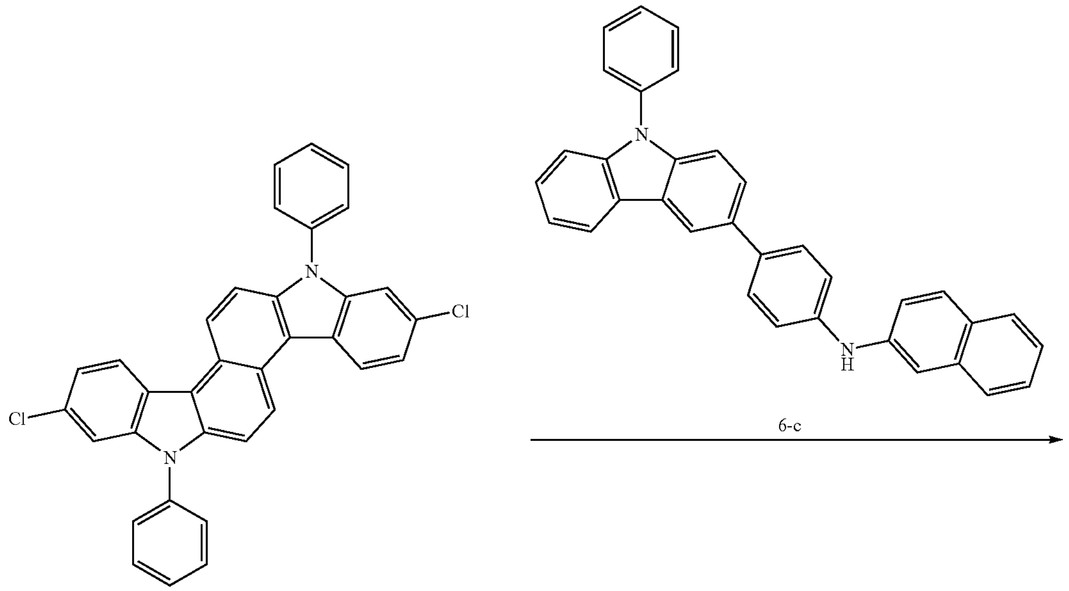
F-h
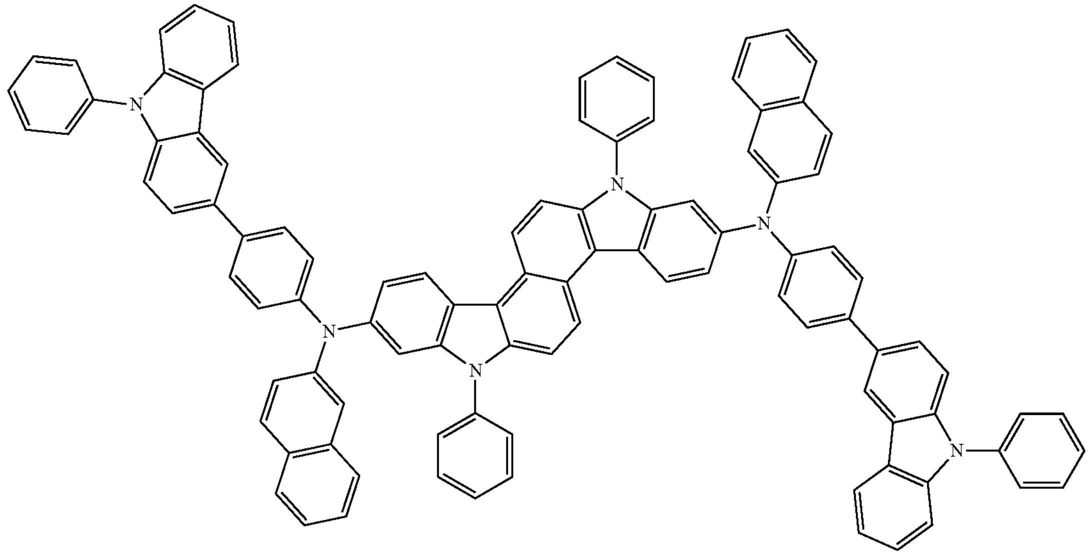
H
Compound H (yield: 68%) was prepared in the same manner as in the synthesis of Comparative Compound F, except that Compound 6-c was used instead of Compound 1-1.
m/z $[M+H]^+=1376$ Comparative Preparation Example 4: Synthesis of Comparative Compound I
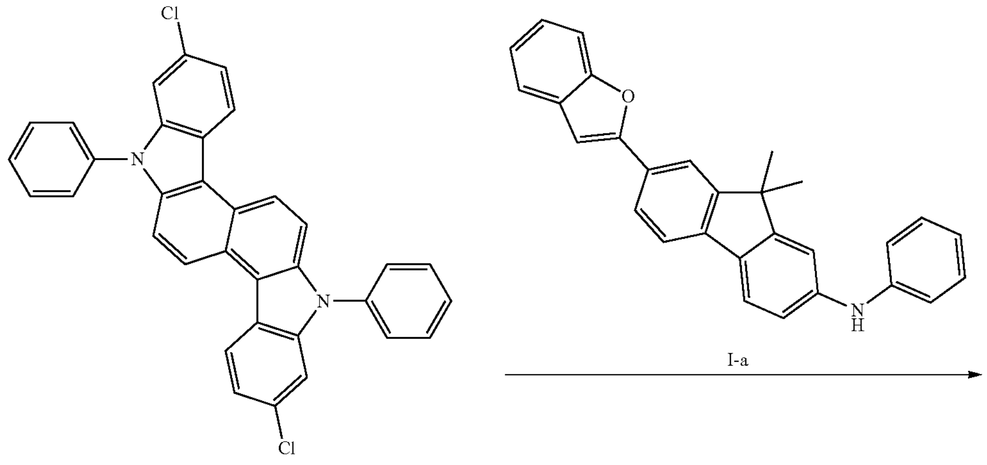
F-h
I-a
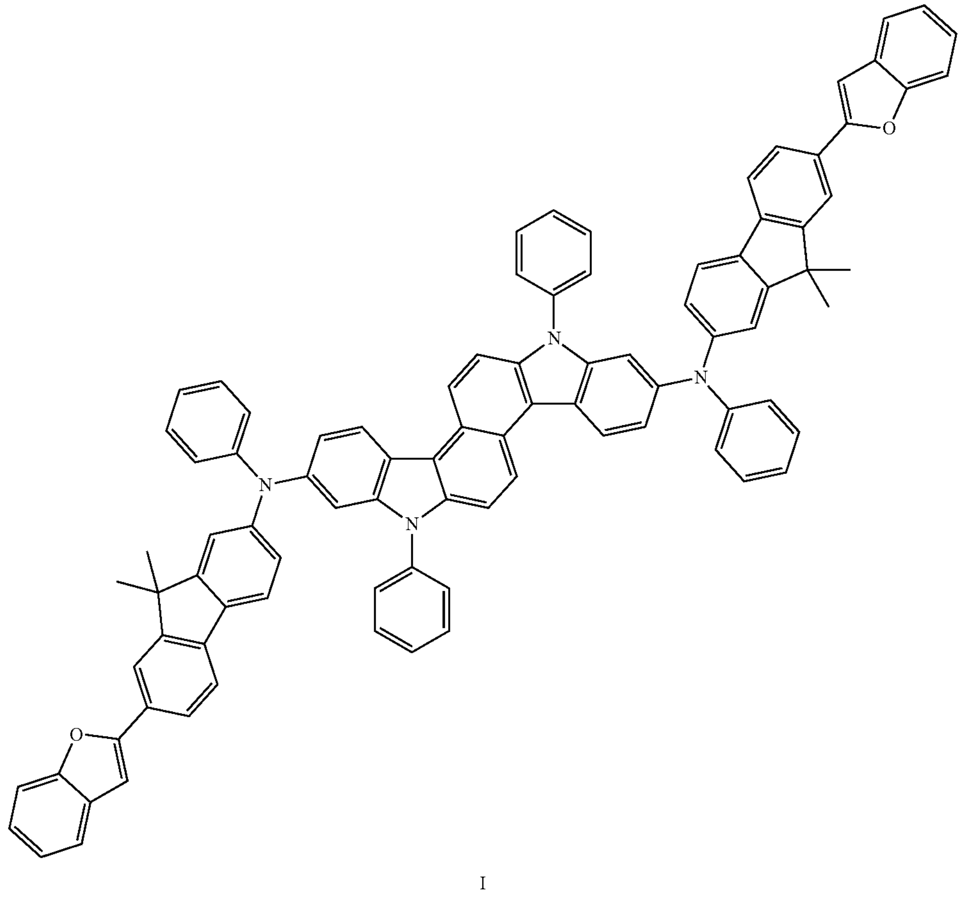
I
Compound I (yield: 82%) was prepared in the same manner as in the synthesis of Comparative Compound F, except that Compound I-a was used instead of Compound 1-1.
m/z $[M+H]^+=1258$

Experimental Example 1: Solubility Experiment

In order to confirm the solubility in the solvent used in the solution process of the compounds prepared in the Preparation Examples and the comparative compounds, each of them was dissolved in the solvent cyclohexanone (CHON) under normal temperature/pressure conditions, and it was confirmed whether 0.1 wt % or more was dissolved. The results are shown in Table 1 below.

TABLE 1

| | Solvent CHON |
|---|---|
| Compound 1 | ○ |
| Compound 2 | ○ |
| Compound 3 | ○ |
| Compound 4 | ○ |
| Compound 5 | ○ |
| Compound 6 | ○ |
| Compound 7 | ○ |
| Compound 8 | ○ |
| Compound 9 | ○ |
| Compound 10 | ○ |
| Compound 11 | ○ |
| Compound 12 | ○ |
| Compound 13 | ○ |
| Compound 14 | ○ |
| Compound 15 | ○ |
| Compound 16 | ○ |
| Compound 17 | ○ |
| Compound 18 | ○ |
| Comparative Compound I | X |

Evaluation list (○): 0.1 wt. % or more soluble
Evaluation list (X): 0.1 wt. % or more insoluble As shown in Table 1, it was confirmed that unlike the Comparative Compound I, the compounds included in Chemical Formula 1 exhibited excellent solubility in cyclohexanone, which is a solvent used in a solution process of an organic light emitting device.

Example 1: Manufacture of Organic Light Emitting Device Example 1

A glass substrate thinly coated with indium tin oxide (ITO) to have a thickness of 500 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl, and acetone solvents, and drying was conducted, and then the substrate was cleaned for 5 minutes, and then transferred to a glove box.

A coating composition, in which the following Compound B and the following Compound C (weight ratio of 2:8) were dissolved in 20 wt/v % cyclohexanone, was spin-coated (4000 rpm) on the ITO transparent electrode, and heat-treated (cured) at 200° C. for 30 minutes to form a hole injection layer with a thickness of 400 Å. A coating composition, in which the following Compound A (Mn: 27,900; Mw: 35,600; measured by gel permeation chromatography (GPC) on Agilent 1200 series, relative to PC standards) was dissolved in 6 wt/v % toluene, spin-coated (4000 rpm) on the hole injection layer, and heat-treated at 200° C. for 30 minutes to form a hole transport layer with a thickness of 200 Å.

A coating composition, in which Compound 1 prepared in Preparation Example 1 and the following Compound D (weight ratio of 2:98) were dissolved in 2 wt/v % cyclohexanone, spin-coated (4000 rpm) on the hole transport layer, and heat-treated at 180° C. for 30 minutes to form a light emitting layer with a thickness of 400 Å.

After being transferred to a vacuum depositor, the following Compound E was vacuum-deposited to a thickness of 350 Å on the light emitting layer to form an electron injection and transport layer.

LiF and aluminum were sequentially deposited to have a thickness of 10 Å and 1000 Å, respectively, on the electron injection and transport layer, thereby forming a cathode.

A

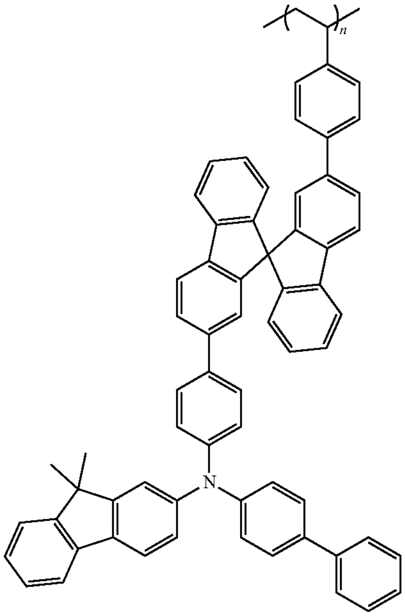

B

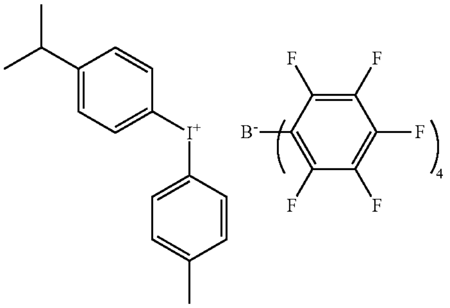

C

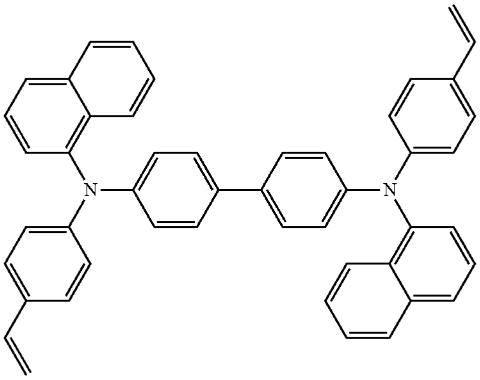

-continued

D

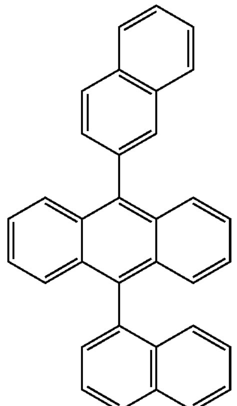

E

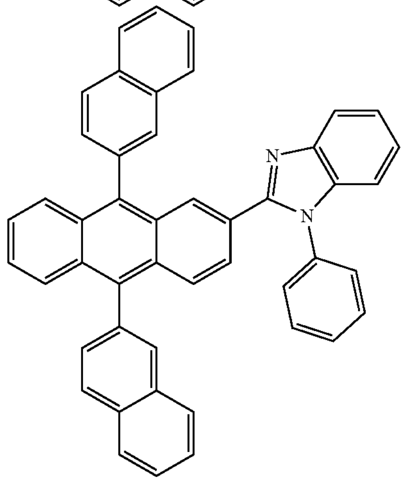

In the above-mentioned process, the vapor deposition rate of the organic material was maintained at 0.4 to 0.7 Å/sec, the deposition rate of LiF was maintained at 0.3 Å/sec, the deposition rate of aluminum was maintained at 2 Å/sec, and the degree of vacuum during the deposition was maintained at $2\times10^{-7}$ to $5\times10^{-8}$ torr.

Examples 2 to 18

An organic light emitting device was manufactured in the same manner as in Example 1, except that the compounds shown in Table 2 below were used instead of Compound 1 as a dopant of the light emitting layer.

Comparative Examples 1 to 3

An organic light emitting device was manufactured in the same manner as in Example 1, except that the compounds shown in Table 2 below were used instead of Compound 1 as a dopant in the light emitting layer.

The structures of the compounds used in the Examples and Comparative Examples are as follows:

1

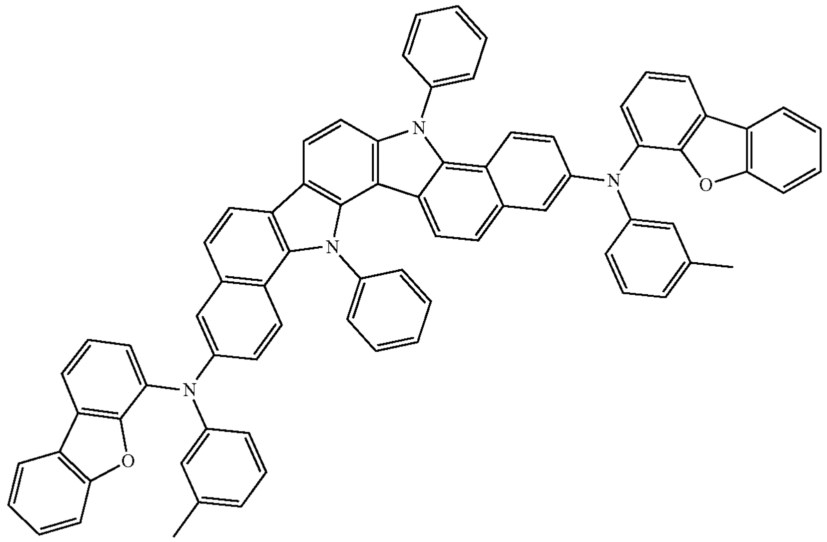

-continued
2
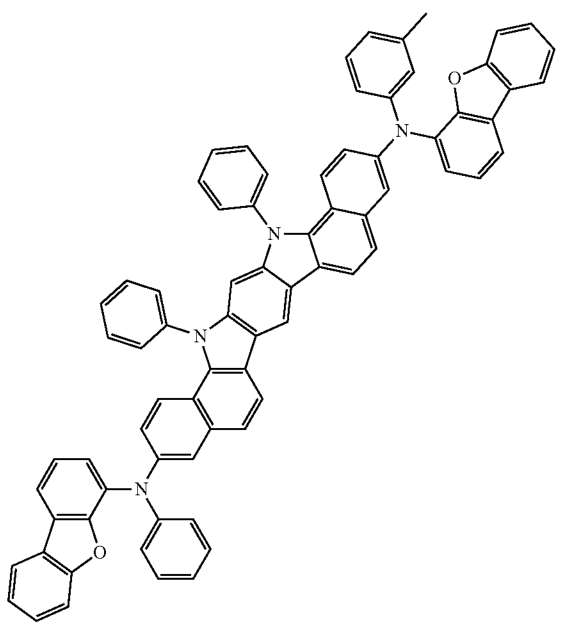
3
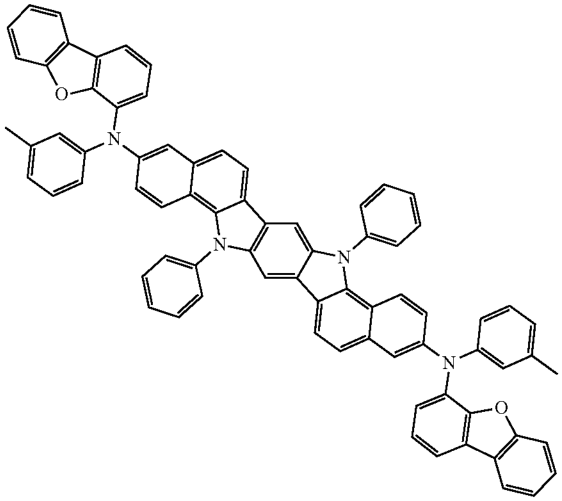
4
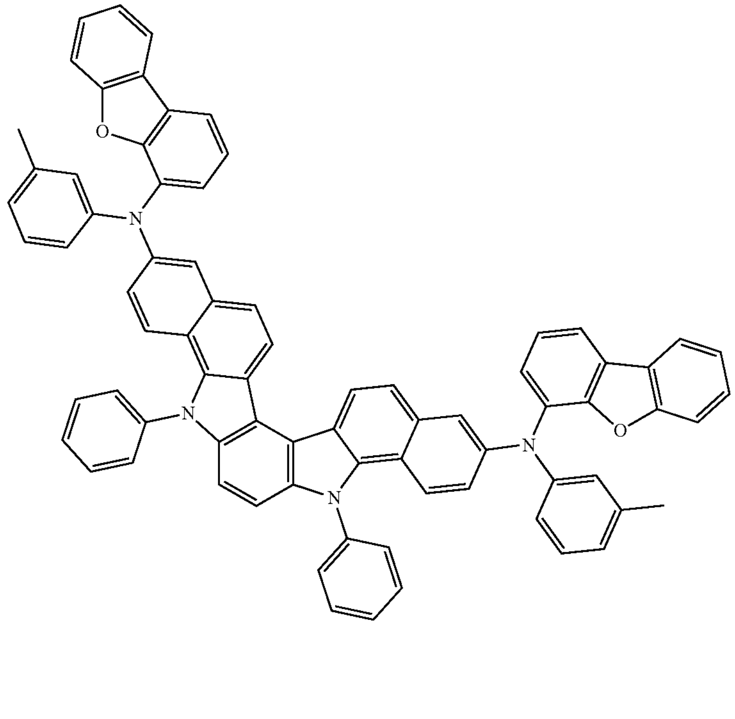

-continued
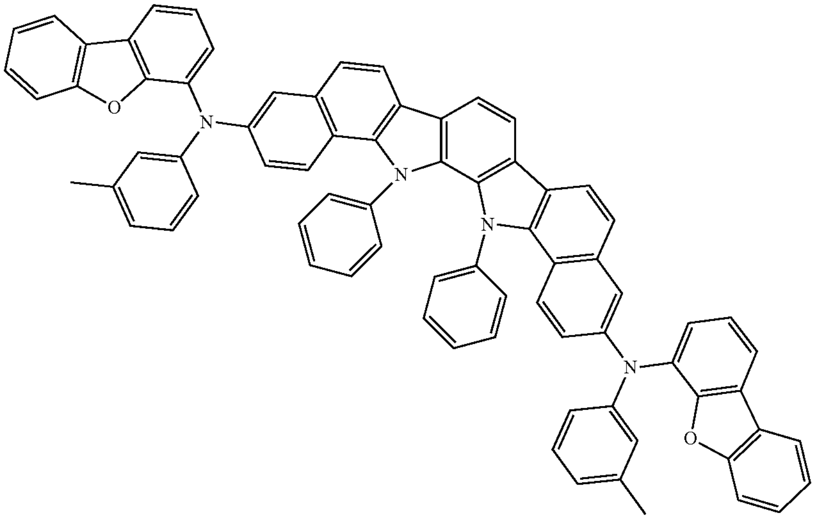
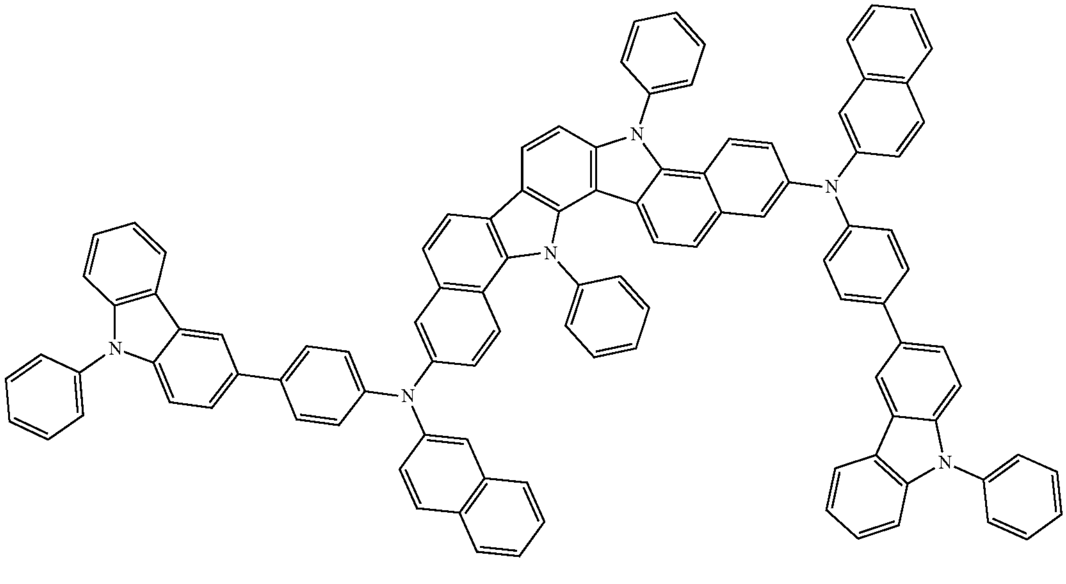

-continued
7
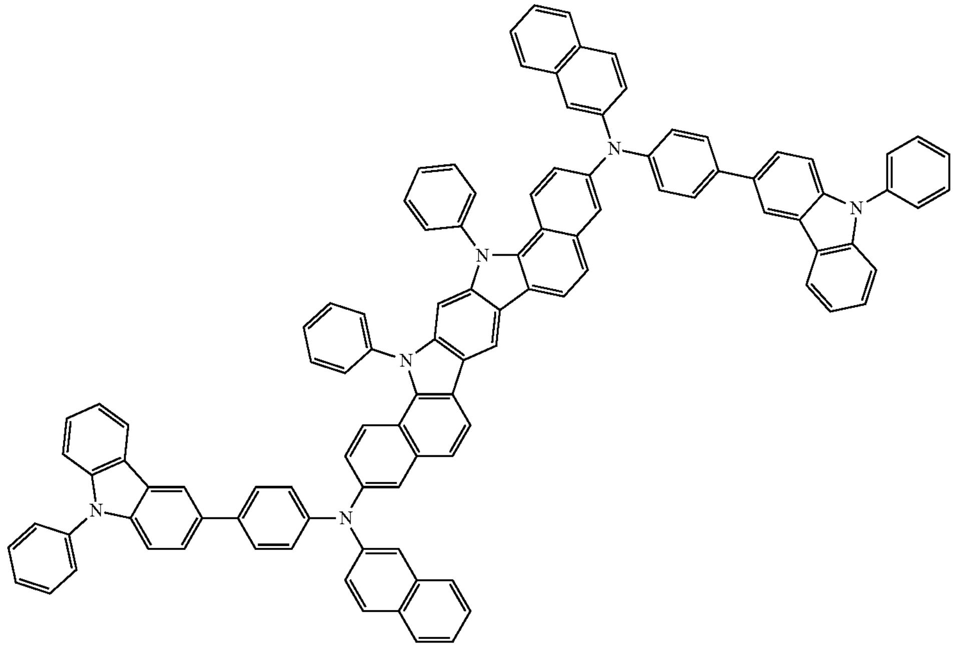
8
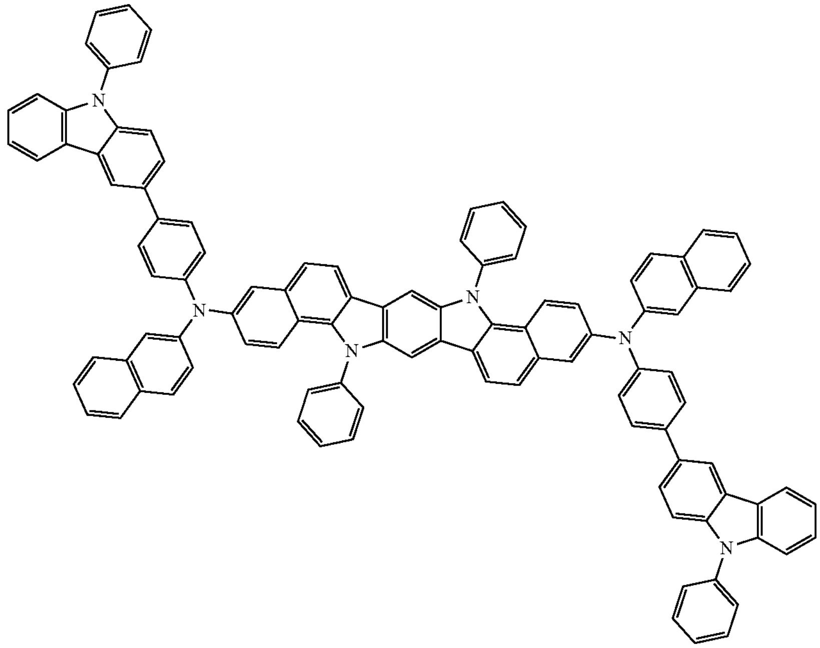

-continued
9
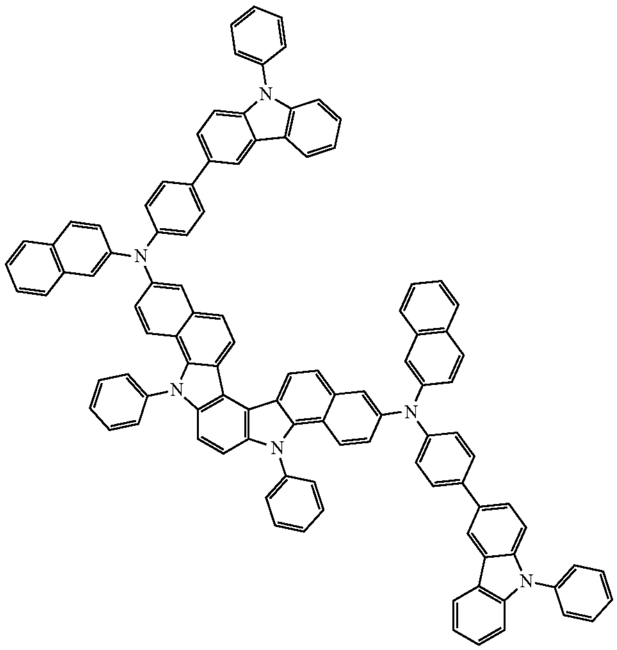
10
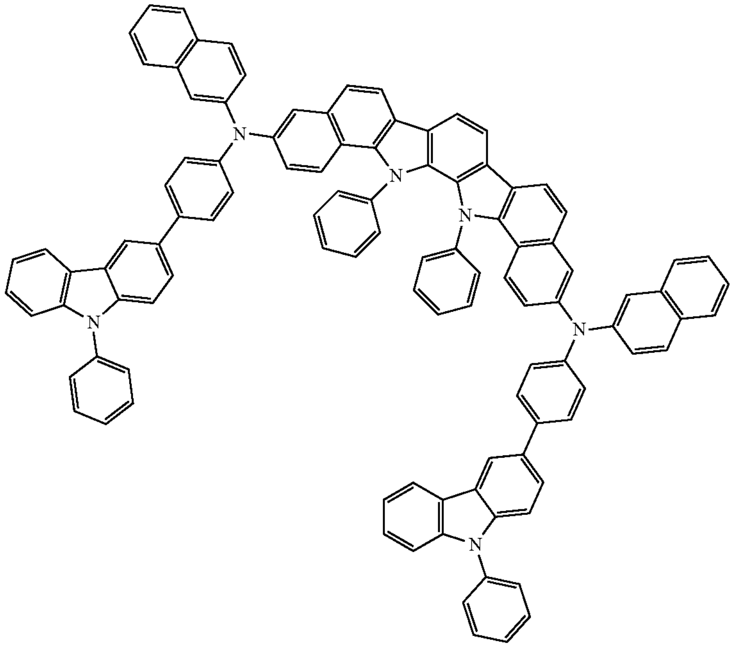

-continued
11
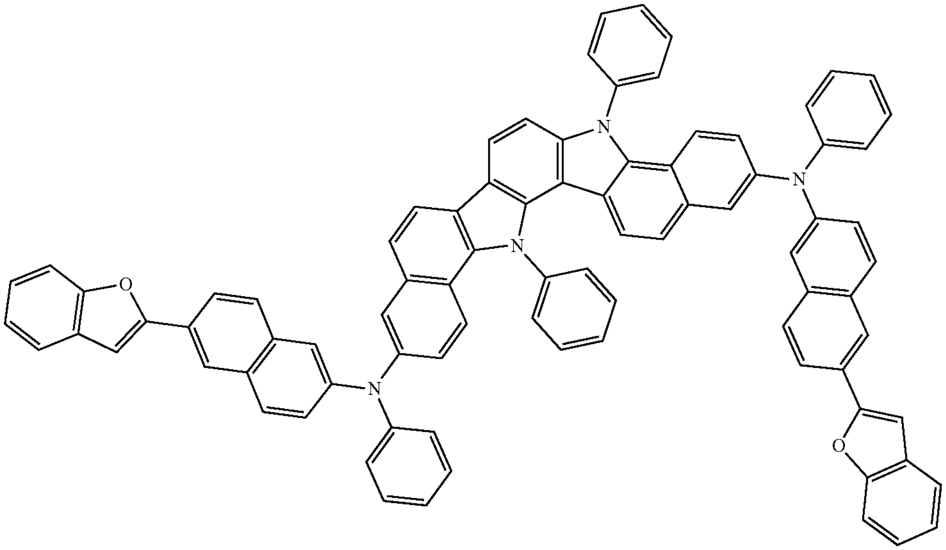
12
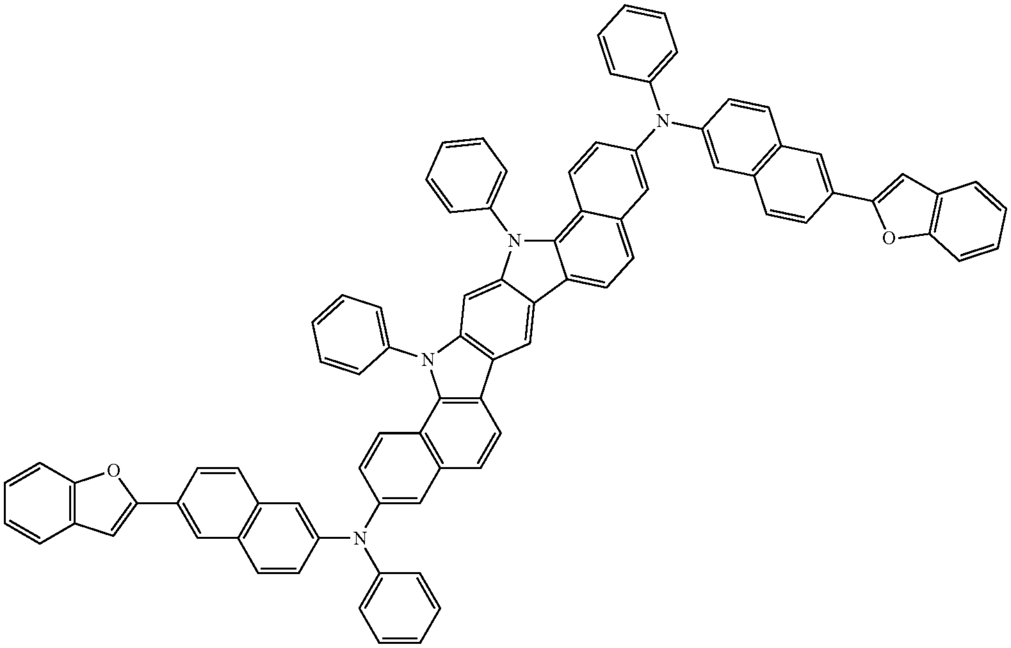

-continued
13
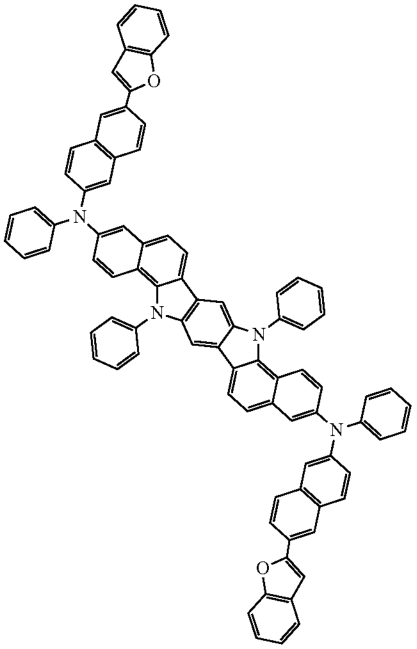
14
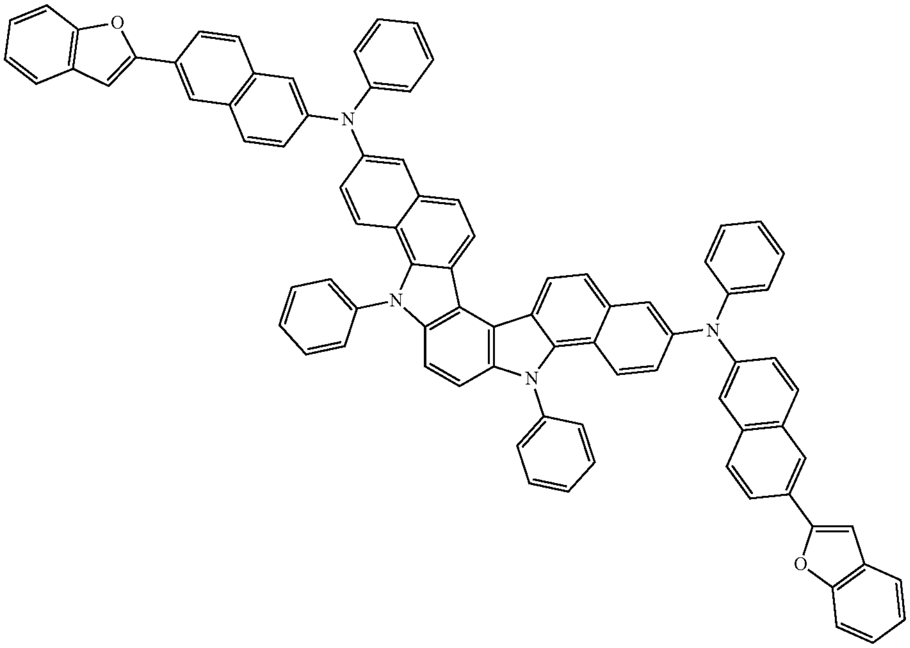

-continued
15
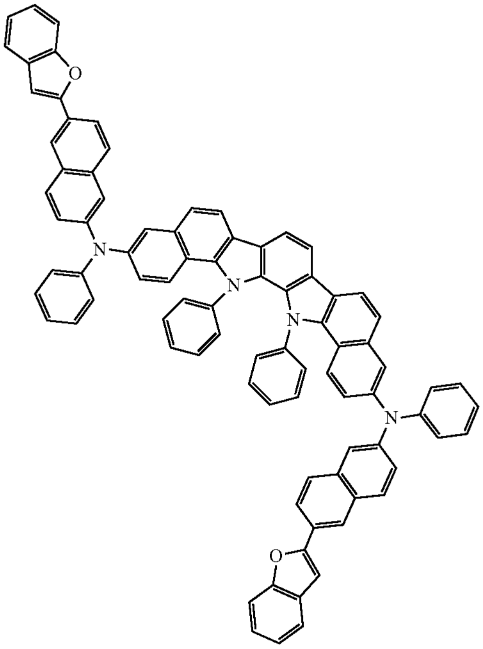
16
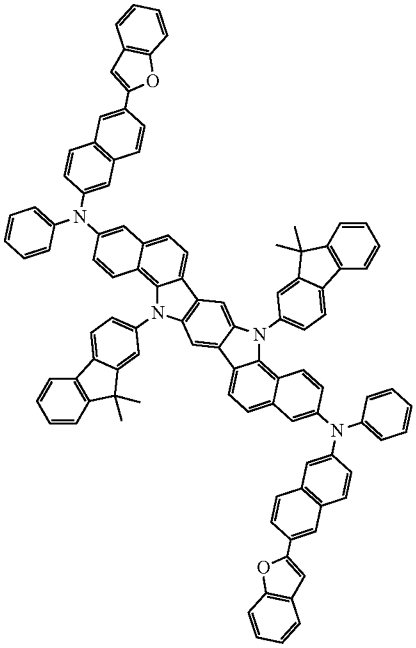
17
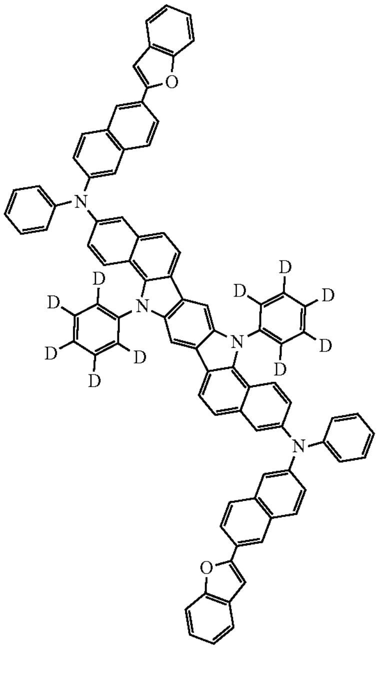

-continued
18
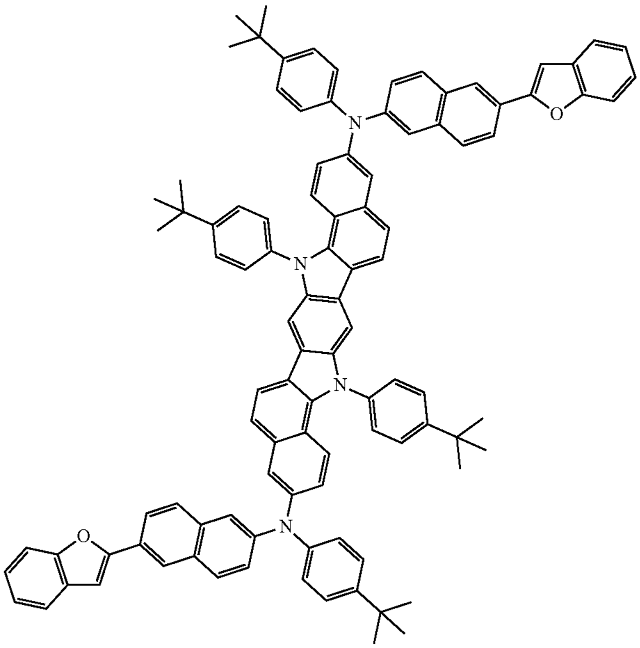
F
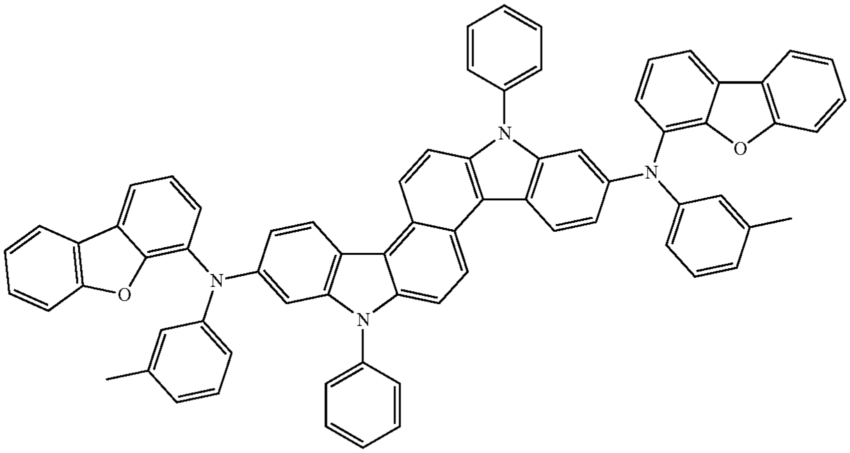
G
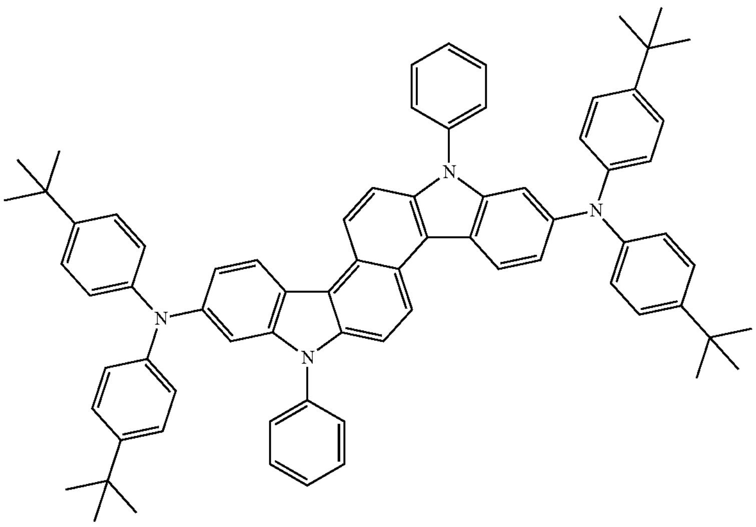

-continued

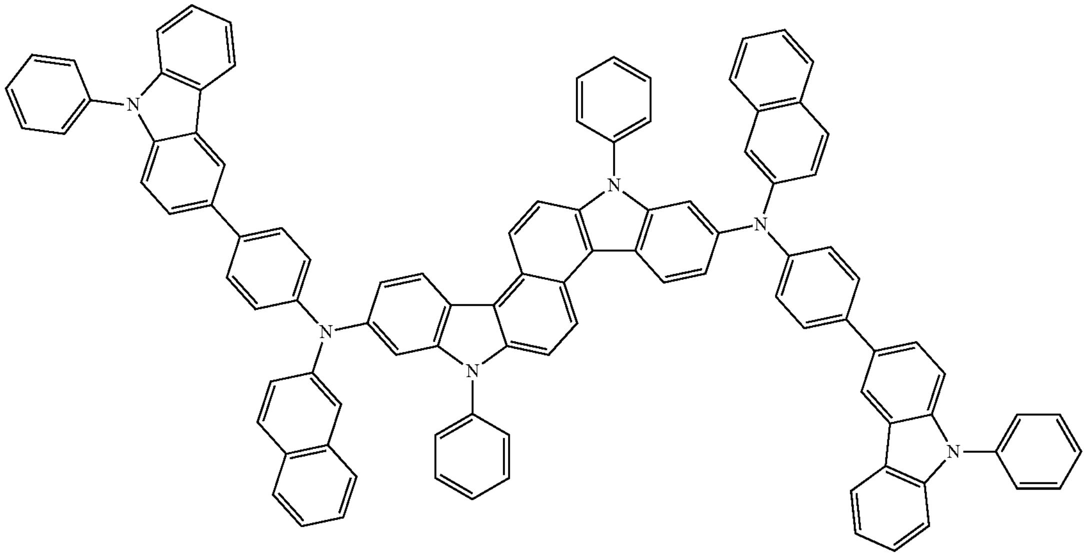

H

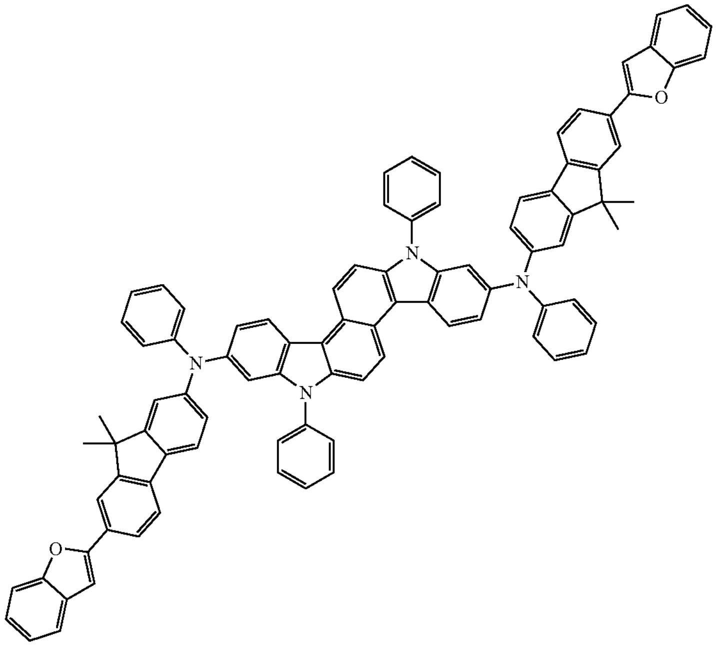

I

Experimental Example 2

The driving voltage, external quantum efficiency (EQE), and lifetime were measured by applying a current of 10 mA/$cm^2$ to the organic light emitting devices manufactured in the Examples and Comparative Examples, and the results are shown in Table 2 below. At this time, the external quantum efficiency (EQE) was calculated as "(the number of emitted photon)/(the number of injected charge carrier) *100", and T90 means the time required for the luminance to be reduced to 90% of the initial luminance (500 nit).

TABLE 2

| | Dopant of light emitting layer | Driving voltage (V @10 mA/$cm^2$) | EQE (% @10 mA/$cm^2$) | Lifetime (hr) (T90 @500 nit) |
|---|---|---|---|---|
| Example 1 | Compound 1 | 4.68 | 8.89 | 131 |
| Example 2 | Compound 2 | 4.69 | 8.87 | 133 |
| Example 3 | Compound 3 | 4.64 | 8.69 | 142 |
| Example 4 | Compound 4 | 4.62 | 8.87 | 129 |
| Example 5 | Compound 5 | 4.69 | 8.69 | 130 |
| Example 6 | Compound 6 | 4.61 | 8.78 | 127 |

TABLE 2-continued

| | Dopant of light emitting layer | Driving voltage (V @10 mA/cm²) | EQE (% @10 mA/cm²) | Lifetime (hr) (T90 @500 nit) |
|---|---|---|---|---|
| Example 7 | Compound 7 | 4.62 | 8.96 | 138 |
| Example 8 | Compound 8 | 4.67 | 8.57 | 140 |
| Example 9 | Compound 9 | 4.36 | 8.74 | 137 |
| Example 10 | Compound 10 | 4.52 | 8.69 | 129 |
| Example 11 | Compound 11 | 4.45 | 8.72 | 137 |
| Example 12 | Compound 12 | 4.68 | 8.80 | 129 |
| Example 13 | Compound 13 | 4.51 | 8.65 | 148 |
| Example 14 | Compound 14 | 4.63 | 8.67 | 137 |
| Example 15 | Compound 15 | 4.71 | 8.64 | 135 |
| Example 16 | Compound 16 | 4.62 | 8.75 | 142 |
| Example 17 | Compound 17 | 4.65 | 8.52 | 143 |
| Example 18 | Compound 18 | 4.70 | 8.69 | 146 |
| Comparative Example 1 | Compound F | 4.70 | 6.87 | 58 |
| Comparative Example 2 | Compound G | 4.68 | 7.11 | 67 |
| Comparative Example 3 | Compound H | 4.66 | 7.11 | 67 |

As shown in Table 2 above, it was confirmed that the organic light emitting devices manufactured by using the compounds of the present disclosure as the dopant of the light emitting layer exhibited excellent characteristics in terms of conversion efficiency and lifetime, as compared with the organic light emitting devices manufactured by using Compound F, Compound G or Compound H of Comparative Examples as the dopant of the light emitting layer.

| [Description of symbols] | |
|---|---|
| 1: substrate | 2: anode |
| 3: light emitting layer | 4: cathode |
| 5: hole injection layer | 6: hole transport layer |
| 7: electron injection and transport layer | |

The invention claimed is:

1. A compound represented by the following Chemical Formula 1:

[Chemical Formula 1]

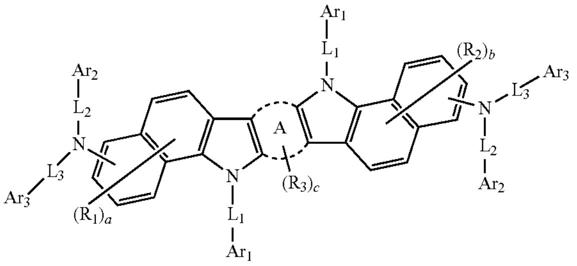

wherein in Chemical Formula 1,

A is a benzene ring fused with two adjacent pentagonal rings, $L_1$ to $L_3$ are each independently a single bond; a substituted or unsubstituted $C_{6-60}$ arylene; or a substituted or unsubstituted $C_{2-60}$ heteroarylene containing at least one heteroatom selected from N, O or S, $Ar_1$ to $Ar_3$ are each independently a substituted or unsubstituted $C_{6-60}$ aryl; or a substituted or unsubstituted $C_{2-60}$ heteroaryl containing at least one heteroatom selected among from N, O or S, $R_1$ to $R_3$ are each independently deuterium; halogen; cyano; a substituted or unsubstituted $C_{1-60}$ alkyl; a substituted or unsubstituted $C_{6-60}$ aryl; or a substituted or unsubstituted $C_{2-60}$ heteroaryl containing at least one heteroatom selected from N, O or S, a and b are each independently an integer of 0 to 5, and c is an integer of 0 to 2.

2. The compound of claim 1, wherein the compound is represented by any one of the following Chemical Formulas 1-1 to 1-5:

[Chemical Formula 1-1]

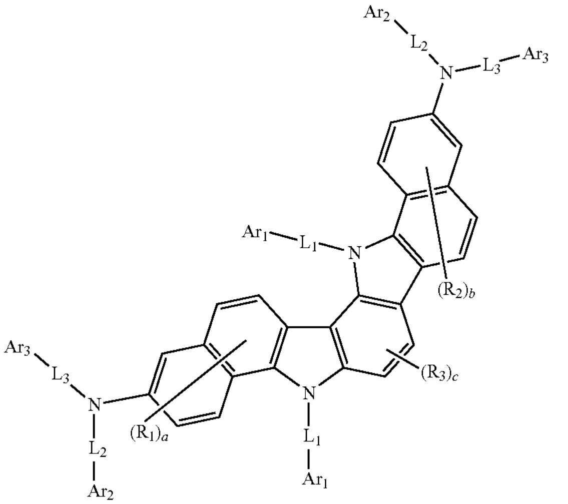

[Chemical Formula 1-2]

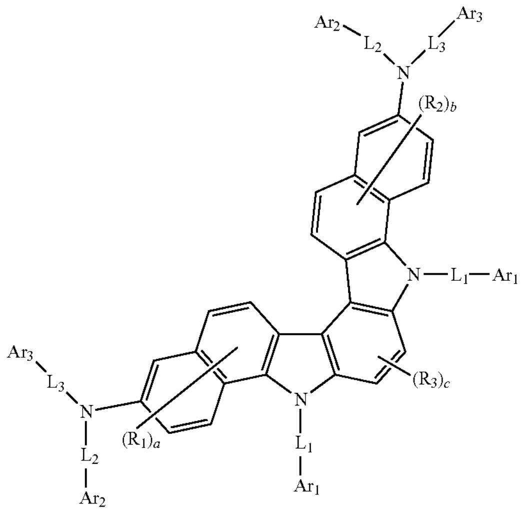

[Chemical Formula 1-3]

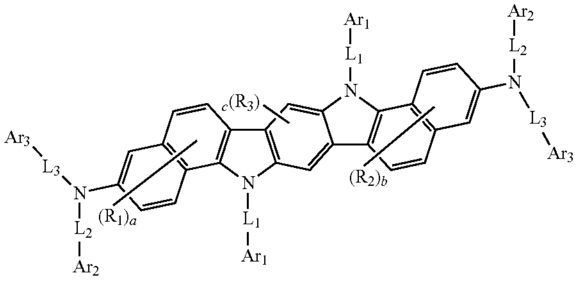

-continued

[Chemical Formula 1-4]

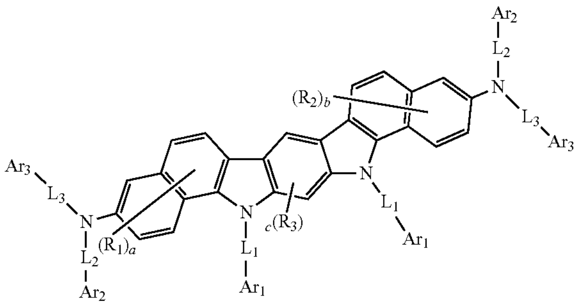

[Chemical Formula 1-5]

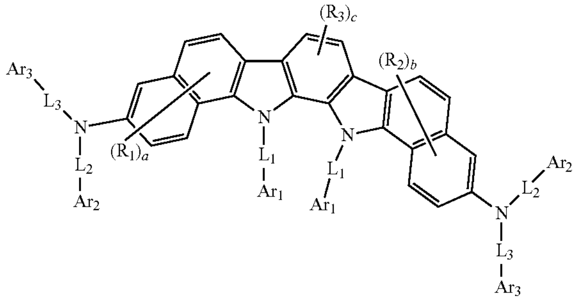

wherein in Chemical Formulas 1-1 to 1-5, $L_1$ to $L_3$, $Ar_1$ to $Ar_3$, $R_1$ to $R_3$, a, b and c are as defined in claim 1.

3. The compound of claim 1, wherein $L_1$ to $L_3$ are each independently a single bond, phenylene, biphenyldiyl, naphthylene, or 9,9-di($C_{1-10}$ alkyl) fluorenylene.

4. The compound of claim 1, wherein $Ar_1$ to $Ar_3$ are each independently a $C_{6-20}$ aryl which is unsubstituted or substituted with one or more substituents selected from the group consisting of deuterium, a $C_{1-10}$ alkyl, a $C_{6-20}$ aryl, a Si($C_{1-10}$ alkyl)$_3$ and a Si($C_{6-20}$ aryl)$_3$; or a $C_{2-20}$ heteroaryl containing 1 or 2 heteroatoms selected from N, O or S, unsubstituted or substituted with one or more substituents selected from the group consisting of deuterium, a $C_{1-10}$ alkyl, a $C_{6-20}$ aryl, a Si($C_{1-10}$ alkyl)$_3$ and a Si($C_{6-20}$ aryl)$_3$.

5. The compound of claim 4, wherein each $Ar_1$ is independently any one selected from the group consisting of:

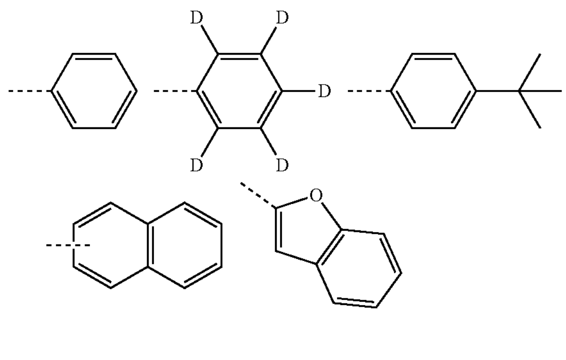

-continued

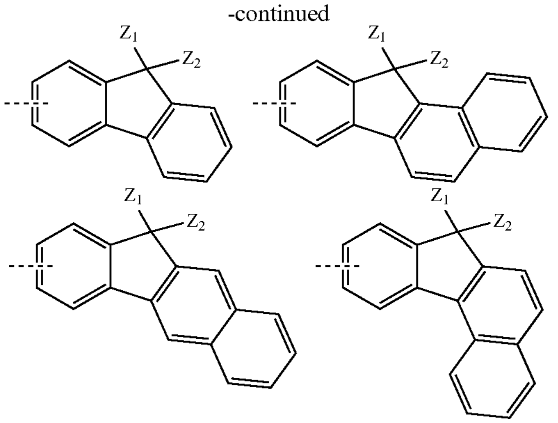

wherein, $Z_1$ and $Z_2$ are each independently methyl, ethyl, n-propyl, n-butyl, n-pentyl, n-hexyl, or phenyl.

6. The compound of claim 4, wherein $Ar_2$ and $Ar_3$ are each independently any one selected from the group consisting of:

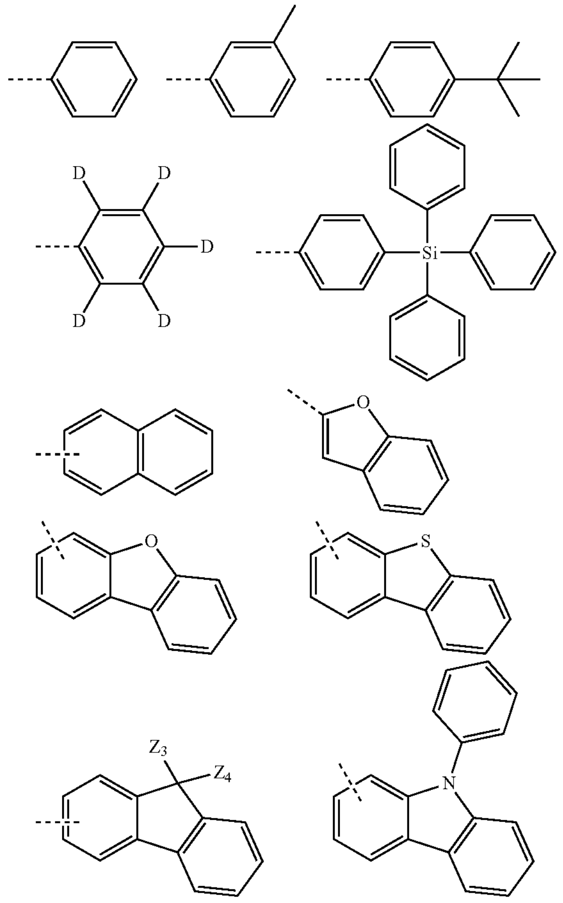

wherein, $Z_3$ and $Z_4$ are each independently methyl, ethyl, n-propyl, n-butyl, n-pentyl, n-hexyl, or phenyl.

7. The compound of claim 1, wherein one of $Ar_2$ or $Ar_3$ is phenyl, phenyl substituted with a $C_{1-10}$ alkyl, naphthyl, or benzofuranyl.

8. The compound of claim 1, wherein $R_1$ to $R_3$ are each deuterium.

9. The compound of claim 1, wherein $L_1$ is identical to each other, $L_2$ is identical to each other, $L_3$ is identical to each other, $Ar_1$ is identical to each other, $Ar_2$ is identical to each other, and $Ar_3$ is identical to each other.

10. The compound of claim 1, wherein the compound is represented by any one of the following Chemical Formulas 1-1-1 to 1-5-1:

[Chemical Formula 1-1-1]

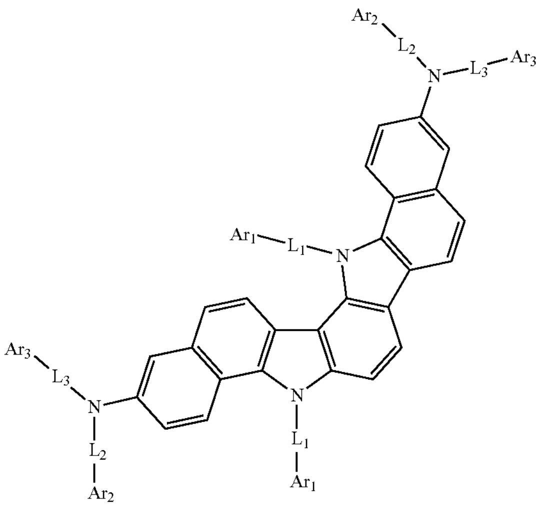

[Chemical Formula 1-2-1]

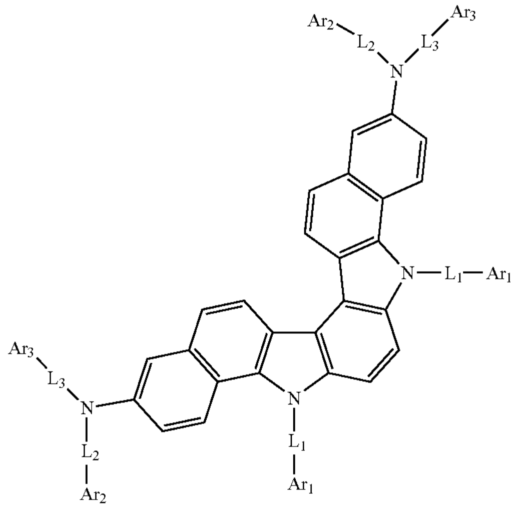

[Chemical Formula 1-3-1]

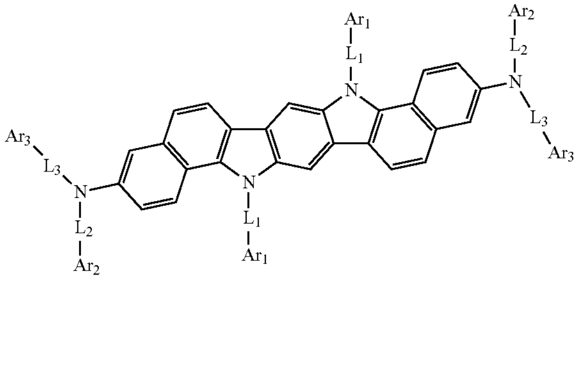

-continued

[Chemical Formula 1-4-1]

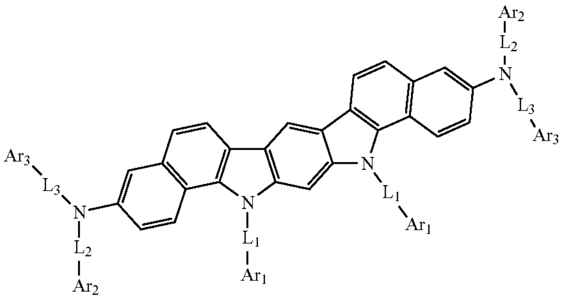

[Chemical Formula 1-5-1]

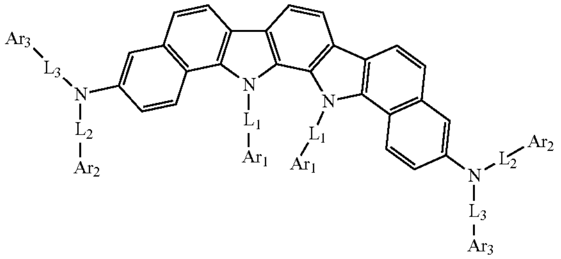

wherein in Chemical Formulas 1-1-1 to 1-5-1, each $L_1$ is independently a single bond, or any one selected from the group consisting of:

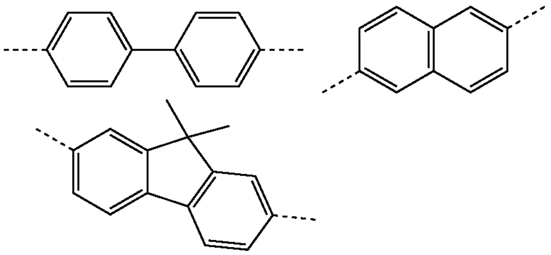

$L_2$ and $L_3$ are each independently, a single bond, or any one selected from the group consisting of:

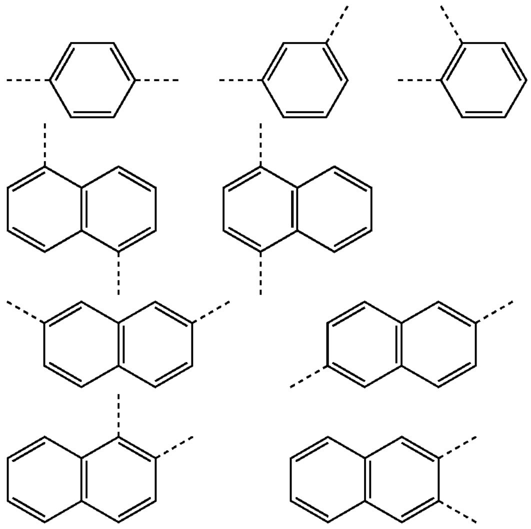

-continued
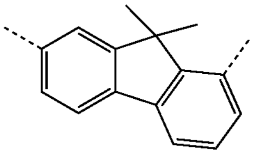
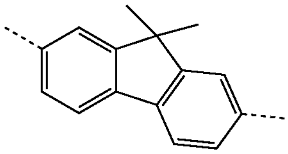
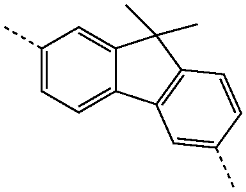
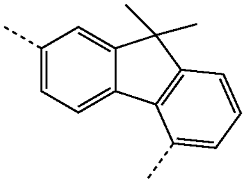
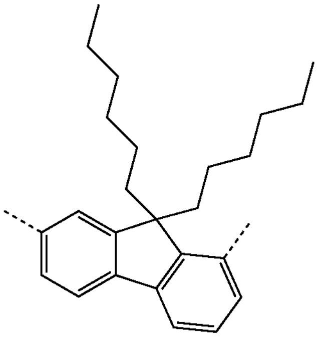
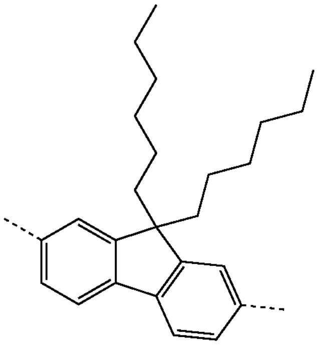
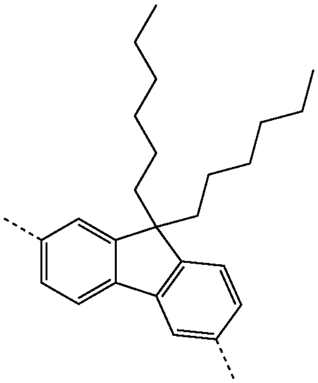
-continued
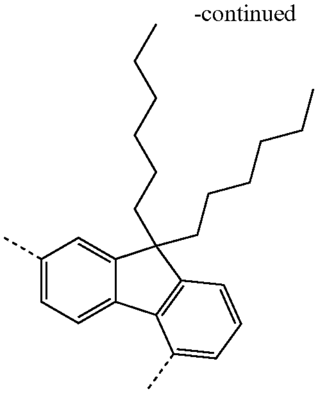
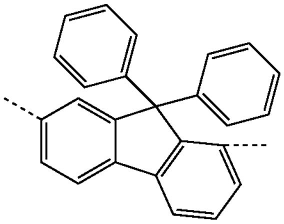
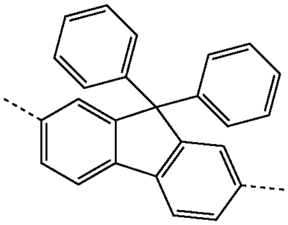
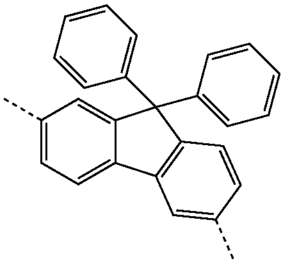
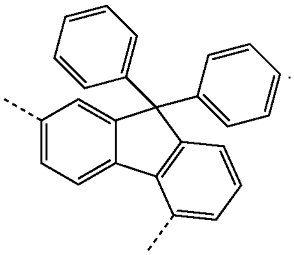
$Ar_1$ to $Ar_3$ are as defined in claim 1.
11. The compound of claim 1,
wherein the compound is any one selected from the group consisting of the following compounds:

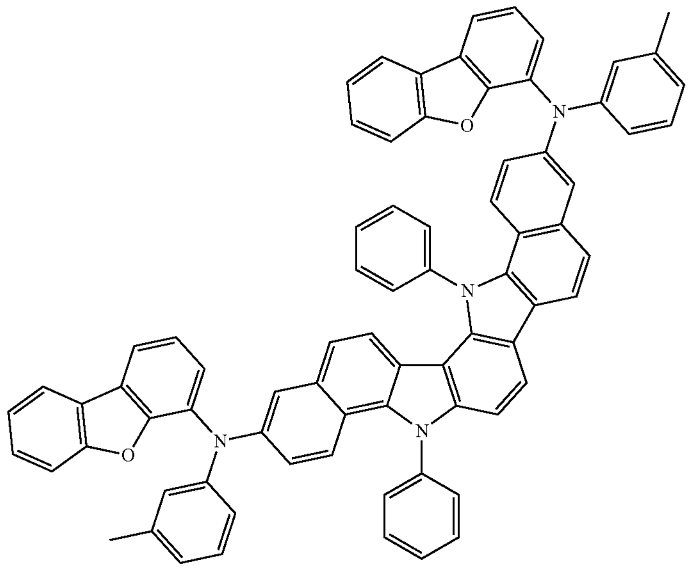
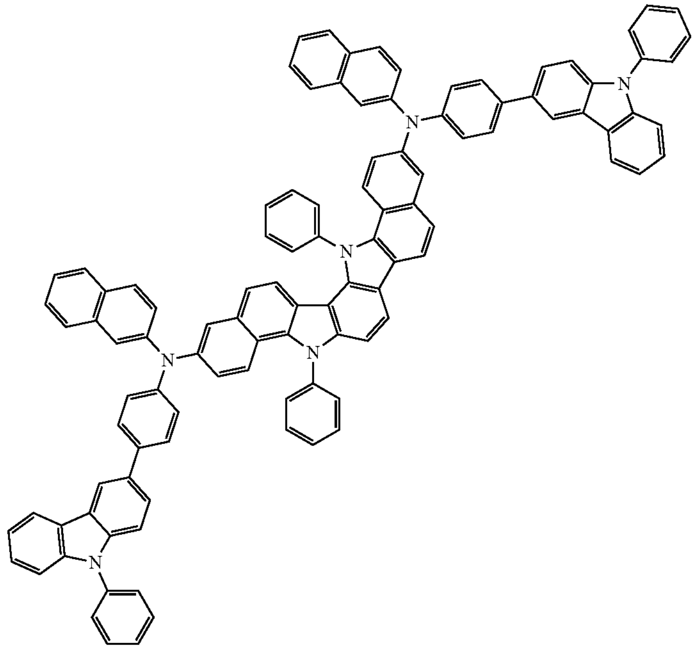

-continued
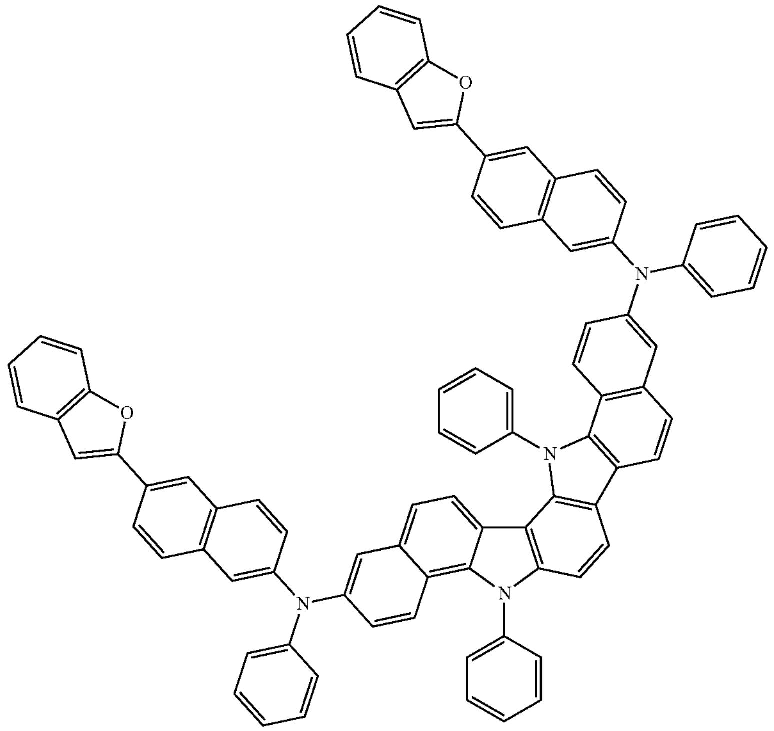
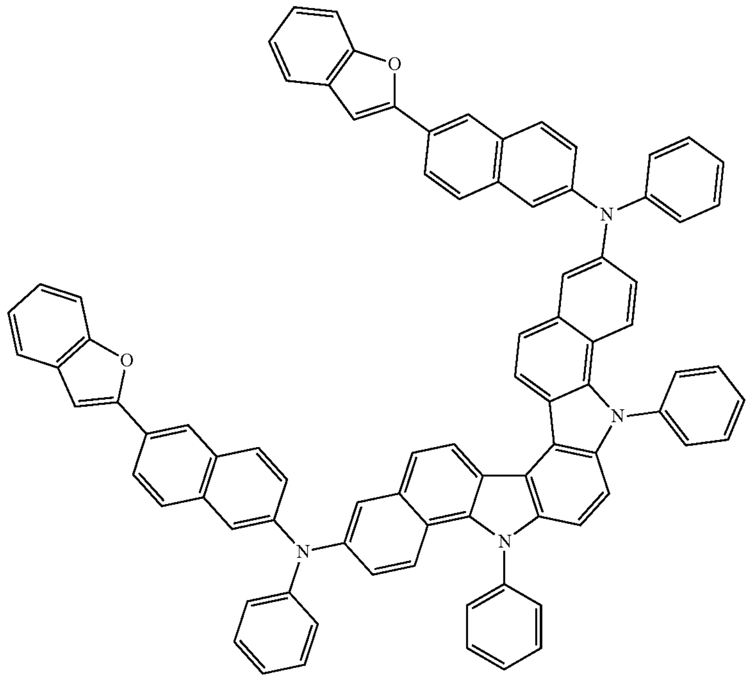

-continued
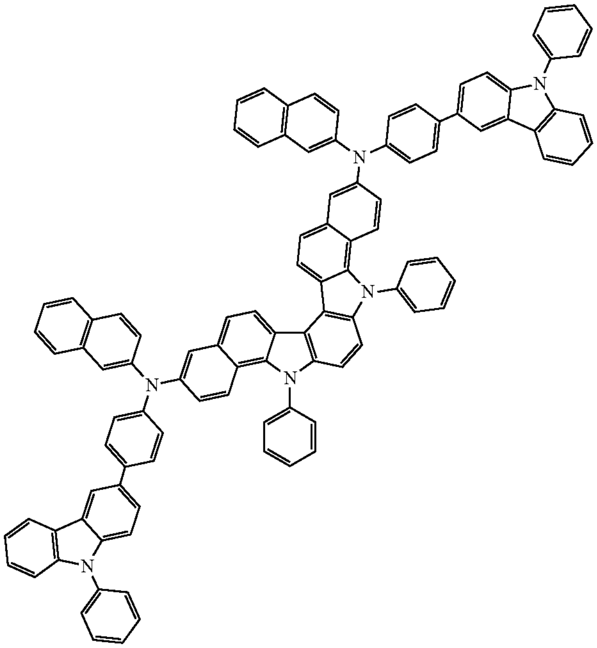
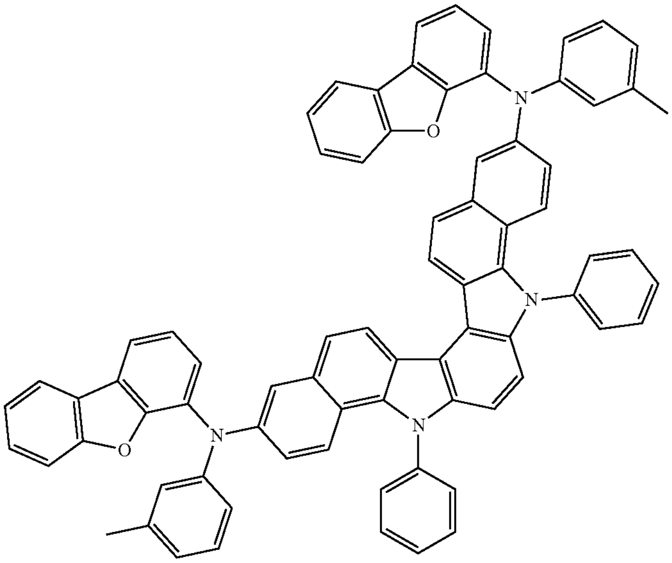
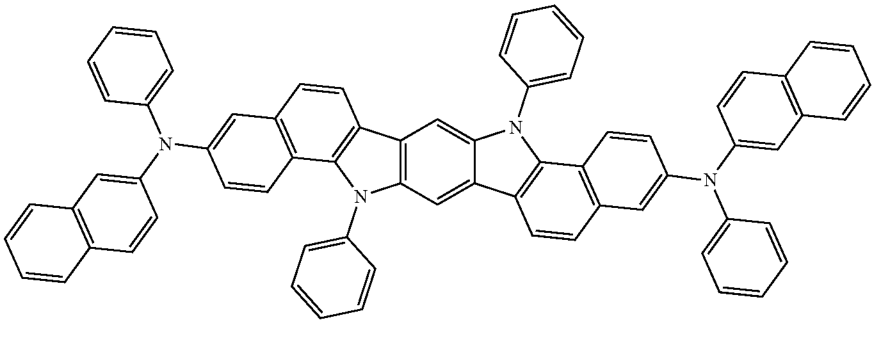

-continued
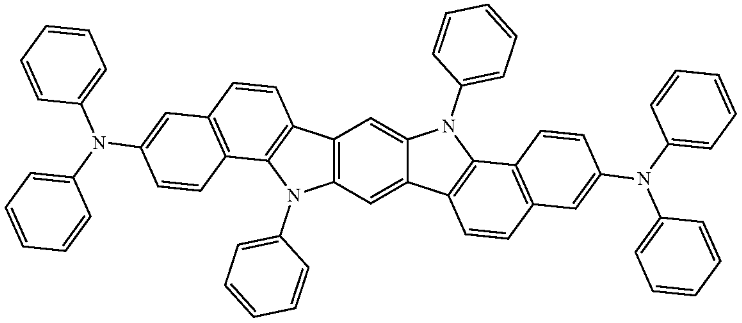
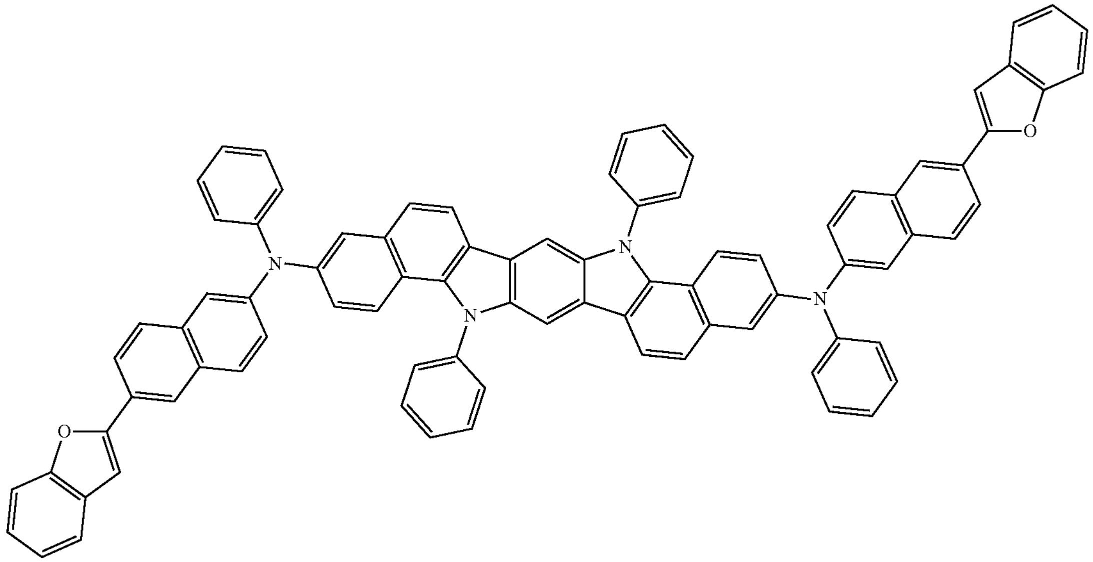
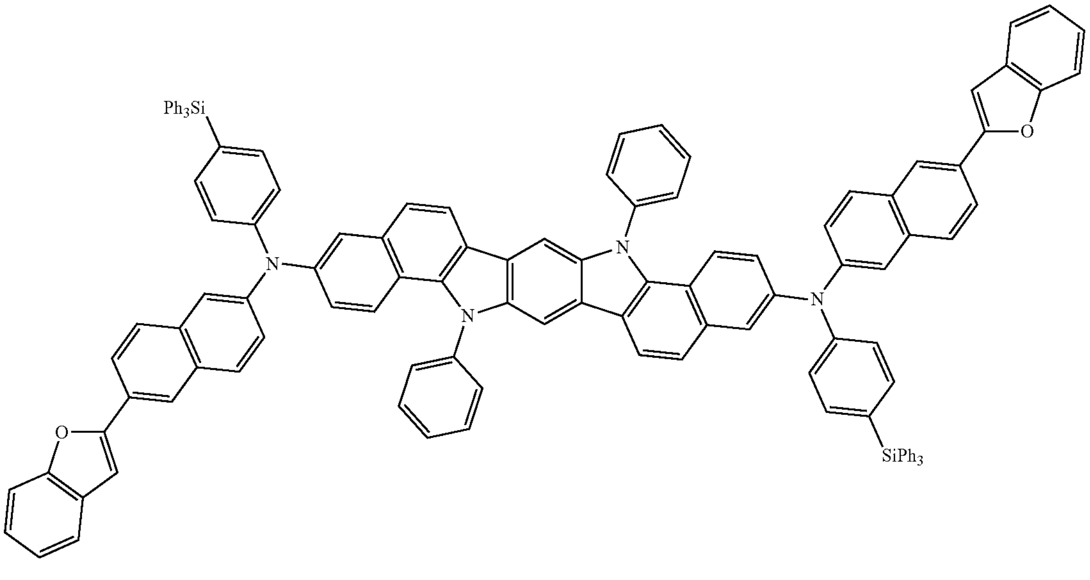

-continued
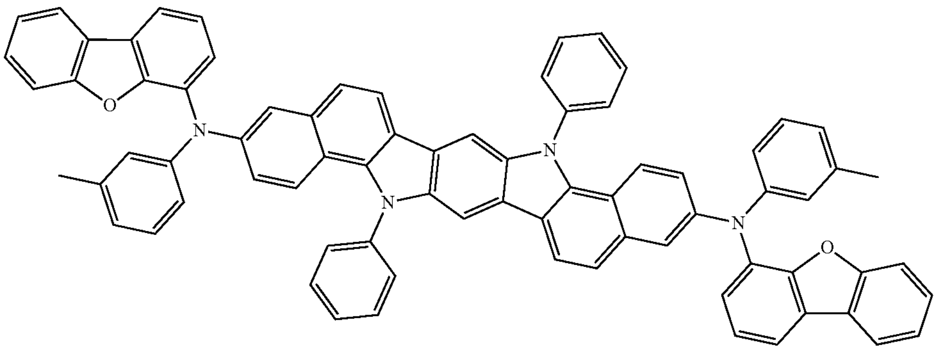
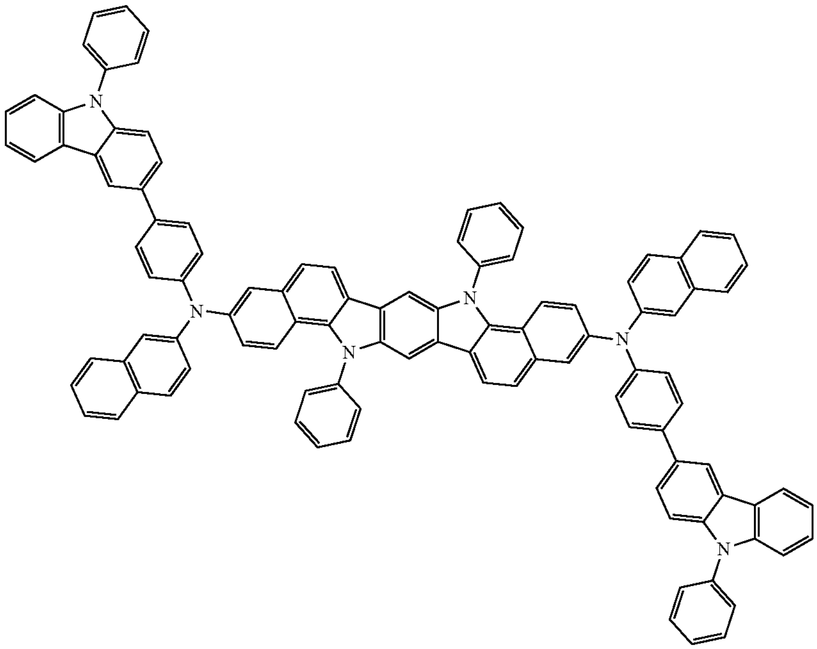
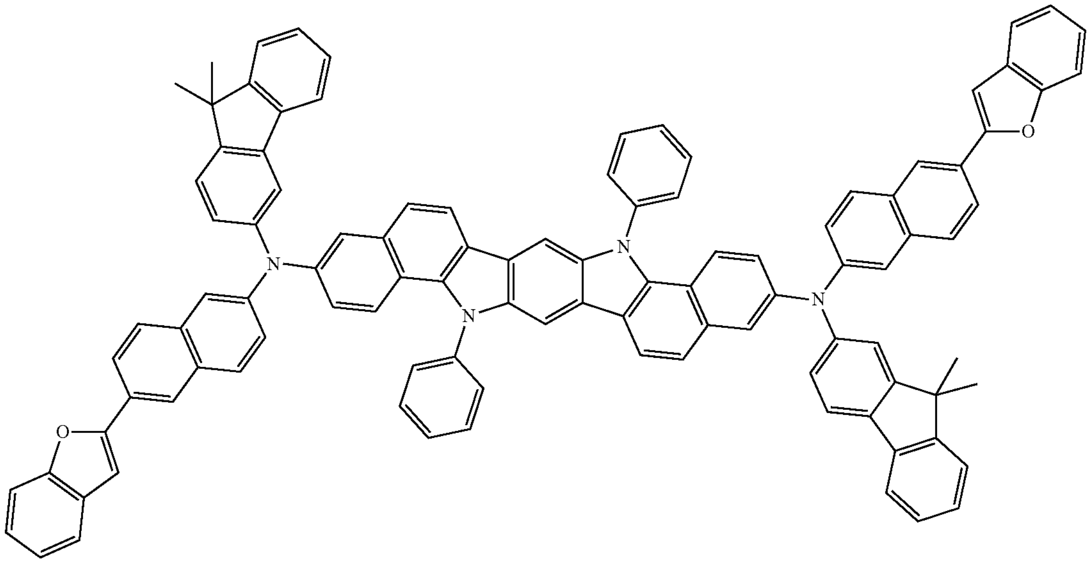

-continued
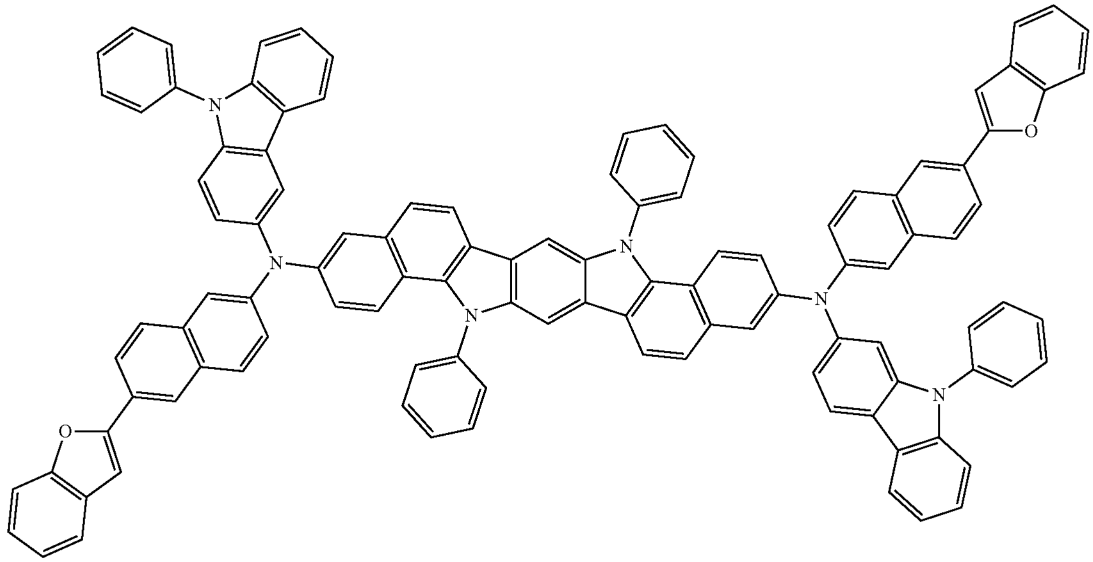
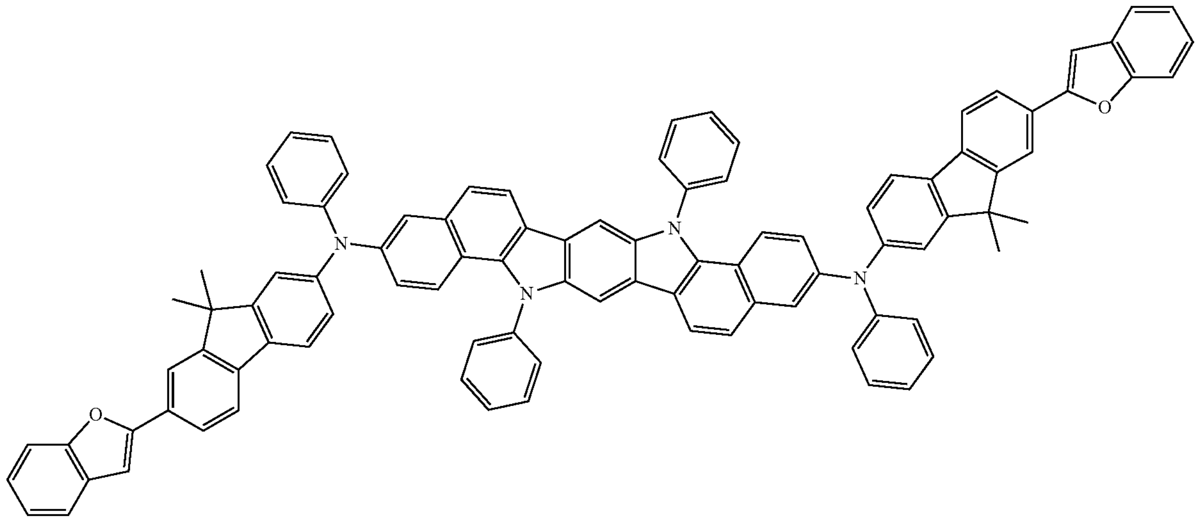
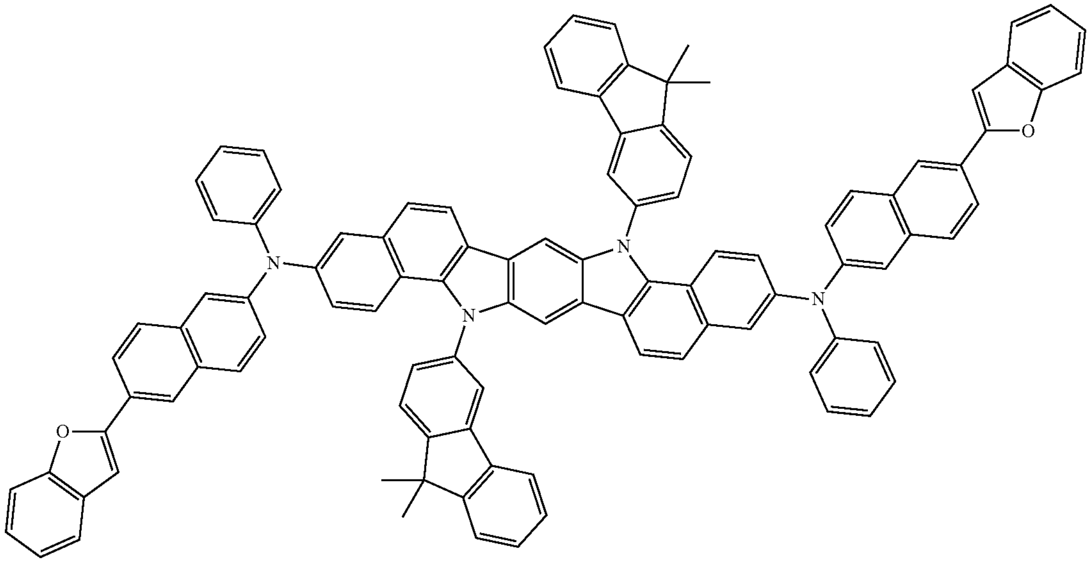

-continued
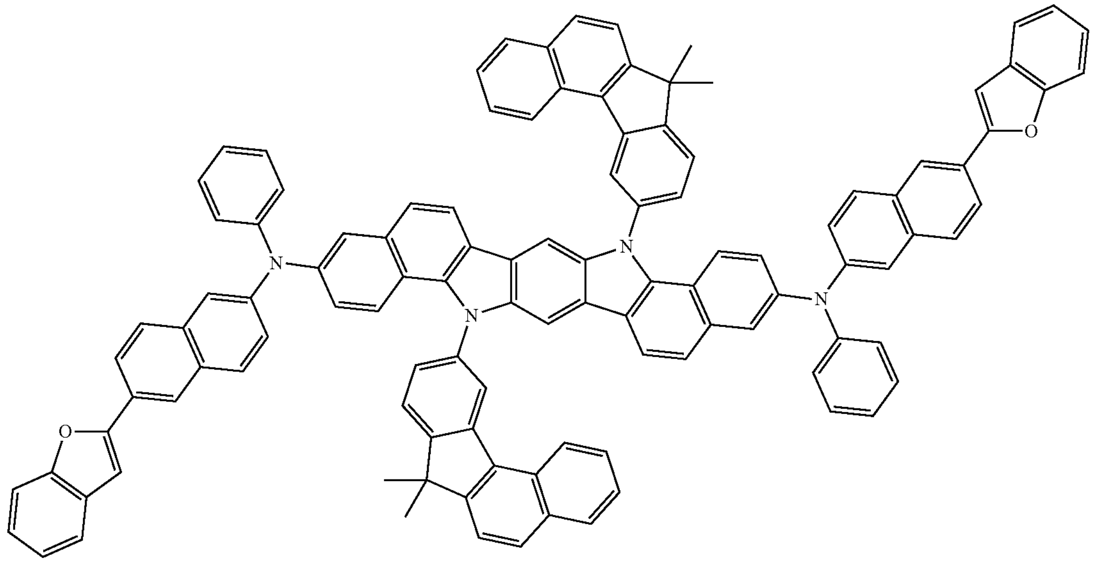
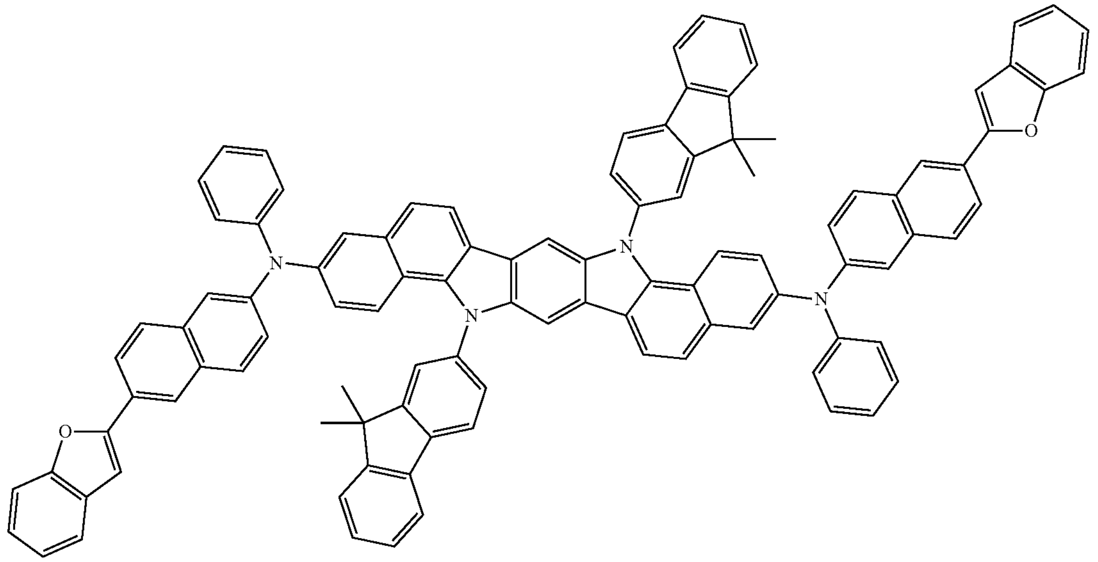
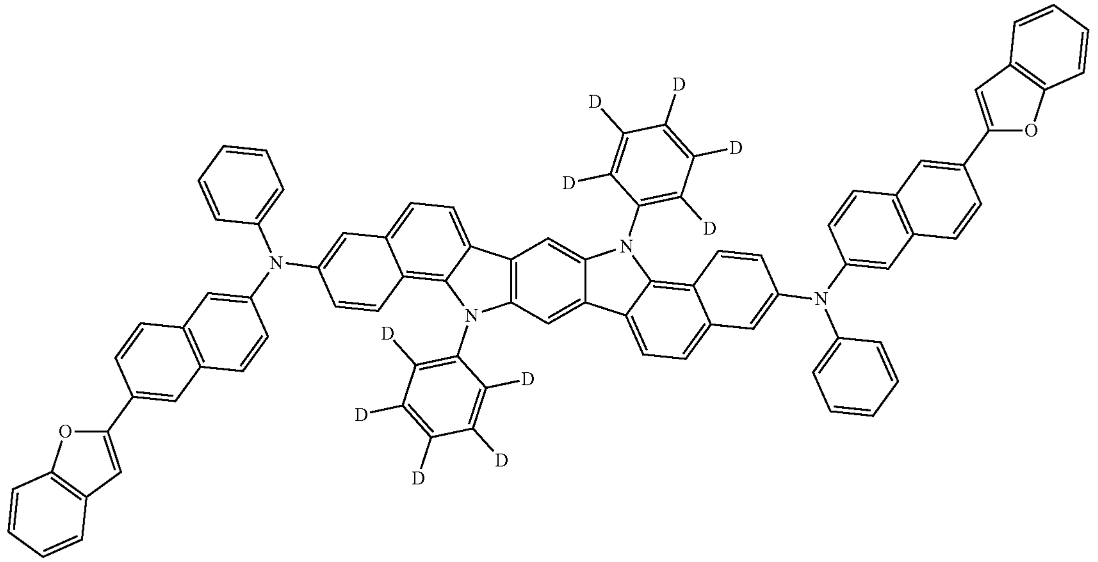

-continued
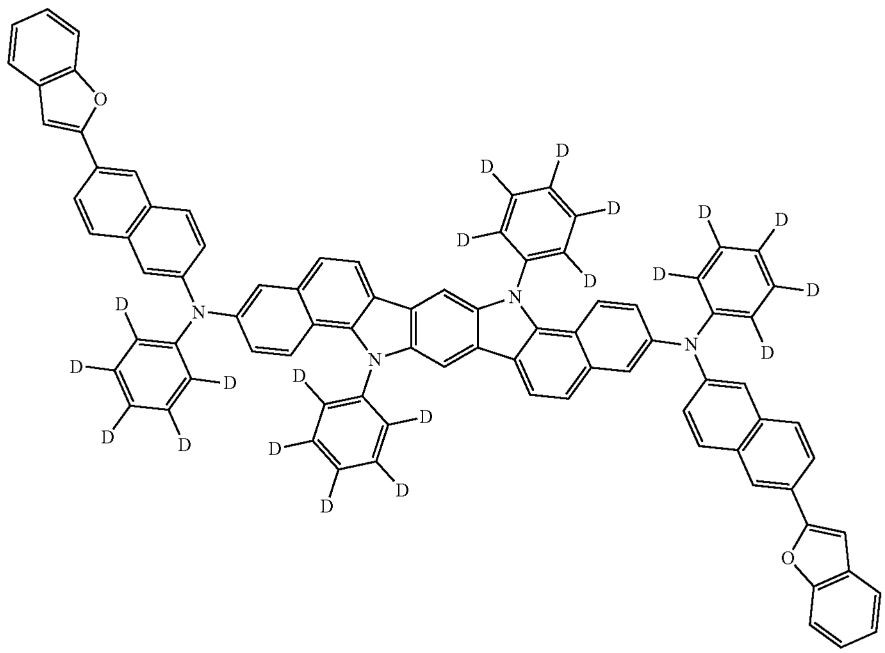
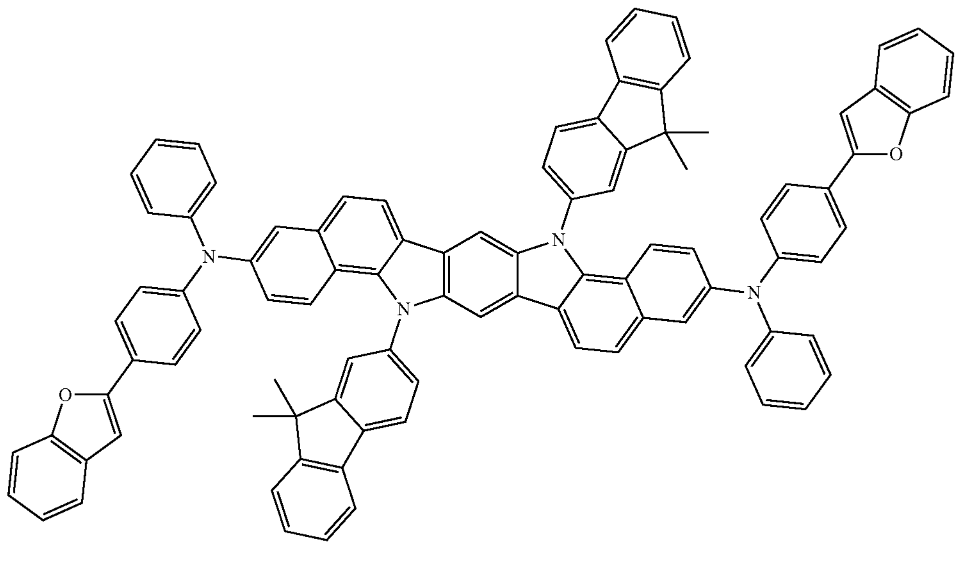

-continued
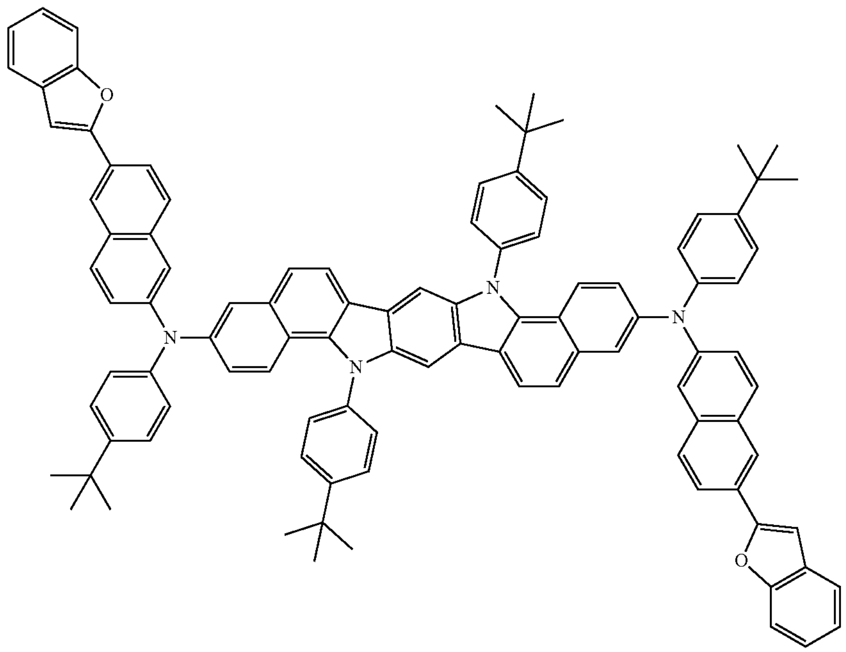
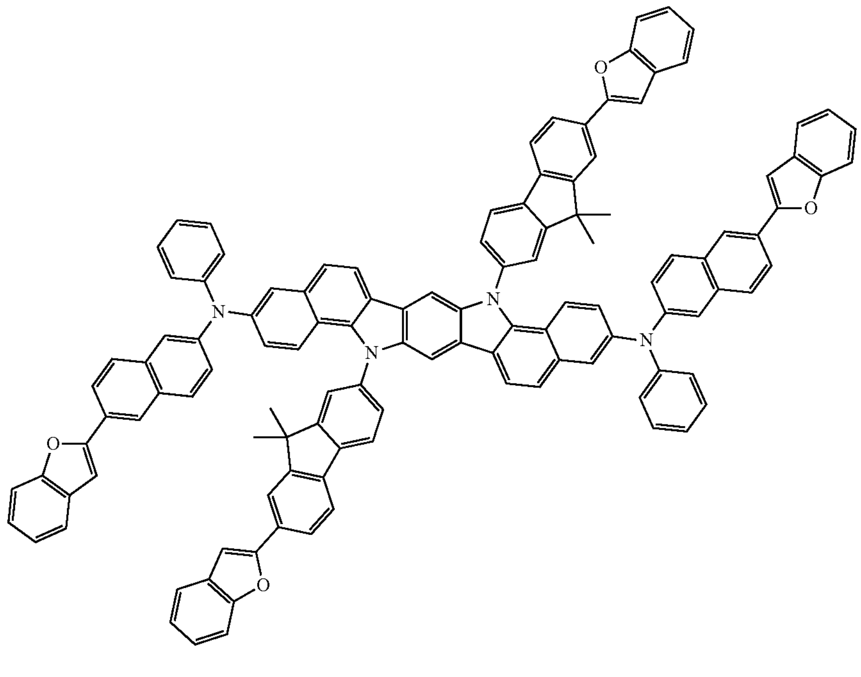

-continued
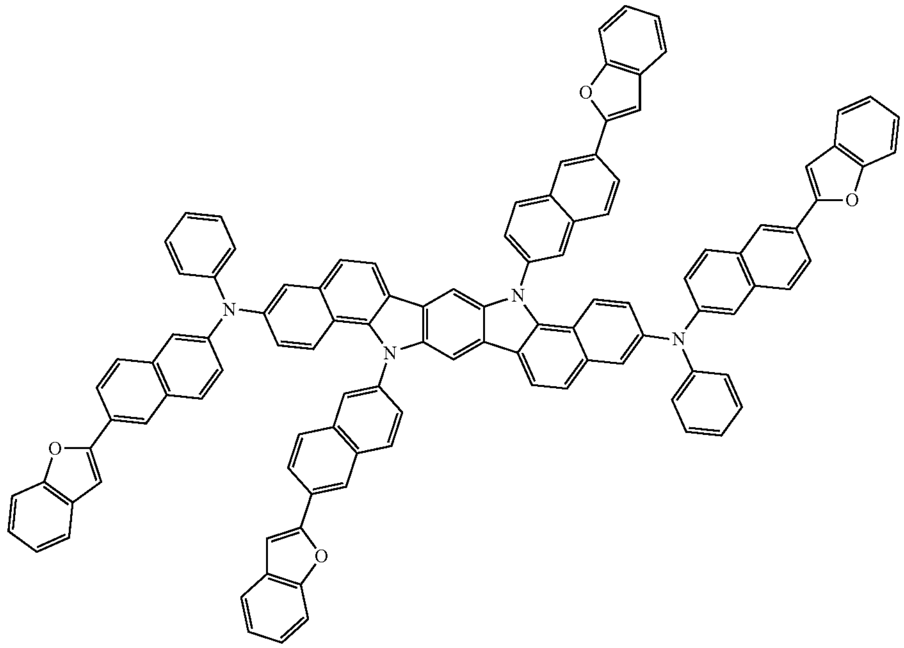
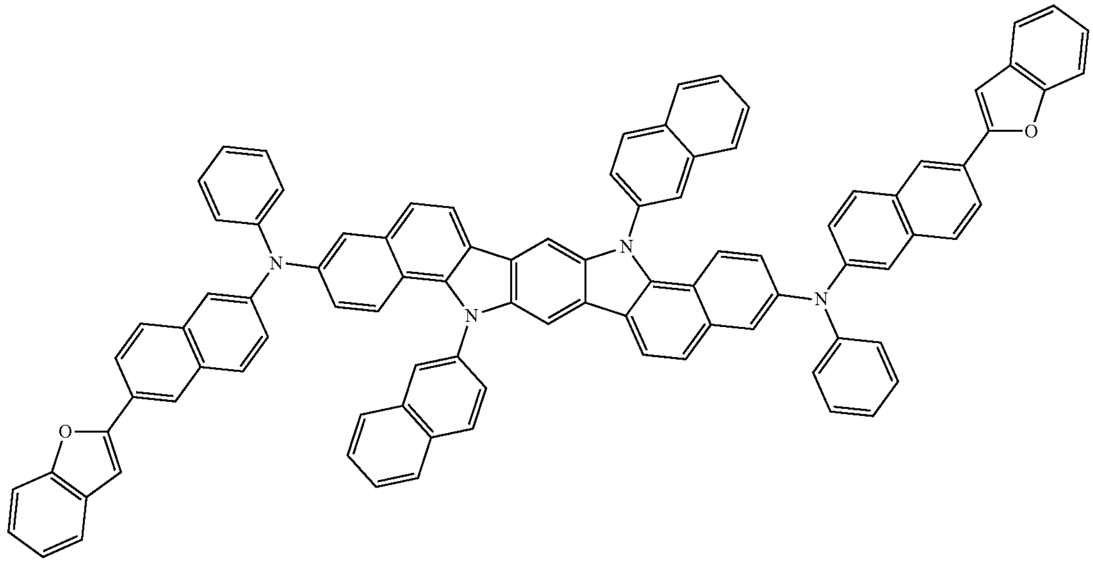
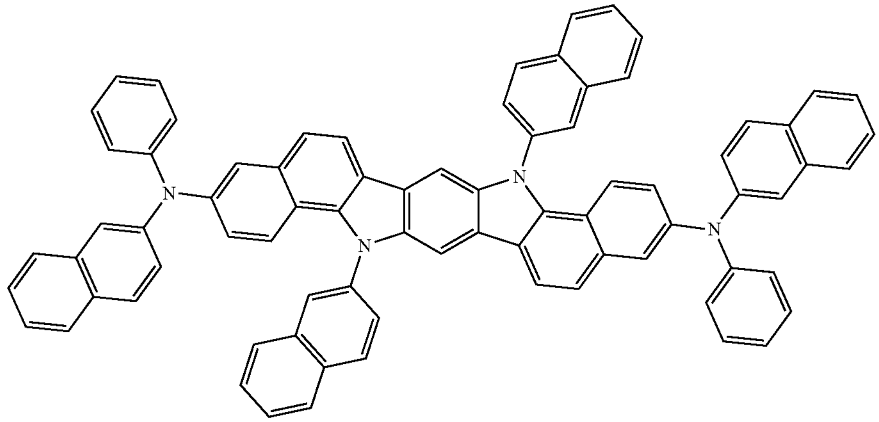

-continued
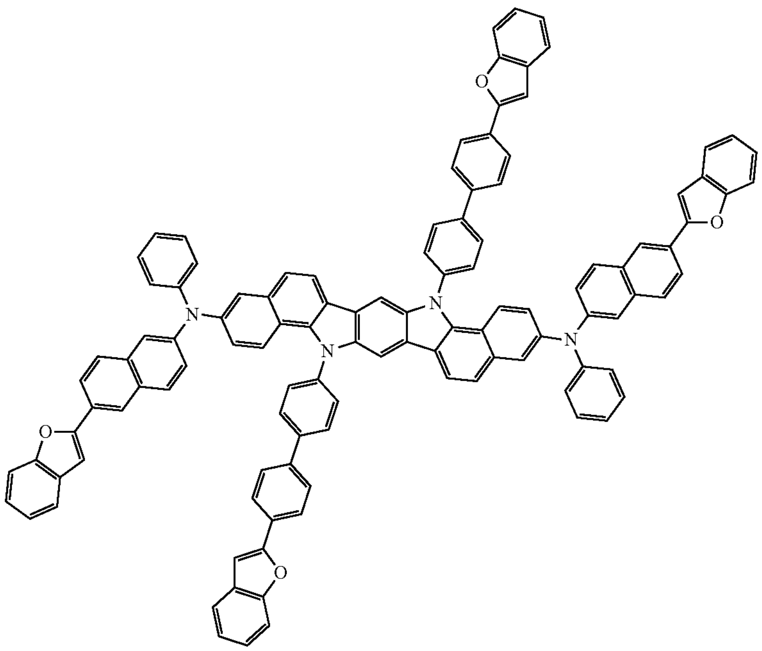
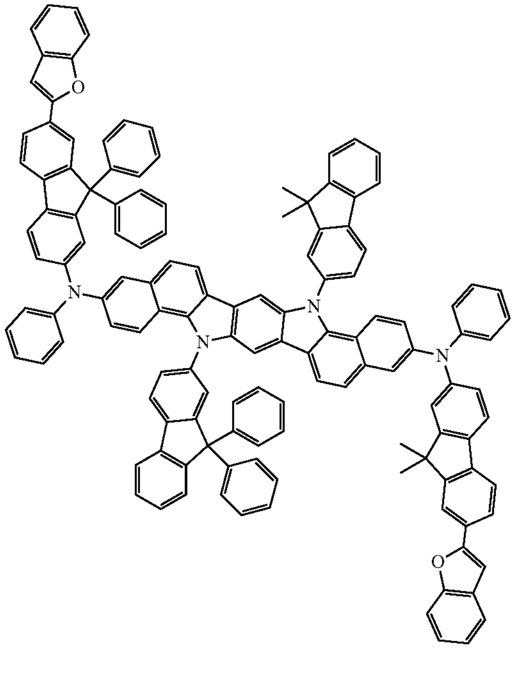

-continued
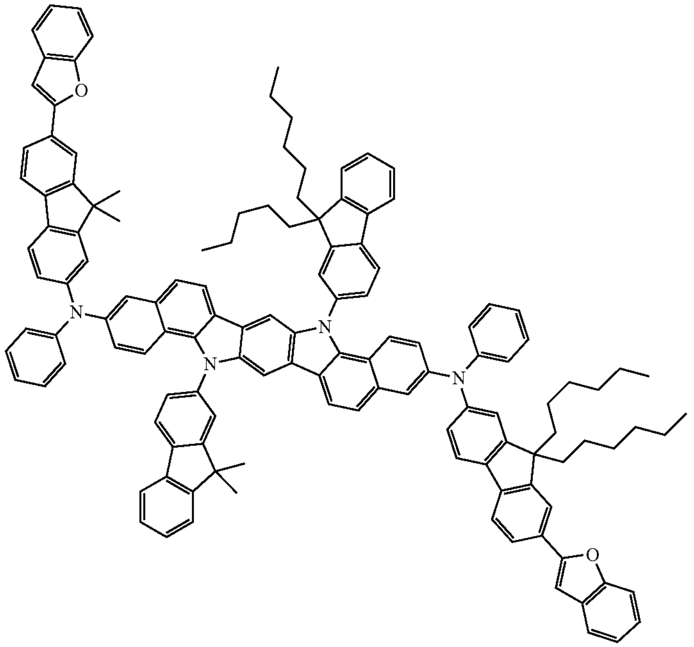
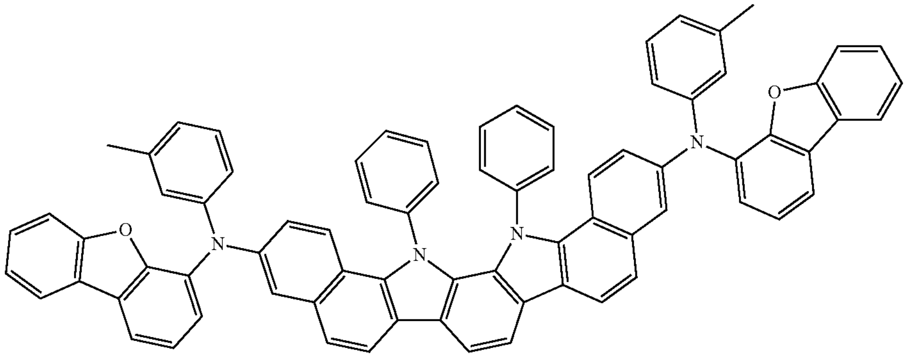
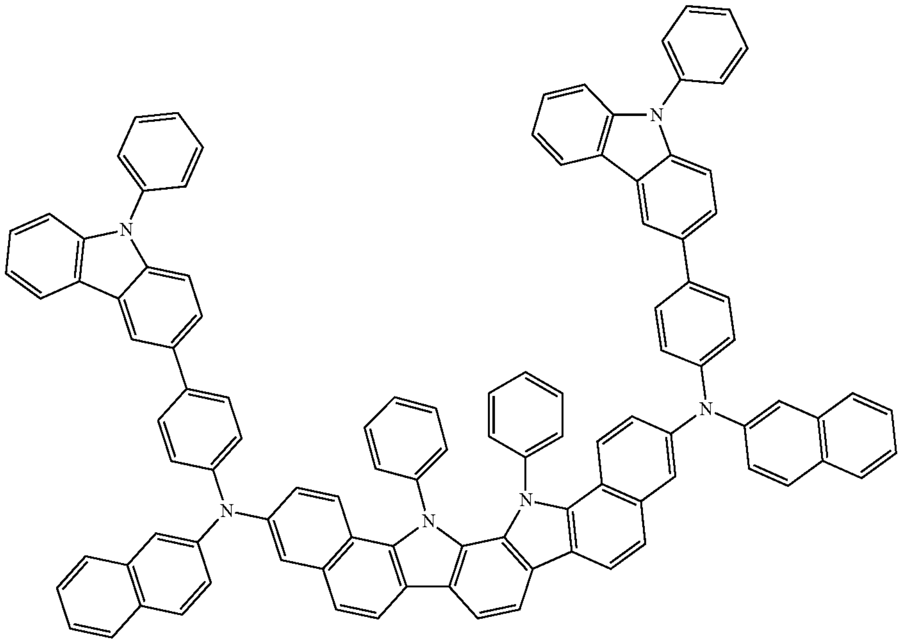

-continued
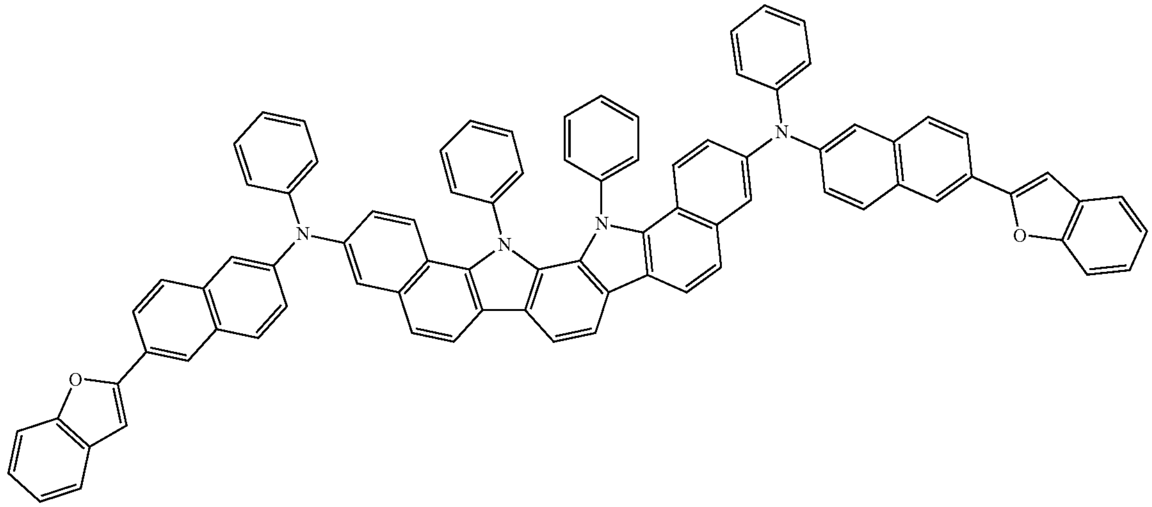
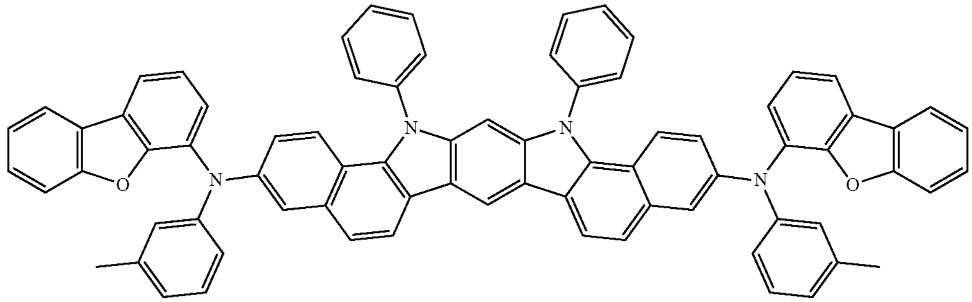
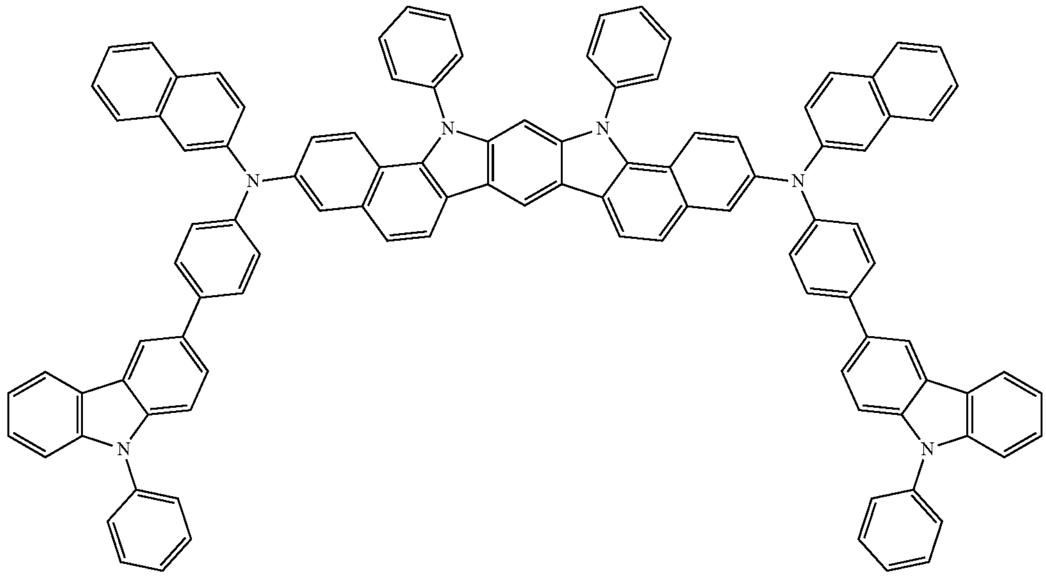

-continued
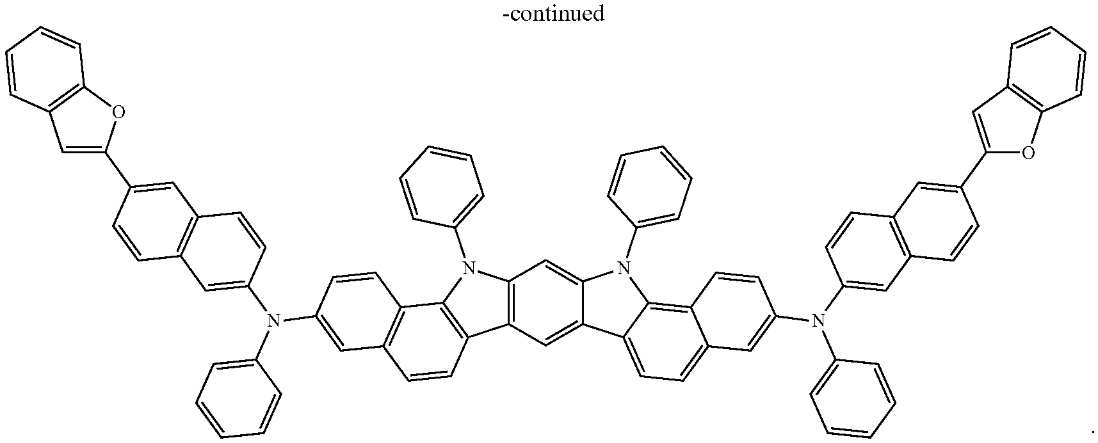
12. An organic light emitting device comprising: a first electrode; a second electrode that is provided opposite to the first electrode; and a light emitting layer that is provided between the first electrode and the second electrode, wherein the light emitting layer includes the compound of claim 1.
* * * * *